US007858591B2

(12) United States Patent
Sullenger et al.

(10) Patent No.: US 7,858,591 B2
(45) Date of Patent: Dec. 28, 2010

(54) RNA APTAMERS AND METHODS FOR IDENTIFYING THE SAME

(75) Inventors: Bruce A. Sullenger, Durham, NC (US); Christopher P. Rusconi, Durham, NC (US)

(73) Assignee: Duke University, Durham, NC (US)

(*) Notice: Subject to any disclaimer, the term of this patent is extended or adjusted under 35 U.S.C. 154(b) by 0 days.

(21) Appl. No.: 11/925,651

(22) Filed: Oct. 26, 2007

(65) Prior Publication Data

US 2008/0200413 A1 Aug. 21, 2008

Related U.S. Application Data

(62) Division of application No. 09/963,827, filed on Sep. 26, 2001, now Pat. No. 7,312,325.

(60) Provisional application No. 60/235,654, filed on Sep. 26, 2000.

(51) Int. Cl.

| | |
|---|---|
| ***A61K 31/70*** | (2006.01) |
| *C07H 21/02* | (2006.01) |
| *C07H 21/04* | (2006.01) |
| *C12Q 1/68* | (2006.01) |

(52) U.S. Cl. ......................... 514/44 R; 435/6; 435/375; 435/377; 536/23.1; 536/24.1; 536/24.5

(58) Field of Classification Search ....................... None
See application file for complete search history.

(56) References Cited

U.S. PATENT DOCUMENTS

| | | | |
|---|---|---|---|
| 5,245,022 | A | 9/1993 | Weis et al. |
| 5,270,163 | A | 12/1993 | Gold et al. |
| 5,475,096 | A | 12/1995 | Gold et al. |
| 5,476,766 | A | 12/1995 | Gold et al. |
| 5,532,130 | A | 7/1996 | Alul |
| 5,534,408 | A | 7/1996 | Green et al. |
| 5,543,293 | A | 8/1996 | Gold et al. |
| 5,552,391 | A | 9/1996 | Coutts et al. |
| 5,582,981 | A | 12/1996 | Toole et al. |
| 5,594,121 | A | 1/1997 | Froehler et al. |
| 5,595,877 | A | 1/1997 | Gold et al. |
| 5,606,047 | A | 2/1997 | Coutts et al. |
| 5,645,985 | A | 7/1997 | Froehler et al. |
| 5,648,214 | A | 7/1997 | Nieuwlandt et al. |
| 5,660,985 | A | 8/1997 | Pieken et al. |
| 5,670,633 | A | 9/1997 | Cook et al. |
| 5,670,637 | A | 9/1997 | Gold et al. |
| 5,681,702 | A | 10/1997 | Collins et al. |
| 5,686,242 | A | 11/1997 | Bruice et al. |
| 5,696,249 | A | 12/1997 | Gold et al. |
| 5,723,323 | A | 3/1998 | Kauffman et al. |
| 5,750,729 | A | 5/1998 | Alexander et al. |
| 5,756,291 | A | 5/1998 | Griffin et al. |
| 5,760,202 | A | 6/1998 | Cook et al. |
| 5,780,221 | A | 7/1998 | Schumacher et al. |
| 5,780,449 | A | 7/1998 | Bracht et al. |
| 5,780,610 | A | 7/1998 | Collins et al. |
| 5,792,608 | A | 8/1998 | Swaminathan et al. |
| 5,792,613 | A | 8/1998 | Schmidt et al. |
| 5,807,718 | A | 9/1998 | Joyce et al. |
| 5,814,476 | A | 9/1998 | Kauffman et al. |
| 5,817,781 | A | 10/1998 | Swaminathan et al. |
| 5,817,785 | A | 10/1998 | Gold et al. |
| 5,830,653 | A | 11/1998 | Froehler et al. |
| 5,839,443 | A | 11/1998 | Rose |
| 5,840,867 | A | 11/1998 | Toole et al. |
| 5,843,653 | A | 12/1998 | Gold et al. |
| 5,859,221 | A | 1/1999 | Cook et al. |
| 5,861,254 | A | 1/1999 | Schneider et al. |
| 5,861,501 | A | 1/1999 | Benseler et al. |
| 5,872,232 | A | 2/1999 | Cook et al. |
| 5,879,917 | A | 3/1999 | Essigmann et al. |
| 5,882,870 | A | 3/1999 | Nadeau |
| 5,882,941 | A | 3/1999 | Essigmann et al. |
| 5,891,689 | A | 4/1999 | Takle et al. |
| 5,935,776 | A | 8/1999 | Green et al. |
| 5,958,691 | A | 9/1999 | Pieken et al. |
| 5,989,823 | A | 11/1999 | Jayasena et al. |
| 6,001,820 | A | 12/1999 | Hirsh et al. |
| 6,004,746 | A | 12/1999 | Brent et al. |
| 6,005,087 | A | 12/1999 | Cook et al. |
| 6,011,020 | A | 1/2000 | Gold et al. |
| 6,051,388 | A | 4/2000 | Bodenhamer |
| 6,054,274 | A | 4/2000 | Sampson et al. |
| 6,060,056 | A | 5/2000 | Coutts et al. |

(Continued)

FOREIGN PATENT DOCUMENTS

| | | |
|---|---|---|
| EP | 0 593 901 A2 | 4/1994 |
| EP | 1 026 243 B1 | 8/2000 |
| JP | 11127864 | 5/1999 |
| WO | WO 92/14842 | 9/1992 |
| WO | WO 94/06811 | 3/1994 |
| WO | WO 94/08050 | 4/1994 |
| WO | WO 97/42317 | 11/1997 |
| WO | WO 99/33971 | 7/1999 |
| WO | WO 99/50462 | 10/1999 |
| WO | WO 00/20040 A1 | 4/2000 |
| WO | WO 00/22114 A1 | 4/2000 |

(Continued)

OTHER PUBLICATIONS

White et al. Surgical Forum, vol. 52:218-220, 2001.*
Sarraf-Yazdi et al., Journal of Surgical Research vol. 146:16-23, 2008.*
White et al., Angiogenesis vol. 11:395-401, 2008.*

(Continued)

*Primary Examiner*—Sean R McGarry
(74) *Attorney, Agent, or Firm*—King & Spalding LLP

(57) ABSTRACT

RNA aptamers and methods for identifying the same are disclosed. The RNA aptamers selectively bind coagulation factors, E2F family members, Ang1 or Ang2, and therapeutic and other uses for the RNA aptamers are also disclosed.

28 Claims, 30 Drawing Sheets

U.S. PATENT DOCUMENTS

| | | | |
|---|---|---|---|
| 6,083,696 | A | 7/2000 | Biesecker et al. |
| 6,093,555 | A | 7/2000 | Dudycz et al. |
| 6,110,462 | A | 8/2000 | Barbas et al. |
| 6,110,721 | A | 8/2000 | Gibbs et al. |
| 6,110,900 | A | 8/2000 | Gold et al. |
| 6,111,095 | A | 8/2000 | Benseler et al. |
| 6,114,038 | A | 9/2000 | Castro et al. |
| 6,117,557 | A | 9/2000 | Massie, II et al. |
| 6,120,997 | A | 9/2000 | Wong et al. |
| 6,127,119 | A | 10/2000 | Stephens et al. |
| 6,127,173 | A | 10/2000 | Eckstein et al. |
| 6,136,545 | A | 10/2000 | Hosel et al. |
| 6,147,204 | A | 11/2000 | Gold et al. |
| 6,150,461 | A | 11/2000 | Takei et al. |
| 6,153,410 | A | 11/2000 | Arnold et al. |
| 6,163,714 | A | 12/2000 | Stanley et al. |
| 6,171,795 | B1 | 1/2001 | Korman et al. |
| 6,177,263 | B1 | 1/2001 | Arnold et al. |
| 6,177,555 | B1 | 1/2001 | Jayasena et al. |
| 6,180,348 | B1 | 1/2001 | Li |
| 6,183,967 | B1 | 2/2001 | Jayasena et al. |
| 6,222,025 | B1 | 4/2001 | Cook et al. |
| 6,258,601 | B1 | 7/2001 | Monia et al. |
| 6,315,995 | B1 | 11/2001 | Pinsky |
| 6,316,198 | B1 | 11/2001 | Skouv et al. |
| 6,316,403 | B1 | 11/2001 | Pinsky |
| 6,331,398 | B1 | 12/2001 | Gold et al. |
| 6,344,321 | B1 | 2/2002 | Rabin et al. |
| 6,391,300 | B1 | 5/2002 | Rose |
| 6,531,584 | B1 | 3/2003 | Cook et al. |
| 2003/0083294 | A1 | 5/2003 | Sullenger et al. |
| 2006/0040881 | A1 | 2/2006 | Rusconi |

FOREIGN PATENT DOCUMENTS

| | | | |
|---|---|---|---|
| WO | WO 00/24912 | A1 | 5/2000 |
| WO | WO 00/42063 | A1 | 7/2000 |
| WO | WO 00/42064 | A1 | 8/2000 |
| WO | WO 00/47774 | A1 | 8/2000 |
| WO | WO 02/26932 | A2 | 4/2002 |
| WO | WO 02/096926 | A1 | 12/2002 |
| WO | WO 03/093422 | A2 | 11/2003 |
| WO | WO 2004/011680 | A2 | 2/2004 |
| WO | WO 2004/014844 | A2 | 2/2004 |
| WO | WO 2004/047742 | A2 | 6/2004 |
| WO | WO 2004/050899 | A2 | 6/2004 |
| WO | WO 2005/010150 | A2 | 2/2005 |
| WO | WO 2005/014533 | A2 | 2/2005 |
| WO | WO 2005/052121 | A2 | 6/2005 |
| WO | WO 2005/084412 | A2 | 9/2005 |
| WO | WO 2005/111238 | A2 | 11/2005 |
| WO | WO 2006/029258 | A2 | 3/2006 |
| WO | WO 2006/033854 | A2 | 3/2006 |

OTHER PUBLICATIONS

White et al., PNAS vol. 100(9):5028-5033, Apr. 11, 2003.*

Agrawal, S. et al., "Antisense therapeutics: Is it as simple as complementary base recognition?," *Mol. Med. Today*, 2000, vol. 6, pp. 72-81.

Aldaz-Caoll et al., "Apical Loop-Internal Loop Interactions: A New RNA-RNA Recognition Motif Identified through in Vitro Selection Against RNA Hairpins of the Hepatitis C Virus mRNA," *Biochemistry*, 2002, vol. 41, pp. 5883-5893.

Beigelman, L., et al., "Chemical modification of hammerhead ribozymes. Catalytic activity and nuclease resistance," *J. Biol. Chem.*, Oct. 25, 1995, vol. 270, No. 43, pp. 25702-25708.

Biedenkapp et al., "Viral myb Oncogene Encodes a Sequence-Specific DNA-Binding Activity," *Nature*, 1988, vol. 335, pp. 835-837.

Biesecket et al., "Derivation of RNA Aptamer Inhibitors of Human Complement C5," *Immunopharmacology*, 1999, vol. 42, pp. 219-230 (abstract).

Black, A.R., and Azizkhan-Clifford, J., "Regulation of E2F: a family of transcription factors involved in proliferation control," *Gene*, Sep. 17, 1999, vol. 237, No. 2, pp. 281-302.

Boiziau, C. et al., "DNA Aptamers Selected Against the HIV-1 *Trans*-Activation-responsive RNA Element Form RNA-DNA Kissing Complexes," *The Journal of Biological Chemistry*, 1999, vol. 274, No. 18, pp. 12730-12737.

Burke, et al., "A Novel Acidophilic RNA Motif that Recognizes Coenzyme A," *Biochemistry*, Nov. 25, 1997, pp. 4653-4663.

Callas et al., "Comparative Pharmacology of Site Directed Antithrombin Agents Implication in Drug Development," *Thrombosis and Haemostasis*, 1995, vol. 74, pp. 473-481 (abstract).

Charlton et al., "In vivo Imaging of Inflammation Using an Aptamer Inhibitor of Human Neutrophilelastase," *Chem. Biol.*, 1997, vol. 4, pp. 809-816 (abstract).

Chase. J.W., and Williams, K.R., "Single-stranded DNA binding proteins required for DNA replication," *Annu. Rev. Biochem.*, 1986, vol. 55, pp. 103-136.

Collin et al., "NMR Characterization of a Kissing Complex Formed Between the TAR RNA Element of HIV 1 and a DNA Aptamer," *Nucl. Ac. Rsch.*, 2000, vol. 28, pp. 3386-3391.

Dale, R.M., et al., "Direct covalent mercuration of nucleotides and polynucleotides," *Biochemistry*, Jun. 3, 1975, vol. 14, No. 11, pp. 2447-2457.

Darfeuille et al., "RNA and N3'-P5' Kissing Aptamers Targeted to the trans-Activation-responsive (TAR) RNA of the Human Immunodeficiency Virus-1," *Nucs Nuc. Nuc. Ac.*, 2001, vol. 20, pp. 441-449 (abstract).

Davies, J., et al., Chap. 8, p. 185, in *RNA World*, 1993, Cold Spring Harbor Laboratory Press; eds. Gestlaad and Atkins.

DeAnda, A. Jr., et al., "Pilot study of the efficacy of a thrombin inhibitor for use during cardiopulmonary bypass," *Ann. Thorac. Surg.*, Aug. 1994, vol. 58, No. 2, pp. 344-350.

Duconge et al., "Is Closing "GA PAI" a Rule for Stable Loop-Loop RNA Complexes?," *J. Biol. Chem.*, 2000, vol. 275, pp. 21287-21294.

Eichorn, G.I., et al., "Interaction of metal ions with polynucleotides and related compounds. XII. The relative effect of various metal ions on DNA helicity," *J. Am. Chem. Soc.*, Dec. 18, 1968, vol. 90, No. 26, pp. 7323-7328.

Ellington et al., "Selection of RNAs with Ligand-Specific Binding Activity from Pools of Random Sequence Molecules," May 16-20, 1990, Cold Spring Harbor "RNA Processing" Conference.

Feuerstein, G.Z., et al., "Antithrombotic efficacy of a novel murine antihuman factor IX antibody in rats," *Arterioscler. Thromb. Vasc. Biol.*, Oct. 1999, vol. 19, No. 10, pp. 2554-2562.

Gal et al., "Selection of a RNA Aptamer that Binds to Human Activated Protein C and Inhibits its Protease Function," *European J. Biochem.*, 1998, vol. 252, pp. 553-562 (abstract).

Good, P.D., et al., "Expression of small, therapeutic RNAs in human cell nuclei," *Gene Ther.*, Jan. 1997, vol. 4, No. 1, pp. 45-54.

Griffin, L.C., et al., "In vivo anticoagulant properties of a novel nucleotide-based thrombin inhibitor and demonstration of regional anticoagulation in extracorporeal circuits," *Blood*, Jun. 15, 1993, vol. 81, No. 12, pp. 3271-3276.

Harbour, J.W., and Dean, D.C., "The Rb/E2F pathway: expanding roles and emerging paradigms," *Genes Dev.*, Oct. 1, 2000, Vo.. 14, No. 19, pp. 2393-2409.

Helin, K., and Ed, H., "The retinoblastoma protein as a transcriptional repressor," *Trends Cell Biol.*, Feb. 1993, Vo. 3, No. 2, pp. 43-46.

Hunter, T., "Breaking the cycle." *Cell*, 1993, Vo. 75, No. 5, pp. 839-841.

Hwang, S. et al., "Inhibition of Gene Expression in Human Cells Through Small Molecule—RNA Interactions," *PNAS*, 1999, vol. 96, p. 12997-13002.

Ishizaki, J., et al., "Inhibition of cell proliferation by an RNA ligand that selectively blocks E2F function," *Nature Med.*, Dec. 1996, vol. 2, No. 12, pp. 1386-1389.

Jen et al., "Suppression of gene expression by targeted disruption of messenger RNA: available options and current strategies," *Stem Cells*, 2000, vol. 18, pp. 307-319.

Kinzler et al., "Whole Genome PCR: Application to the Identification of Sequences Bound by Gene Regulatory Proteins," *Nuc. Acids Rsch*, 1989, vol. 17, p. 3645-3653.

La Thangue, N.B., "DRTF1/E2F: an expanding family of heterodimeric transcription factors implicated in cell-cycle control," *Trends Biochem. Sci.*, Mar. 1994, vol. 19, No. 3, pp. 108-114.
Leclerc et al., Abstract of "A Three-Dimensional Model of the Rev-binding Element of HIV-a Derived from Analyses of Aptamers." *Nat. Struct. Biol.*, 1994, pp. 293-300.
Lee, S.W., et al., "Isolation of a nuclease-resistant decoy RNA that can protect human acetylcholine receptors from myasthenic antibodies," *Nature Biotechnol.*, Jan. 1997, vol. 15, No. 1, pp. 41-45.
Leva et al., "GnRH Binding RNA and DNA Spielgelmers a Novel Approach Toward GnRH Antagonism," *Chemistry & Biology*, 2002, vol. 8, pp. 351-359.
Li et al., "A Novel Nucleotide Based Thrombin Inhibitor Inhibits Clot Bound Thrombin and Reduces Arterial Platelet Thrombus Formation," *Blood*, 1994, vol. 83, pp. 677-682 (abstract).
Lippard, S.J., et al., "Platinum complexes: probes of polynucleotide structure and antitumor drugs," *Acc. Chem. Res.*, 1978, vol. 11, pp. 211-217.
Mann, K.G., et al., "Surface-dependent reactions of the vitamin K-dependent enzyme complexes," *Blood*, Jul. 1, 1990, vol. 76, No. 1, pp. 1-16.
Nevins, J.R., "E2F: a link between the Rb tumor suppressor protein and viral oncoproteins," *Science*, Oct. 16, 1992, vol. 258, No. 5081, pp. 424-429.
Oliphant et al., "Defining the Sequence Specificity of DNA-Binding Proteins by Selecting Binding Sites from Random-Sequence Oligonucleotides: Analysis of Yeast GCN4 Protein," *Mol. Cell. Bio.* 1989, vol. 9, pp. 2944-2949.
Opalinska et al., "Nucleic-Acid Therapeutics: Basic Principles and Recent Applications," *Nature Reviews Drug Discovery*, 2002, vol. 1, pp. 503-514.
Padmanabhan et al., "The Structure of Alpha Thrombin Inhibited by a I5mer Single Stranded DNA Aptamer," *JBC*, 1993, vol. 268, pp. 17651-17654 (abstract).
Pieken, W.A., et al., "Kinetic Characterization of Ribonuclease-Resistant 2'-Modified Hammerhead Ribozymes," *Science*, Jul. 19, 1991, vol. 253, No. 5017, pp. 314-317.
Robertson et al., Selection in Vitro of an RNA Enzyme that Specifically Cleaves Single-Stranded DNA, *Nature*, Mar. 29, 1990, vol. 344, pp. 467-468.
Rusconi, C., et al., "Blocking the initiation of coagulation by RNA aptamers to factor VIIa," *Thrombosis and Haemostasis*, Nov. 2000, vol. 84, No. 5, pp. 841-848.
Rusconi, C. et al., "RNA Aptamers as Reversible Antagonists of Coagulation Factor IXa," *Nature*, 2002, vol. 419, pp. 90-94.
Shaw et al., "A Novel Oligodeoxynucleotide Inhibitor of Thrombin 1. In vitro Metabolic Stability in Plasma and Seum," *Pharm. Rsch.*, 1995, vol. 12, pp. 1937-1942 (abstract).
Sheehan et al., Phosophothioate Oligonucleotides Inhibit the Intrinsic Tenase Complex, *Blood*, 1998, vol. 92, No. 5, pp, 1617-1625.
Sherr, C.J., "Mammalian GI Cyclins," *Cell*, Jun. 18, 1993, vol. 73, No. 6, pp. 1059-1065.
Sherr, C.J. et al., "Inhibitors of Mammalian GI Cyclin-Dependent Kinases," *Genes Dev.*, May 15, 1995, vol. 9, No. 10, pp. 1149-1163.
Smirnov, I. et al., "Effect of Loop Sequence and Size on DNA Aptamer Stability," *Biochemistry*, Feb. 15, 2000, vol. 39, No. 6, pp. 1462-1468.
Sullenger, B.A., et al., "Overexpression of TAR Sequences Renders Cells Resistant to Human Immunodeficiency Virus Replication," *Cell*, Nov. 2, 1990, vol. 63, No. 3, pp. 601-608.
Szostak et al., "Structure and Activity Ribozymes: Redesigning the Molecules of Life," Conference of International Symposium on Bioorganic Chemistry, Interlaken, May 4-6, 1988.
Tasset et al., "Oligonucleotide Inhibitors of Human Thrombicin that Bind Distinct Epitopes," *J. Molecular Biol.*, 1997, vol. 272, pp. 688-698 (abstract).
Tinevez et al., "Selective Inhibition of Cell-Free Translation by Oligonucleotides Targeted to a mRNA Hairpin Structure," *Nucl. Ac. Rsch.*, 1998, vol. 26, pp. 2273-2278.
Tucker, C.E., et al., "Detection and Plasma Pharmacokinetics of an Anti-Vascular Endothelial Growth Factor Oligonucleotide-Aptamer (NX1838) in Rhesus Monkeys," *J. Chromotog.*, Sep. 10, 1999, vol. 732, No. 1, pp. 203-212.
Wahlestedt et al., "Potent and Nontoxic Antisense Oligonucleotides Containing Locked Nucleic Acids," *PNAS*, 2000, vol. 97, pp. 5633-5638.
Weinberg, R.A., "The retinoblastoma protein and cell cycle control," *Cell*, May 5, 1995, vol. 81, No. 3, pp. 323-330.
Werstuck et al., "Controlling Gene Expression in Living Cells through Small Molecule-RNA Interactions," *Science*, Oct. 9, 1998, vol. 282. pp. 296-298.
White, R.R., et al., "Developing aptamers into therapeutics," *J. Clin. Invest.*, Oct. 2000, vol. 106, No. 8, pp. 929-934.
Williams et al., "Bioactive and Nuclease Resistant L-DNA Ligand of Vasopressin," *PNAS*, 1997, vol. 94, pp. 11285-11290.
Willis, M.C., et al., "Liposome-anchored vascular endothelial growth factor aptamers," *Bioconjug. Chem.*, Sep.-Oct. 1998, vol. 9, No. 5, pp. 573-582.
Feigon, J. et al., "Aptamer Structures from A to ζ," *Chemistry & Biology*, 1996, pp. 611-617, vol. 3.
Kubik, M. et al., "High-Affinity RNA Ligands to Human α-Thrombin," *Nucleic Acids Research*, 1994, pp. 2619-2626, vol. 22, No. 13.
Rusconi, C. et al., "Blocking the Initiation of Coagulation by RNA Aptamers to Factor VIIa," *Thromb Haemost*, 2000, vol. 84, No. 5, pp. 841-848.
White, R. et al., "A Novel Inhibitor of Antgiopoietin-1 Blocks Tie2 Signaling," *Surgical Forum*, 2001, pp. 218-220, vol. 52.

* cited by examiner 9.1 (SEQ ID NO:1) : 5' GGGAGAGAGG AAGAGGGAUG GG CCGCCAGU GGGAAGCUAU ACCCAACGCC CCAGCCCCAG AGCAUAACCC AGAGGUCGAU AGUACUGGAU CCCCCC 3'

9.2 (SEQ ID NO:2) : 5' GGGAGAGAGG AAGAGGGAUG GGCUAUAUAC ACGCUGGUGA UCCCAUCUCA AUUGAAACAA CACAUAACCC AGAGGUCGAU AGUACUGGAU CCCCCC 3'

9.3 (SEQ ID NO:3) : 5' GGGAGAGAGG AAGAGGGAUG GGGACUAUAC CGCGUAAUGC UGCCUCCCCA UUCCGGAACG CUCAUAACCC AGAGGUCGAU AGUACUGGAU CCCCCC 3'

9.4 (SEQ ID NO:4) : 5' GGGAGAGAGG AAGAGGGAUG GGCACUAUAC GCAUCUUGCU GCCUGCCCGC GAGUCAAAUU GCAUAACCCA GAGGUCGAUA GUACUGGAUC CCCCC 3'

9.5 (SEQ ID NO:5) : 5' GGGAGAGAGG AAGAGGGAUG GGCCUACCAG UUCGUGGCUA GCGUGACGUA CCACCCAGGG ACCAUAACCC AGAGGUCGAU AGUACUGGAU CCCCCC 3'

9.7 (SEQ ID NO:6) : 5' GGGAGAGAGG AAGAGGGAUG GGCGAUAACC AACAUGGUGA UCCCAUUCAU CAUACCCUAC AACAUAACCC AGAGGUCGAU AGUACUGGAU CCCCCC 3'

9.8 (SEQ ID NO:7) : 5' GGGAGAGAGG AAGAGGGAUG GGGCCACCUA CUAUACCGGU CAUCGUGCAU AGGUCGCUGC CACAUAACCC AGAGGUCGAU AGUACUGGAU CCCCCC 3'

9.9 (SEQ ID NO:8) : 5' GGGAGAGAGG AAGAGGGAUG GGUCUCACAC CCGAAGAUGG CCAAAGAGGG AGAUGAGUUU CCAUAACCCA GAGGUCGAUA GUACUGGAUC CCCCC 3'

9.11 (SEQ ID NO:9) : 5' GGGAGAGAGG AAGAGGGAUG GGACUAUAUU CGGAAUCUGG ACUCCCACCU GCCUGCCCCA GACAUAACCC AGAGGUCGAU AGUACUGGAU CCCCCC 3'

9.12 (SEQ ID NO:10) : 5' GGGAGAGAGG AAGAGGGAUG GGCGAUAUAC ACAUUGGUGA UCCCACCCAC AUGAAACCAC AGCAUAACCC AGAGGUCGAU AGUACUGGAU CCCCCC 3'

9.13 (SEQ ID NO:11) : 5' GGGAGAGAGG AAGAGGGAUG GGCUCAUCAC AGGCGAAGUG AACAACACUA CCGNCNAGUU ACCAUAACCC AGAGGUCGAU AGUACUGGAU CCCCCC 3'

9.14 (SEQ ID NO:12) : 5' GGGAGAGAGG AAGAGGGAUG GG GACUAUAC GUGAACGACU GCAUCCACUUC CCcGCCAUGG CAUAACCCAG AGGUCGAUAG UACUGGAUCC CCCC 3'

FIG.1A 9.16 (SEQ ID NO:13) : 5' GGGAGAGAGG AAGAGGGAUG GGCCAUACGU GGACGACUGC ACCCGACCCU UCAGCCCAGG UCCAUAACCC AGAGGUCGAU AGUACUGGAU CCCCCC 3'

9.17 (SEQ ID NO:14) : 5' GGGAGAGAGG AAGAGGGAUG GGACCAUACG CACAUUGCUG AAUCCCCcUC AAUAGCACCU ACCAUAACCC AGAGGUCGAU AGUACUGGAU CCCCCC 3'

9.18 (SEQ ID NO:15) : 5' GGGAGAGAGG AAGAGGGAUG GGCCAUAACC ACUUUGGUGA ACCCACCCAG CUCc/UUGUGAU UGCAUAACCC AGAGGUCGAU AGUACUGGAU CCCCCC 3'

9.19 (SEQ ID NO:16) : 5' GGGAGAGAGG AAGAGGGAUG GGACCAUAAC GACUACUCGUGA AUCCCACCAU CAGCGCACAA CAUAACCCAGA GGUCGAUAG UACUGGAUCC CCCC 3'

9.20 (SEQ ID NO:17) : 5' GGGAGAGAGG AAGAGGGAUG GGGACUAUAC CGGCAAUCGU GCAUCCCCUG GACCUAACAA UACAUAACCC AGAGGUCGAU AGUACUGGAU CCCCCC 3'

9.21 (SEQ ID NO:18) : 5' GGGAGAGAGG AAGAGGGAUG GG AACACCAU UAAUGCUCGG CCAGGUAACC CCGGCGCAUA CUCAUAACCC AGAGGUCGAU AGUACUGGAU CCCCCC 3'

9.25 (SEQ ID NO:19) : 5' GGGAGAGAGG AAGAGGGAUG GGGACCAUAA CUCUAACGGG UGAAUCCCGC AUCUCGACAA UACAUAACCC AGAGGUCGAU AGUACUGGAU CCCCCC 3'

9.26 (SEQ ID NO:20) : 5' GGGAGAGAGG AAGAGGGAUG GG UGAUAACC ACUCUGGUGA ACCCCUCCCG ACUUGCUCGC ACAUAACCCA GAGGUCGAUA GUACUGGAUC CCCCCC 3'

9.27 (SEQ ID NO:21) : 5' GGGAGAGAGG AAGAGGGAUG GGUAAUAACU GUAUGGUGAA CCCACCCAAA CUCCCAUGGC UACAUAACCC AGAGGUCGAU AGUACUGGAU CCCCCC 3'

9.28 (SEQ ID NO:22) : 5' GGGAGAGAGG AAGAGGGAUG GG CGCCAUAC GCACAUUGCU GCAUCGCCUU CCCGUAAGAA CCAUAACCCA GAGGUCGAUA GUACUGGAUC CCCCC 3'

FIG.1B 10.1 (SEQ ID NO:23) : 5' GGGAGAGAGG AAGAGGGAUG GGAAAAUAGC CCCAGCGAGA UAAUACUUGG CCCCCGUACCA CCAUAACCCA GAGGUCGAUA GUACUGGAUC CCCCC 3'

10.5 (SEQ ID NO:24) : 5' GGGAGAGAGG AAGAGGGAUG GGCCAGAAGG AACUAAACAC CUGAACCCCC CAUCGCGAGAG ACCAUAACCC AGAGGUCGAU AGUACUGGAU CCCCCC 3'

10.6 (SEQ ID NO:25) : 5' GGGAGAGAGG AAGAGGGAUG GGAUGUCACU UGGCCCCUCG CGCACc/aCGCC AGCGAGCCCA UAACCCAGAG GUCGAUAGUA CUGGAUCCCC CC 3'

10.7 (SEQ ID NO:26) : 5' GGGAGAGAGG AAGAGGGAUG GGACACGCCC AGCGAGCUCA AACUUGGCCC CCGUGCAUCA CC CCAUAACC CAGAGGUCGA UAGUACUGGA UCCCCCC 3'

10.8 (SEQ ID NO:27) : 5' GGGAGAGAGG AAGAGGGAUG GGAAGUGCCA CAGCGAGCAC AUGACUUGGC CCCGCAUUGC ACCCAUAACC CAGAGGUCGA UAGUACUGGA UCCCCCC 3'

10.11 (SEQ ID NO:28) : 5' GGGAGAGAGG AAGAGGGAUG GGAAACUAAU GCCCUAGCGA GCAUACCCGG ACUGGCCCCG CCAUAACCC AGAGGUCGAU AGUACUGGAU CCCCCC 3'

10.12 (SEQ ID NO:29) : 5' GGGAGAGAGG AAGAGGGAUG GGAAAAUAGC CCCAGCGAGA UAAUACUUGG CCCCGCUACU ACCCAUAACC CAGAGGUCGA UAGUACUGGA UCCCCCC 3'

10.13 (SEQ ID NO:30) : 5' GGGAGAGAGG AAGAGGGAUG GGCGACCCCA CUGGCGGAAA CCGACAAUCA CUCCCCACGA CCAUAACCC AGAGGUCGAU AGUACUGGAU CCCCCC 3'

10.14 (SEQ ID NO:73) : 5' GGGAGAGAGG AAGAGGGAUG GGAAAAUAGC CCCAGCGAGA UAAUACUUGG CCCCGCUACU ACCAUAACCC AGAGGUCGAU AGUACUGGAU CC 3'

FIG.6A

10.15 (SEQ ID NO:31) : 5' GGGAGAGAGG AAGAGGGAUG GGCAGCCCAG CGAGGGACAC UUAACCCCCU GUCCCCCAUC CAAACCAUAA CCCAGAGGUC GAUAGUACUG GAUCCCCCC 3'

10.18 (SEQ ID NO:32) : 5' GGGAGAGAGG AAGAGGGAUG GGCCAGAAGU CACCGCGACG GUACUGAACC CCCCACCCAA ACCCAUAACC CAGAGGUCGA UAGUACUGGA UCCCCCC 3'

10.19 (SEQ ID NO:33) : 5' GGGAGAGAGG AAGAGGGAUG GGCCAGAAGU GCUCACUACA ACGCUUUGAC CCCCCCAUCC ACAUCCCAUA ACCCAGAGGU CGAUAGUACU GGAUCCCCCC 3'

10.21 (SEQ ID NO:34) : 5' GGGAGAGAGG AAGAGGGAUG GG CCAGCAAC CGAAGGGCGG AAUACCCCCC GUCUCCACAU ACCCAUAACC CAGAGGUCGA UAGUACUGGA UCCCCCC 3'

10.22 (SEQ ID NO:35) : 5' GGGAGAGAGG AAGAGGGAUG GG ACGCGACU CAGGCAGCAC UUGACUUGGC CCCUUGCGAU CACCAUAACC CAGAGGUCGA UAGUACUGGA UCCCCCC 3'

10.23 (SEQ ID NO:36) : 5' GGGAGAGAGG AAGAGGGAUG GG CCAGCAAC GCUAACACGG AAUACCCCCC ACCCCAACGU GCCCAUAACC CAGAGGUCGA UAGUACUGGA UCCCCCC 3'

10.24 (SEQ ID NO:37) : 5' GGGAGAGAGG AAGAGGGAUG GG CUUCUCAA CCGAAAUACA ACUUUAAAUC AUUUAUCACU UACCAUAACC CAGAGGUCGA UAGUACUGGA UCCCCCC 3'

10.30 (SEQ ID NO:38) : 5' GGGAGAGAGG AAGAGGGAUG GGAUACGCCG AUGCAAGCAU GUCCACACAC CGCAUGCCGU ACCCAUAACC CAGAGGUCGA UAGUACUGGA UCCCCCC 3'

FIG.6B

16.1 (SEQ ID NO:39) : 5' GGGAGAGAGG AAGAGGGAUG GGUACAGAGG AGUACAAGUA GCAUGGUCCC CUCGUGUAAA AACAUAACCC AGAGGUCGAU AGUACUGGAU CCCCCC 3'

16.2 (SEQ ID NO:40) : 5' GGGAGAGAGG AAGAGGGAUG GGUGCAAAAG AGCUUCUUGU AGUAUGAUCC CUCAACCGCA AGCAUAACCC AGAGGUCGAU AGUACUGGAU CCCCCC 3'

16.3 (SEQ ID NO:41) : 5' GGGAGAGAGG AAGAGGGAUG GG UACAGAGG AGUACAAGUA GCAUGAUCCC CUCGUGUAAA AACAUAACCC AGAGGUCGAU AGUACUGGAU CCCCCC 3'

16.5 (SEQ ID NO:42) : 5' GGGAGAGAGG AAGAGGGAUG GGAGCCUAUG UAACAGAUGC AGAUCCCUAG UCGUCCCAAC ACCAUAACCC AGAGGUCGAU AGUACUGGAU CCCCCC 3'

16.7 (SEQ ID NO:43) : 5' GGGAGAGAGG AAGAGGGAUG GGCACAACGA ACACCGCAUC CCUUGACAGA AAGAGCACGC CUCAUAACCC AGAGGUCGAU AGUACUGGAU CCCCCC 3'

16.10 (SEQ ID NO:44) : 5' GGGAGAGAGG AAGAGGGAUG GGUACAGAGG AGUACAAGUA ACAUGAUCCC CUCGUGUAAA AACAUAACCC AGAGGUCGAU AGUACUGGAU CCCCCC 3'

16.11 (SEQ ID NO:45) : 5' GGGAGAGAGG AAGAGGGAUG GG CACAACGA ACACCGCAUC CCUUGACAGA AAGAACACGC CUCAUAACCC AGAGGUCGAU AGUACUGGAU CCCCCC 3'

16.18 (SEQ ID NO:46) : 5' GGGAGAGAGG AAGAGGGAUG GGCACAAGGA ACACCGCAUC CCUUGACAGA AAGAACACGC CUCAUAACCC AGAGGUCGAU AGUACUGGAU CCCCCC 3'

16.20 (SEQ ID NO:47) : 5' GGGAGAGAGG AAGAGGGAUG GGAGCCUAUG UAACAGAUGC AGAUCCCUAG ACGACCCAAC ACCAUAACCC AGAGGUCGAU AGUACUGGAU CCCCCC 3'

FIG.10

| Random region sequences (Round 13) | Kd Human Thrombin | Kd Porcine Thrombin |
|---|---|---|
| PIG 5<br>UGCG*AACAAAGCUGAAGUACUU*ACGCACAACCCGUAGAAU | 3 nM | 1 nM |
| PIG 7<br>*AACAACUGAAGAACUACCC*UUCUUACUGACGAAUUAA | 1 nM | <0.5 nM |
| PIG 8<br>*AAACAAAGCUGAAGUACUU*AUUCCAUCACCACGCCGGAA | 1 nM | 0.5 nM |
| PIG 10<br>UAUUUGGCUUCUCAGUGCCGCAGAGACAGCAACAAUUAGU | >>50 nM | 0.5 nM |
| HUMAN<br>*ACAAAGCUGGAGAACUU*ACCGUUCCCUCUCCAGAGAUCAA | 2 nM | 0.5 nM |
| TOGGLE 25<br>G*AACAAAGCUGAAGUACUU*ACCCAAGAUCAUCCCGAACGA | 5 nM | 0.5 nM |
| TOGGLE 30<br>*AACAAAGCUGGAGAACUU*AACGUCCCUCUCCCAGCGGUAA | 3 nM | 0.5 nM |

FIG.11

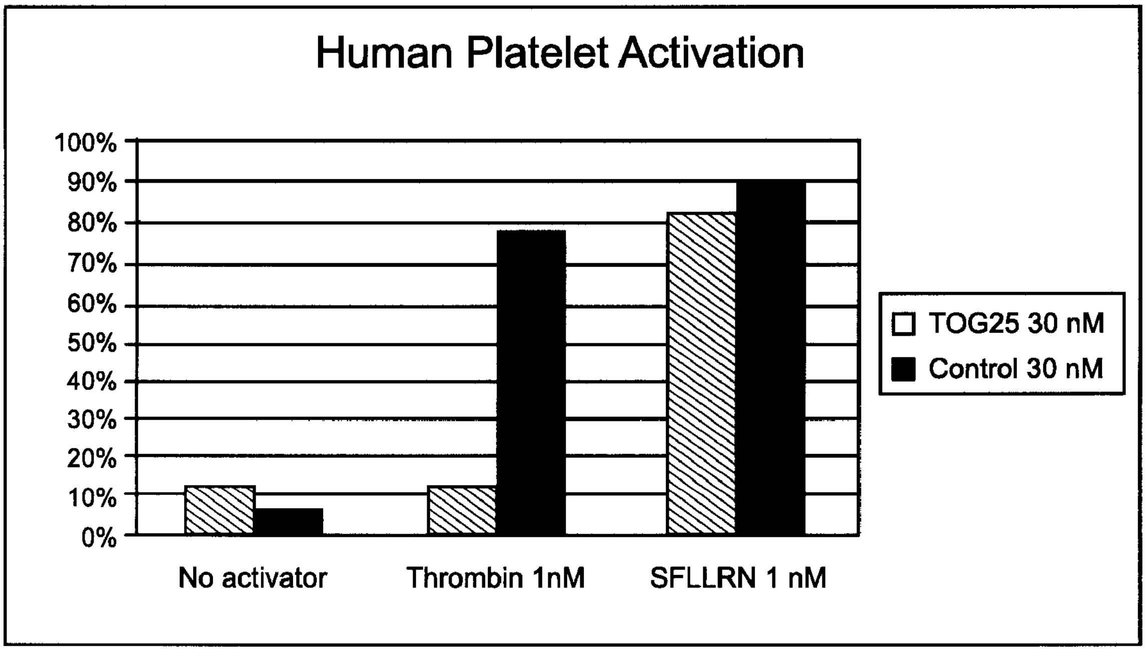

FIG.12

E2F-3 Round 10 Aptamers

5' Primer GGG AGA GAG GAA GAG GGA UGG G (SEQ ID NO: 62)

3' Primer C AUA ACC CAG AGG UCG A A GUA CUG GAU CCC CCC (SEQ ID NO: 63)

10-1 AND 10-8 (SEQ ID NO: 64)
5' P-AAU GGA AUC ACU GAA GGC CCU CCG UAG CAC CUA ACA CAG U-3' P 10-2 (SEQ ID NO: 65)
5' P-GCA UCC UGC CAG CGG CGA CGG ACC UUC GCC CAC AGG CCU C-3' P 10-3, 10-7, 10-11, AND 10-12 (SEQ ID NO: 66)
5' P-UUA UA AGC ACA CUG AAG CCC UCA GCA AAA CCU CCA CAG G-3' P 10-4 (SEQ ID NO: 67)
5' P-UAU GAA AUC ACA GAA GCC CGC GUU CGA CAC CUC CAC UGU U-3' P 10-5 (SEQ ID NO: 68)
5' P-CAA ACU CAC AGA CUC CAA CUG CAG GAG CAC CCA CCC ACA CUG GGA CAG-3' P 10-6 (SEQ ID NO: 69)
5' P-AUC CCC GCC GUA AGC CGU CCU GAU GGA CAC CAC ACU CCG C-3' P

FIG.17

| | | S1 → | L1 | S2 → | L2 | ← S2 | L3 | ← S1 | Seq. ID. |
|---|---|---|---|---|---|---|---|---|---|
| *9-3 | 5' | gggaugggGA | CUAUACC | GCG | UAAUGC | UGC | C | UCCCCAUUCC | 228 |
| *9-20 | 5' | augggGA | CUAUACCG | GCA | AUCG | UGC | A | UCCCCU | 229 |
| *9-25 | 5' | gggaugggGA | CCAUA | ACUC | UAAC | GGGU | GAA | UCCCGCAUCU | 230 |
| *9-26 | 5' | gggauggg | UGAUA | ACCA | CUC | UGGU | GAA | CCCCUCCC | 231 |
| *9-28 | 5' | gggaugggCG | CCAUAC | GCA | CAU | UGC | UGCAU | CGCCUUCCC | 232 |
| *9-19 | 5' | gagggaugggA | CCAUA | ACGA | CUAC | UCGU | GAA | UCCCACCAUC | 233 |
| *9-17 | 5' | gagggaugggA | CCAUAC | GCA | CAU | UGC | UGAA | UCCCCCUC | 234 |
| *9-11 | 5' | gggaugggA | CUAUA | UUCGG | AAU | CUGGA | C | UCCCACCU | 235 |
| *9-4 | 5' | gggaugggC | ACUAUAC | GCA | UCU | UGC | U | GCCUGCCC | 236 |
| *9-16 | 5' | agggauggg | CCAUA | CGU | GG | ACG | ACUGCA | CCCGACCCU | 237 |
| *9-18 | 5' | gggauggg | CCAUA | ACCA | CUU | UGGU | GAA | CCCACCCA | 238 |
| *9-7 | 5' | ggauggg | CGAUA | ACCA | ACA | UGGU | GAU | CCCAUUC | 239 |
| *9-12 | 5' | gggauggg | CGAUA | UAC | ACAUUG | GUG | AU | CCCACCC | 240 |
| *9-2 | 5' | gggauggg | CUAUAUA | CAC | GCUG | GUG | AU | CCCAUCUC | 241 |
| *9-14 | 5' | gggaugggGA | CUAUA | CGU | GAACG | ACU | GCA | UCCACUUCCC | 242 |
| *9-27 | 5' | gggauggg | UAAUA | ACU | GUA | UGG | UGAA | CCCACCC | 243 |

FIG.18

Seq. ID. No. 187 dG = -1.43 [initially -4.2] ANG11-1.41

RNA APTAMERS AND METHODS FOR IDENTIFYING THE SAME

CROSS REFERENCE TO RELATED APPLICATIONS

This application is a divisional of U.S. patent application Ser. No. 09/963,827 filed Sep. 26, 2001 now U.S. Pat. No. 7,312,325, allowed, which claims priority to U.S. Provisional Application Ser. No. 60/235,654, filed Sep. 26, 2000, herein incorporated by reference in its entirety.

GRANT STATEMENT

This work was supported by grants R01 HL57606 and R01 CA79983 from the National Institutions of Health (NIH), and by grant SPS #1805 from the Jane Coffin Childs Foundation. Thus, the United States Government has certain rights in the invention.

TECHNICAL FIELD

The present invention relates generally to compositions and methods for identifying oligonucleotide sequences that specifically bind biomolecules, including peptides, hydrophobic molecules, and target features on cell surfaces, in particular extracellular proteins, and the use of these sequences to detect and/or isolate the target molecules and the resulting compositions. The instant invention is exemplified by obtaining compositions, through the use of disclosed methods, that comprise oligonucleotide sequences that bind to coagulation factors, E2F family transcription factors, Ang1, Ang2, and fragments or peptides thereof. Even more particularly, the present invention is directed towards ribonucleic acid (RNA) aptamers, and to methods of identifying them.

TABLE OF ABBREVIATIONS

I-XII . . . coagulation factors
a . . . activated, as in factor VIIa, IXa, Xa, etc.
ACT . . . activated clotting time
Ang1 . . . Angiopoietin-1
Ang1* . . . activated Angiopoietin-1
Ang2 . . . Angiopoietin-2
Ang2* . . . activated Angiopoietin-2
aPTT . . . Activated Partial Thromboplastin Time
DNA . . . deoxyribonucleic acid
DP . . . diphosphate
FB . . . fraction bound
GTP . . . guanidine triphosphate
$K_d$ . . . dissociation constant
M7G . . . 5-adenosyl-L-methonine substituted GTP
MP . . . monophosphate
nM . . . nanomolar
PAC . . . phenoxyacetyl
pM . . . picomolar
PT . . . Prothrombin Time
RNA . . . ribonucleic acid
SELEX . . . Systematic Evolution of Ligands by EXponential Enrichment
sem . . . standard error for mean
TAC . . . t-butoxyacetyl
TOG . . . toggle
TP . . . triphosphate

BACKGROUND ART

Thrombin belongs to the group of serine proteases and plays a central part in the blood coagulation cascade as terminal enzyme. Both the intrinsic and the extrinsic coagulation cascade lead, via a plurality of amplifying stages, to the production of thrombin from prothrombin. Thrombin-catalyzed cleavage of fibrinogen to fibrin then initiates blood coagulation and aggregation of platelets that, in turn, due to the binding of platelet factor 3 and coagulation factor XIII and a large number of highly active mediators, enhance thrombin formation.

To elaborate, the mechanism of blood coagulation normally occurs in a cascade of two possible routes. One of the routes, the extrinsic blood coagulation, starts with the liberation of thromboplastin and the activation of factor VII. Activated factor VII (i.e. factor VIIa) in turn activates factor X, followed by an activation of factor V and factor II (prothrombin). Factor IIa (thrombin) converts fibrinogen into fibrin at the end of the cascade.

The other route, the intrinsic blood coagulation, occurs via an activation of factor XII by contact with and subsequent activation of factor XI, factor IX and factor X in the presence of calcium and factor VIII, followed by an activation of thrombin (factor II) to activated thrombin (factor IIa) which triggers coagulation by cleaving fibrinogen to fibrin. Thus, activated thrombin (factor IIa) plays a role in both routes of the blood coagulation cascade.

Hitherto, there has been an intensive search for anticoagulants that can particularly be utilized in the treatment of cardiovascular disease, e g. septic shock, thromboses, embolisms, atherosclerosis and cardiac infarctions, furthermore in case of blood transfusions or following surgery. One method of suppressing the coagulation of blood is the direct administration of substances that modulate thrombin or other coagulation factors. The identification of such substances thus represents a long-felt and ongoing need in the art.

E2F refers to a family of transcription factors (also referred to herein as the "E2F family", which includes but is not limited to E2F-1, E2F-2, E2F-3, E2-F4, E2-F5 and E2-F6), and E2F activity is plays a role in a wide variety of proliferative events. E2F activity is controlled as the end result of $G_1$ cyclin dependent kinase regulatory cascades that involve the Rb family of proteins. See, e.g., Sherr, C. J., *Cell,* 73:1059-1065 (1993); Hunter, T., *Cell* 75:839-841 (1993); Nevins J. R., *Science,* 258:424-429 (1992); Helin, K. and Harlow, E., *Trends Cell Biol.* 3:43-46 (1993); La Thangue, N. B., *Trends Biochem. Sci.* 19:180-114 (1994); Sherr, C. J.; Roberts, J. M., *Genes Dev.* 9:1149-1143 (1995); Weinberg, R. A. *Cell* 81:323-330 (1995); Harbour, J. W. and Dean, D. C., *Genes and Development* 14:2393-2409 (2000); and Black, A. R. and Azizkhan-Clifford, J., *Gene* 237:281-302 (1999). Thus, ligands that selectively bind to an E2F family member would play a role in the control of cell proliferation, which is of central importance to the proper development of a multicellular organism, the homeostatic maintenance of tissues, and the ability of certain cell types to respond appropriately to environmental cues.

Tie2 is an endothelial receptor tyrosine kinase (RTK) that is required for both embryonic vascular development and pathological angiogenesis. Tie2 is unique among RTKs in that it has two ligands with apparently opposing actions. Angiopoietin-1 (Ang1) is an activating ligand while Angiopoietin-2 (Ang2) is thought to be a naturally occurring antagonist for Tie2. Mice lacking Tie2 or Ang1 die midway through gestation due to abnormalities of vascular morphogenesis characterized by deficient recruitment of supporting smooth muscle cells and pericytes. Moreover, Ang1 promotes endothelial cell survival and blocks the increases in vascular permeability induced by vascular endothelial growth factor (VEGF), supporting a role for Ang1 in the stabilization and maintenance of the adult vasculature. In contrast, Ang2 is required for VEGF-mediated angiogenesis, and in the absence of endothelial mitogens Ang2 may induce vascular regression.

The exact mechanism of action of the Angiopoietins remains to be elucidated. For example, high-dose Ang2 can induce downstream activation of Akt and endothelial cell survival, suggesting that it does not simply exert a dominant negative effect on Tie2. The need for improved understanding of these ligands' function is particularly important in the study of tumor angiogenesis, as several studies have now shown that inhibition of Tie2 with a soluble receptor blocks tumor growth, angiogenesis, and metastasis. However, it is unclear whether these effects are due to inhibition of the effects of Ang1 or Ang2, since a soluble receptor would bind both ligands. Specific inhibitors of these ligands have the potential to more precisely modulate Tie2 signaling and serve as valuable therapeutic agents.

Aptamers can comprise single-stranded or double-stranded nucleic acids that are capable of binding proteins or other small molecules. Aptamers that have therapeutic value would most likely bind proteins involved in regulatory cascades. The presence of the aptamer would act as a sink for the protein factors, preventing the factors from carrying out their normal functions. To date, only a few aptamers are known.

It would be desirable to identify novel aptamers that bind to factors in the coagulation cascade, to an E2F family member, or to an angiogenesis factor. Indeed, among other applications, such aptamers have utility in the modulation of coagulation, cell proliferation or angiogenesis, and would thus meet a long-felt and continuing need in the art.

SUMMARY OF THE INVENTION

An RNA aptamer that selectively binds a coagulation pathway factor, that selectively binds an E2F family member, or that selectively binds an angiogenesis factor (e.g. Ang1 and/or Ang2) is provided in accordance with the present invention. Preferably, the binding affinity for the RNA aptamer for the coagulation pathway factor is represented by a dissociation constant of about 20 nanomolar (nM) or less. Optionally, the coagulation pathway factor is selected from the group consisting of thrombin, activated thrombin, IXa, X, Xa, VII, VIIa and combinations thereof. Most preferably, the RNA aptamers selectively bind activated coagulation factors.

A method of modulating the biological activity of a coagulation pathway factor is also provided in accordance with the present invention. The method comprises: (a) administering to a warm-blooded vertebrate in need thereof an effective amount of an RNA aptamer that selectively binds a coagulation pathway factor, the RNA aptamer having a dissociation constant for the coagulation pathway factor of about 20 nM or less; and (b) modulating the biological activity of the coagulation pathway factor in the warm-blooded vertebrate through the administering of the RNA aptamer in step (a).

A method of treating cardiovascular disease in a warm-blooded vertebrate is also provided in accordance with the present invention. The method comprises administering an effective amount of an RNA aptamer that selectively binds a coagulation pathway factor, the RNA aptamer having a dissociation constant for the coagulation pathway factor of about 20 nM or less, to a vertebrate subject suffering from cardiovascular disease, whereby cardiovascular disease in the vertebrate subject is treated.

A method of modulating E2F activity in a warm-blooded vertebrate in which said modulation is desired is also provided. The method comprises: (a) administering to the warm-blooded vertebrate an effective amount of an RNA aptamer that selectively binds an E2F family member, the RNA aptamer having a dissociation constant for the E2F family member of about 20 nM or less; and (b) modulating E2F in the warm-blooded vertebrate through the administering of the RNA aptamer of step (a).

A method of modulating Ang1 or Ang2 activity in a warm-blooded vertebrate in which said modulation is desired is also provided. The method comprises: (a) administering to the warm-blooded vertebrate an effective amount of an RNA aptamer that selectively binds Ang1 or Ang2, the RNA aptamer having a dissociation constant for Ang1 or Ang2 of about 20 nM or less; and (b) modulating Ang1 or Ang2 in the warm-blooded vertebrate through the administering of the RNA aptamer of step (a).

A method of identifying a ligand to a target from a candidate mixture of potential ligands is also provided in accordance with the present invention. Products, i.e., ligands, produced or identified via the method are also provided in accordance with the present invention.

In a preferred embodiment the method comprises: (a) preparing a candidate mixture of potential ligands; (b) contacting the candidate mixture with a target in a lower stringency buffer, wherein ligands having increased affinity to the target relative to the candidate mixture bind to the target; (c) removing unbound candidate mixture; and (d) collecting the ligands that are bound to the target to produce a first collected ligand mixture. More preferably, the method further comprises: (e) contacting the first collected ligand mixture with the target in a higher stringency buffer, wherein ligands having increased affinity to the target relative to the first collected ligand mixture bind to the target; (f) removing unbound ligands; and (g) collecting the ligands that are bound to the target to produce a second collected ligand mixture to thereby identify ligands to the target. Even more preferably, ligands in the first or second collected ligand mixture are enriched or expanded by any suitable technique, e.g. amplification, prior to contacting the first collected ligand mixture with the target in the higher stringency buffer, after collecting the ligands that bound the target in the higher stringency buffer, or both. Optionally, the contacting and expanding or enriching steps are repeated as necessary to produce a desired ligand. Thus, it is possible that the second collected ligand mixture can comprise a single ligand.

Another embodiment of a method of identifying a ligand to a target from a candidate mixture of potential ligands is provided in accordance with the present invention. Products, i.e., ligands, produced or identified via the method are also provided in accordance with the present invention.

The method preferably comprises: (a) providing a target selected from a first species of organism; (b) preparing a candidate mixture of potential ligands; (c) contacting the candidate mixture with the target, wherein ligands having increased affinity to the target from the first species of organism relative to the candidate mixture bind to the target from the first species of organism; (d) removing unbound candidate mixture; (e) collecting the ligands that are bound to the target from the first species of organism to produce a first collected ligand mixture for the target; (f) contacting the first collected ligand mixture with a target from a second species of organism, the target from the second species having at least a portion thereof that is substantially homologous to the same portion in the target from the first species, wherein ligands having increased affinity to the target from the second species relative to the first collected ligand mixture bind to the target; (g) removing unbound first collected ligand mixture; and (h) collecting the ligands that are bound to the target from the second species of organism to form a second collected ligand mixture thereby identify ligands to the target.

Preferably, ligands in the first or second collected ligand mixture are enriched or expanded by any suitable technique, e.g. amplification, prior to contacting the first collected ligand mixture with the target from the second species of organism, after collecting the ligands that bound the target from the second species of organism, or both. Optionally, the contacting and expanding or enriching steps are repeated as necessary to produce a desired ligand. Thus, it is possible that the second collected ligand mixture can comprise a single ligand.

It is therefore an object of the present invention to provide novel RNA aptamers that selectively bind coagulation factors, an E2F family member, Ang1 or Ang2. The object is achieved in whole or in part by the present invention.

An object of the invention having been stated hereinabove, other objects will become evident as the description proceeds, when taken in connection with the accompanying Figures and Laboratory Examples as best described herein below.

BRIEF DESCRIPTION OF THE DRAWINGS

FIG. 1A depicts sequences (SEQ ID NOs:1-12) of representative RNA aptamers of the present invention that bind to and inhibit the activity of coagulation factor IXa.

FIG. 1B depicts sequences (SEQ ID NOs:13-22) of representative RNA aptamers of the present invention that bind to and inhibit the activity of coagulation factor IXa.

FIG. 3A is a plot showing in vitro anticoagulant activity of aptamer $9.3^t$ in porcine plasma. ■, $9.3^t$ APTT; □, $9.3^t$ PT; $9.3^{tm}$ APTT; O, $9.3^{tm}$ PT. Data is presented as the mean±sem.

FIG. 3B is a line graph showing in vivo anticoagulant activity of aptamer 9.3t in pigs following IV bolus injection, Activated Clotting Time (ACT) assays. ■, 1.0 mg/kg $9.3^{t,}$; □, 0.5 mg/kg $9.3^{t,}$; ●, 1.0 mg/kg $9.3^{tm}$; O, Vehicle. Data is presented as the mean±sem. The ACT increase is the ratio of the (pre-injection ACT/post injection ACT) for each time point, 1.0=no change (time 0=pre-injection).

FIG. 3C is a plot showing in vivo anticoagulant activity of aptamer 9.3t in pigs following IV bolus injection, Prothrombin Time (PT) and activated Partial Thromboplastin Time (aPTT) assays. ■, 1.0 mg/kg $9.3^{t,}$; □, 0.5 mg kg $9.3^{t,}$; ●, 1.0 mg/kg $9.3^{tM}$; O, Vehicle. Data is presented as the mean±sem. The increase in the PT or APTT is the ratio of the (pre-injection clot time/post injection clot time) for each time point, 1.0=no change (time 0=pre-injection).

FIG. 5A is a line graph showing in vivo anticoagulant of aptamer $9.3^{t-C}$ in pigs following IV bolus injection, ACT assays. ■, 0.5 mg/kg $9.3^{t-C}$; □, 0.5 mg/kg $9.3^{tM-C}$; dotted line is $9.3^t$ ACT data at 0.5 mg/ml from FIG. 3B. Data is presented is the average of duplicate measurements at each time point.

FIG. 5B is a plot showing in vivo plasma concentration of $9.3^{t-C}$ (solid circle) versus $9.3^t$ (solid square) over time following bolus IV injection. Concentrations calculated by interpolation from in vitro dose response curves of APTT assays for each aptamer.

FIG. 5C is a plot showing in vivo anticoagulant of aptamer $9.3^{t-C}$ in pigs following IV bolus injection, APTT and PT assays. 0.5 mg/kg mg/kg $9.3^{t-C}$; 0.5 mg/kg $9.3^{tM-C}$; * 0.5 mg/kg $9.3^t$ from FIG. 3C; ■, $9.3^{t-C}$ APTT; □, $9.3^{t-C}$ PT; ●, $9.3^{tM-C}$ APTT; O, $9.3^{t-C}$ PT. Data is presented is the average of duplicate measurements at each time point.

FIG. 6A depicts sequences (SEQ ID NO: 23-30 and 73) of RNA aptamers that bind to and inhibit the activity of coagulation factor X and/or its activated form factor FXa.

FIG. 6B depicts sequence (SEQ ID NOS: 31-38) of RNA aptamners that bind to and inhibit the activity of coagulation factor X and/or its activated form factor FXa.

FIG. 10 depicts sequences (SEQ ID NOS:39-47) of RNA aptamers that bind to and inhibit the activation of coagulation factor VIIa.

FIG. 11 is a table depicting full-length thrombin aptamer sequences (SEQ ID NOs:50-56) produced by the toggle SELEX method of the present invention. The noted sequences are proceeded 5' by the following sequence: GGGAGAGAGGAAGAGGGAUGGG (SEQ ID NO: 48); and the noted sequences are followed 3' by the following sequence: CAUAACCCAGAGGUCGAUAGUACUG-GAUCCCCCC (SEQ ID NO: 49).

FIG. 12 is a bar graph depicting human platelet activation by 1 nM human thrombin, in the presence of 30 nM TOG 25 RNA aptamer (SEQ ID NO: 55) or 30 nM nitrocellulose-control aptamer.

FIG. 17 depicts sequences (SEQ ID NOs:64-69) of RNA aptamers that bind to and inhibit the activity of E2F. The aptamers were produced after 10 rounds of the SELEX method and each primer includes an oligonucleotide sequence (SEQ ID NO:62) at the 5' end and at the 3' end (SEQ ID NO:63) as noted. In FIG. 17, and in other parts of the application, if a T is observed in an RNA sequence it should be construed as a U, in that the inclusion of the T is an unintended artifact of a sequencing approach.

FIG. 18 is a table depicting the alignment of a family of FIX/FIXA aptamers of the present invention and depicting a proposed secondary structure of truncated form 9.3$^t$ (SEQ ID NO:70) of aptamer 9-3 (SEQ ID NO: 3) of FIG. 1. In FIG. 18, S1 equals stem 1, L1 equals loop 1, S2 equals stem 2, L2 equals loop 2, and L3 equals loop 3.

FIG. 23A is a line graph showing homologous competition binding assays that demonstrate high affinity binding of both aptamers to FVIIa.

FIG. 23B is a plot showing prothrombin time (PT) clotting assays in human plasma that demonstrate the anticoagulant activity of both aptamers. PT's normalized to a baseline measurements (baseline=~12 sec.) in absence of aptamer, therefore a value of 1=no effect.

DETAILED DESCRIPTION OF THE INVENTION

Figure 2A:
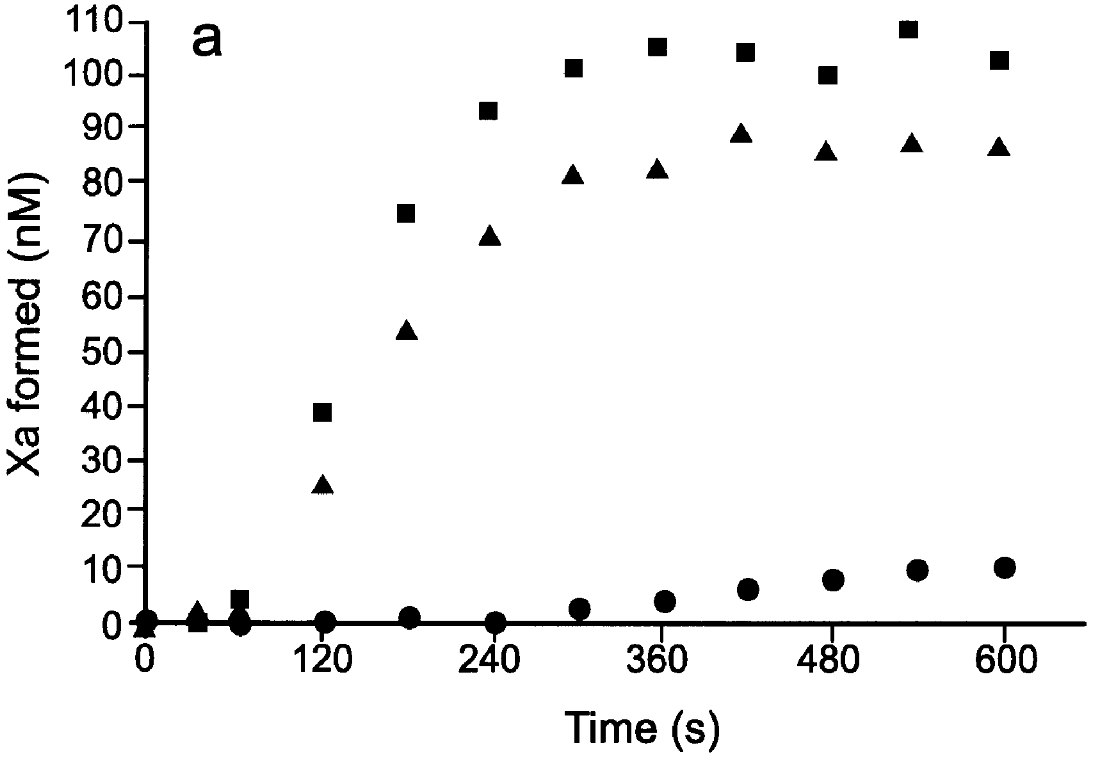
FIG. 2A is a plot of data points showing that RNA 9.3 (SEQ ID NO:3) inhibits the FIXa/FVIIIa catalyzed activation of FX, thereby demonstrating that RNA 9.3 (SEQ ID NO:3) inhibits the activity of coagulation factor IXa. Factor IXa (0.5 nM) was equilibrated with no RNA (▲), 10 nM control RNA (■), or 10 nM RNA 9.3 (SEQ ID NO:3) (●), the FX activation reaction was initiated by the addition of FVIIIa (1 nM), PC/PS vesicles (100 μM) and FX (200 nM), and the amount of FXa formed over time at 37° C. was measured.

The practice of the present invention will employ, unless otherwise indicated, conventional techniques of chemistry, molecular biology, biochemistry, protein chemistry, and recombinant DNA technology, which are within the skill of the art. Such techniques are explained fully in the literature. See, e.g., *Oligonucleotide Synthesis* (M. J. Gait ed. 1984); *Nucleic Acid Hybridization* (B. D. Hames & S. J. Higgins eds. 1984); Sambrook, Fritsch & Maniatis, *Molecular Cloning: A Laboratory Manual*, Second Edition (1989); and the series *Methods in Enzymology* (S. Colowick and N. Kaplan eds., Academic Press, Inc.).

Disclosed herein are RNA aptamer molecules that modulate, and preferably, that inhibit the activities of Factor VII, IX, X and thrombin. Also disclosed herein are E2F RNA aptamers that have been shown to bind E2F family members including E2F-3 to thereby modulate the biological activity of the E2F. Also disclosed herein are RNA aptamers that have been shown to bind Ang1 and Ang2 to thereby modulate the biological activity of Ang1 and Ang2. Optionally, the aptamers are identified through a method known in the art as Systematic Evolution of Ligands by EXponential Enrichment, SELEX; preferably, the aptamers are identified by a modified or toggle SELEX methods as disclosed herein.

The RNA aptamers of the present invention preferably comprise 2'fluoro-pyrimidines to enhance resistance to nuclease degradation. The affinities of the present inventive RNA ligands for the various factors preferably range from $K_d$s of about 100 pM to about 10 nM. In addition, these RNA ligands can act as competitive inhibitors and block factors VIIa, IXa, Xa, and thrombin activity in enzymatic assays. Moreover, these RNA ligands can act as potent anticoagulants and significantly delay the clotting time of normal human plasma or the activation of platelets in response to thrombin. The RNA aptamer ligands for E2F are useful for inhibiting cell proliferation in a number of clinical settings including but not restricted to intimal hyperplasia following bypass graft surgery. The RNA aptamers that have been shown to bind Ang1 and Ang2 to thereby modulate the biological activity of Ang1 and Ang2 can be used in the modulation of angiogenesis.

Also disclosed herein are in vitro selection techniques and combinatorial chemistry methods for identifying and isolating, among other ligands, RNA aptamer molecules that bind to human coagulation factor VII, VIIa, IX, IXa, X, Xa, thrombin and activated thrombin, E2F transcription factors, and Ang1 and Ang2 with high affinity and specificity.

I. DEFINITIONS

The following terms are believed to have well-recognized meanings in the art. However, the following definitions are set forth to facilitate explanation of the invention.

As used herein, a "target" or "target molecule" refers to a biomolecule that could be the focus of a therapeutic drug strategy or diagnostic assay, including, without limitation, proteins or portions thereof, enzymes, peptides, enzyme inhibitors, hormones, carbohydrates, glycoproteins, lipids, phospholipids, nucleic acids, and generally, any biomolecule capable of turning a biochemical pathway on or off or modulating it, or which is involved in a predictable biological response. Targets can be free in solution, like thrombin, or associated with cells or viruses, as in receptors or envelope proteins. Any ligand that is of sufficient size to be specifically recognized by an oligonucleotide sequence can be used as the target. Thus, glycoproteins, proteins, carbohydrates, membrane structures, receptors, organelles, and the like can be used as the complexation targets.

A wide variety of materials can serve as targets. These materials include intracellular, extracellular, and cell surface proteins, peptides, glycoproteins, carbohydrates, including glycosaminoglycans, lipids, including glycolipids and certain oligonucleotides.

The term "ligand" as used herein refers to a molecule or other chemical entity having a capacity for binding to a target. A ligand can comprise a peptide, an oligomer, a nucleic acid (e.g., an aptamer), a small molecule (e.g., a chemical compound), an antibody or fragment thereof, nucleic acid-protein fusion, and/or any other affinity agent. Thus, a ligand can come from any source, including libraries, particularly combinatorial libraries, such as the aptamer libraries disclosed herein below, phage display libraries, or any other library as would be apparent to one of ordinary skill in the art after review of the disclosure of the present invention presented herein.

The term “RNA analog” is meant to refer to a polymeric molecule, which in addition to containing ribonucleosides as its units, also contains at least one of the following: 2'-deoxy, 2'-halo (including 2'-fluoro), 2'-amino (preferably not substituted or mono- or disubstituted), 2'-mono-, di- or tri-halomethyl, 2'-O-alkyl, 2'-O-halo-substituted alkyl, 2'-alkyl, azido, phosphorothioate, sulfhydryl, methylphosphonate, fluorescein, rhodamine, pyrene, biotin, xanthine, hypoxanthine, 2,6-diamino purine, 2-hydroxy-6-mercaptopurine and pyrimidine bases substituted at the 6-position with sulfur or 5 position with halo or $C_{1-5}$ alkyl groups, abasic linkers, 3'-deoxy-adenosine as well as other available “chain terminato” or “non-extendible” analogs (at the 3'-end of the RNA), or labels such as $^{32}P$, $^{33}P$ and the like. All of the foregoing can be incorporated into an RNA using the standard synthesis techniques disclosed herein.

The terms “binding activity” and “binding affinity” are meant to refer to the tendency of a ligand molecule to bind or not to bind to a target. The energetics of said interactions are significant in “binding activity” and “binding affinity” because they define the necessary concentrations of interacting partners, the rates at which these partners are capable of associating, and the relative concentrations of bound and free molecules in a solution. The energetics are characterized herein through, among other ways, the determination of a dissociation constant, $K_d$. Preferably, the $K_d$ is established using a double-filter nitrocellulose filter binding assay such as that disclosed by Wong and Lohman, 1993, *Proc. Natl. Acad. Sci. USA* 90, 5428-5432. Every more preferably, an aptamer of the present invention having a preferred $K_d$ value is further evaluated in an assay for effects on the target. For example, a $K_i$ value as described herein below can be determined for the aptamer and the target.

As used herein, “specifically binding oligonucleotides”, “nucleic acid ligands” or “aptamers” refer to oligonucleotides having specific binding regions that are capable of forming complexes with an intended target molecule in an environment herein other substances in the same environment are not complexed to the oligonucleotide. The specificity of the binding is defined in terms of the comparative dissociation constants ($K_d$) of the aptamer for target as compared to the dissociation constant with respect to the aptamer and other materials in the environment or unrelated molecules in general. Typically, the $K_d$ for the aptamer with respect to the target will be 2-fold, preferably 5-fold, more preferably 10-fold less than $K_d$ with respect to target and the unrelated material or accompanying material in the environment. Even more preferably the $K_d$ will be 50-fold less, more preferably 100-fold less, and more preferably 200-fold less.

The binding affinity of the aptamers herein with respect to targets and other molecules is defined in terms of $K_d$. The value of this dissociation constant can be determined directly by well-known methods, and can be computed even for complex mixtures by methods such as those, for example, set forth in Caceci, M., et al., *Byte* (1984) 9:340-362. It has been observed, however, that for some small oligonucleotides, direct determination of $K_d$ is difficult, and can lead to misleadingly high results. Under these circumstances, a competitive binding assay for the target molecule or other candidate substance can be conducted with respect to substances known to bind the target or candidate. The value of the concentration at which 50% inhibition occurs ($K_i$) is, under ideal conditions, equivalent to $K_d$. However, in no event will a $K_i$; be less than $K_d$. Thus, determination of $K_i$ in the alternative, sets a maximal value for the value of $K_d$. Under those circumstances where technical difficulties preclude accurate measurement of $K_d$, measurement of $K_i$ can conveniently be substituted to provide an upper limit for $K_d$. A $K_i$ value can also be used to confirm that an aptamer of the present binds a target.

As specificity is defined in terms of $K_d$ as set forth above, in certain embodiments of the present invention it is preferred that excluded from the categories of unrelated materials and materials accompanying the target in the target’s environment are those materials which are sufficiently related to the target to be immunologically crossreactive therewith. By “immunologically crossreactive” is meant that antibodies raised with respect to the target crossreact under standard assay conditions with the candidate material. Generally, for antibodies to crossreact in standard assays, the binding affinities of the antibodies for crossreactive materials as compared to targets should be in the range of 5-fold to 100-fold, generally about 10-fold.

In general, aptamers preferably comprise about 10 to about 100 nucleotides, preferably about 15 to about 40 nucleotides, more preferably about 20 to about 40 nucleotides, in that oligonucleotides of a length that falls within these ranges are readily prepared by conventional techniques. Optionally, aptamers can further comprise a minimum of approximately 6 nucleotides, preferably 10, and more preferably 14 or 15 nucleotides, that are necessary to effect specific binding. The only apparent limitations on the binding specificity of the target/oligonucleotide couples of the invention concern sufficient sequence to be distinctive in the binding oligonucleotide and sufficient binding capacity of the target substance to obtain the necessary interaction. Aptamers of binding regions containing sequences shorter than 10, e.g., 6-mers, are feasible if the appropriate interaction can be obtained in the context of the environment in which the target is placed. Thus, if there is little interference by other materials, less specificity and less strength of binding can be required.

As used herein, “aptamer” refers in general to either an oligonucleotide of a single defined sequence or a mixture of said oligonucleotides, wherein the mixture retains the properties of binding specifically to the target molecule. Thus, as used herein “aptamer” denotes both singular and plural sequences of oligonucleotides, as defined hereinabove. The term “aptamer” is meant to refer to a single- or double-stranded nucleic acid which is capable of binding to a protein or other molecule, and thereby disturbing the protein’s or other molecule’s function.

Structurally, the aptamers of the invention are specifically binding oligonucleotides, wherein “oligonucleotide” is as defined herein. As set forth herein, oligonucleotides include not only those with conventional bases, sugar residues and internucleotide linkages, but also those that contain modifications of any or all of these three moieties.

“Single-stranded” oligonucleotides, as the term is used herein, refers to those oligonucleotides that contain a single covalently linked series of nucleotide residues.

“Oligomers” or “oligonucleotides” include RNA or DNA sequences of more than one nucleotide in either single chain or duplex form and specifically includes short sequences such as dimers and trimers, in either single chain or duplex form, which can be intermediates in the production of the specifically binding oligonucleotides. “Modified” forms used in candidate pools contain at least one non-native residue.

“Oligonucleotide” or “oligomer” is generic to polydeoxyribonucleotides (containing 2'-deoxy-D-ribose or modified forms thereof), i.e., DNA, to polyribonucleotides (containing D-ribose or modified forms thereof), i.e., RNA, and to any other type of polynucleotide which is an N-glycoside or C-glycoside of a purine or pyrimidine base, or modified purine or pyrimidine base or abasic nucleotides.

An "RNA aptamer" is an aptamer comprising ribonucleoside units. "RNA aptamer" is also meant to encompass RNA analogs as defined herein above.

The term "coagulation factor aptamer" is meant to refer to a single- or double-stranded nucleic acid that binds a coagulation factor and modulates its function. The term "coagulation factor" is meant to refer to a factor that acts in either or both of the intrinsic and the extrinsic coagulation cascade.

When a number of individual, distinct aptamer sequences for a single target molecule have been obtained and sequenced as described above, the sequences can be examined for "consensus sequences". As used herein, "consensus sequence" refers to a nucleotide sequence or region (which might or might not be made up of contiguous nucleotides) that is found in one or more regions of at least two aptamers, the presence of which can be correlated with aptamer-to-target-binding or with aptamer structure.

A consensus sequence can be as short as three nucleotides long. It also can be made up of one or more noncontiguous sequences with nucleotide sequences or polymers of hundreds of bases long interspersed between the consensus sequences. Consensus sequences can be identified by sequence comparisons between individual aptamer species, which comparisons can be aided by computer programs and other tools for modeling secondary and tertiary structure from sequence information. Generally, the consensus sequence will contain at least about 3 to 20 nucleotides, more commonly from 6 to 10 nucleotides.

As used herein "consensus sequence" means that certain positions, not necessarily contiguous, of an oligonucleotide are specified. By specified it is meant that the composition of the position is other than completely random. Not all oligonucleotides in a mixture can have the same nucleotide at such position; for example, the consensus sequence can contain a known ratio of particular nucleotides. For example, a consensus sequence might consist of a series of four positions wherein the first position in all members of the mixture is A, the second position is 25% A, 35% T and 40% C, the third position is T in all oligonucleotides, and the fourth position is G in 50% of the oligonucleotides and C in 50% of the oligonucleotides.

The terms "cardiovascular disease" and "cardiovascular diseases" are meant to refer to any cardiovascular disease as would be understood by one of ordinary skill in the art. Examples of particularly contemplated cardiovascular diseases include, but are not limited to, atherosclerosis, thrombophilia, embolisms, cardiac infarction (e.g., myocardial infarction), thromboses, angina, stroke, septic shock, hypertension, hyper-cholesterolemia, restenosis and diabetes. More particularly, the terms "cardiovascular disease" and "cardiovascular diseases" are meant to refer to cardiovascular diseases in which thrombosis plays a causative, aggravating and/or indicating role.

The phrase "treating cardiovascular disease" is meant to refer to the treatment of cardiovascular disease at any stage of progression. Thus, treatment of early onset cardiovascular disease as well as treatment of advanced cardiovascular disease falls within the scope of the phrase "treating cardiovascular disease". The phrase "treating cardiovascular disease" is also meant to refer to a therapeutic method directed toward inhibiting the aggravation of cardiovascular disease by modulating coagulation.

The term "truncate" refers to an aptamer that has been truncated by deletion of nucleotides but still possesses a desired or even improved binding characteristic. Truncates can vary in length in accordance with the length of the starting aptamer and as defined above for the term "aptamer". Truncations in the truncate can occur in fixed or variable regions, or both fixed and variable regions, of the starting aptamer.

The term "about", as used herein when referring to a measurable value such as an amount of weight, time, dose, etc. is meant to encompass variations of ±20% or ±10%, more preferably ±5%, even more preferably ±1%, and still more preferably ±0.1% from the specified amount, as such variations are appropriate to perform the disclosed method.

Following long-standing patent law convention, the terms "a" and "an" mean "one or more" when used in this application, including the claims.

II. RNA APTAMERS

An RNA aptamer that selectively binds a coagulation pathway factor, that selectively binds an E2F family member, or that that selectively binds Ang1 or Ang2 is provided in accordance with the present invention. Preferably, the binding affinity for the RNA aptamer for the coagulation pathway factor is represented by dissociation constant of about 20 nanomolar (nM) or less, more preferably about 10 nanomolar (nM) or less. Optionally, the coagulation pathway factor is selected from the group including but not limited to prothrombin, thrombin, IX, IXa, X, Xa, VII, VIIa, V, Va, VIII, VIIIa, tissue factor, XI, XIa and combinations thereof. Most preferably, the RNA aptamers bind activated coagulation factors.

Thus, improved nucleic acid ligands to coagulation factors, to E2F family members, and to Ang1 or Ang2 are disclosed and claimed herein. This invention includes the specific nucleic acid ligands identified herein. The scope of the ligands covered by the invention extends to all ligands of a coagulation factor, to E2F family members, and to Ang1 or Ang2 identified according to the procedures described herein. More specifically, this invention includes nucleic acid sequences that are substantially homologous to and that have substantially the same ability to bind coagulation factors, E2F family members, or Ang1 or Ang2, under physiological conditions, as the nucleic acid ligands identified herein. By substantially homologous, it is meant, a degree of homology in excess of 70%, most preferably in excess of 80%. Alignment techniques are disclosed herein below. Substantially homologous also includes base pair flips in those areas of the nucleic acid ligands that include base pairing regions. Substantially the same ability to bind a coagulation factor, an E2F family member, or Ang1 or Ang2 means that the affinity is within two orders of magnitude of the affinity of the nucleic acid ligands described herein. It is well within the skill of those of ordinary skill in the art to determine whether a given sequence is substantially homologous to and has substantially the same ability to bind a coagulation factor, an E2F family member, or Ang1 or Ang2 as the sequences identified herein.

II.A. Coagulation Factor IX Aptamers

In one embodiment, an RNA aptamer of the present invention selectively binds an activated coagulation factor IXa (FIXa) or inactive form thereof, i.e. (Factor IX). Preferably, the dissociation constant ranges from about 100 pM to about 10 nM. More preferably, the dissociation constant ranges from about 400 pM to about 10 nM, and can optionally comprise any value within the range, e.g. about 500 pM, about 600 pM, about 700 pM, about 800 pM, about 900 pM, about 1 nM, about 2.5 nM, or about 5 nM. Even more preferably, the $K_d$ is established using a double-filter nitrocellulose filter binding assay such as that disclosed by Wong and Lohman, 1993, *Proc. Natl. Acad. Sci. USA* 90, 5428-5432.

Referring now to FIGS. 1A-1B, representative sequences of RNA aptamers of the present invention that bind to and inhibit the activity of FIXa are disclosed. In a preferred embodiment of each of the sequences of FIGS. 1A-1B, all cytidines are 2'-deoxy-2' fluoro cytidine and all uridines are 2'-deoxy-2'-fluorouridine. Binding data for the aptamers of FIGS. 1A and 1B are presented in Tables 1 and 2.

TABLE 1

Affinities (expressed as apparent dissociation constants) of FIX/FIXa Aptamers for FIXa as determined by Double-Filter Nitrocellulose Filter Binding Assays

| Sequence | $K_d$ (pM) | SEQ ID NO: |
|---|---|---|
| 9.3 | 500-700 | 3 |
| 9.19 | 500-1000 | 16 |
| 9.20 | 400-600 | 17 |
| 9.25 | 400-600 | 19 |
| 9.26 | 400-600 | 20 |
| 9.27 | 1500-1800 | 21 |
| 9.28 | 500-700 | 22 |

TABLE 2

Primary sequence of the minimal or truncated FIXa aptamers 9.3$^t$ and 9.20$^{t*}$ 9.3$^t$:
(SEQ ID NO: 70)
5' AUG GGG ACU AUA CCG CGU AAU GCU GCC UCC CCA U 3'

9.20$^t$:
(SEQ ID NO: 71)
5' GGG GAC UAU ACC GGC AAU CGU GCA UCC CC 3'

The apparent $K_d$ of the 9.20 truncate for FIXa is ~100-200 nM. The apparent $K_d$ for binding of the 9.3 truncate to FIXa and to FIX is described in Table 3 immediately below.

TABLE 3

Aptamers to Coagulation Factor IXa

| Protein | Aptamer | | |
|---|---|---|---|
| | 9.3 | 9.3$^t$ | 9.3$^{tM}$ |
| Factor IXa | 0.65 ± 0.2 nM | 0.58 ± 0.05 nM | >10 µM |
| Factor IX | 3.96 ± 0.7 nM | 4.7 ± 0.8 nM | n.d. |
| Factor VIIa | n.d. | >5 µM | n.d. |
| Factor Xa | n.d. | >5 µM | n.d. |
| Factor XIa | n.d. | >5 µM | n.d. |
| APC | n.d. | >5 µM | n.d. |

Table 3 shows affinity of 9.3 and related aptamers to FIXa and other coagulation factors; 9.3 is a full-length aptamer, while 9.3t is a 35 nucleotide truncated version of 9.3.

Figure 20:
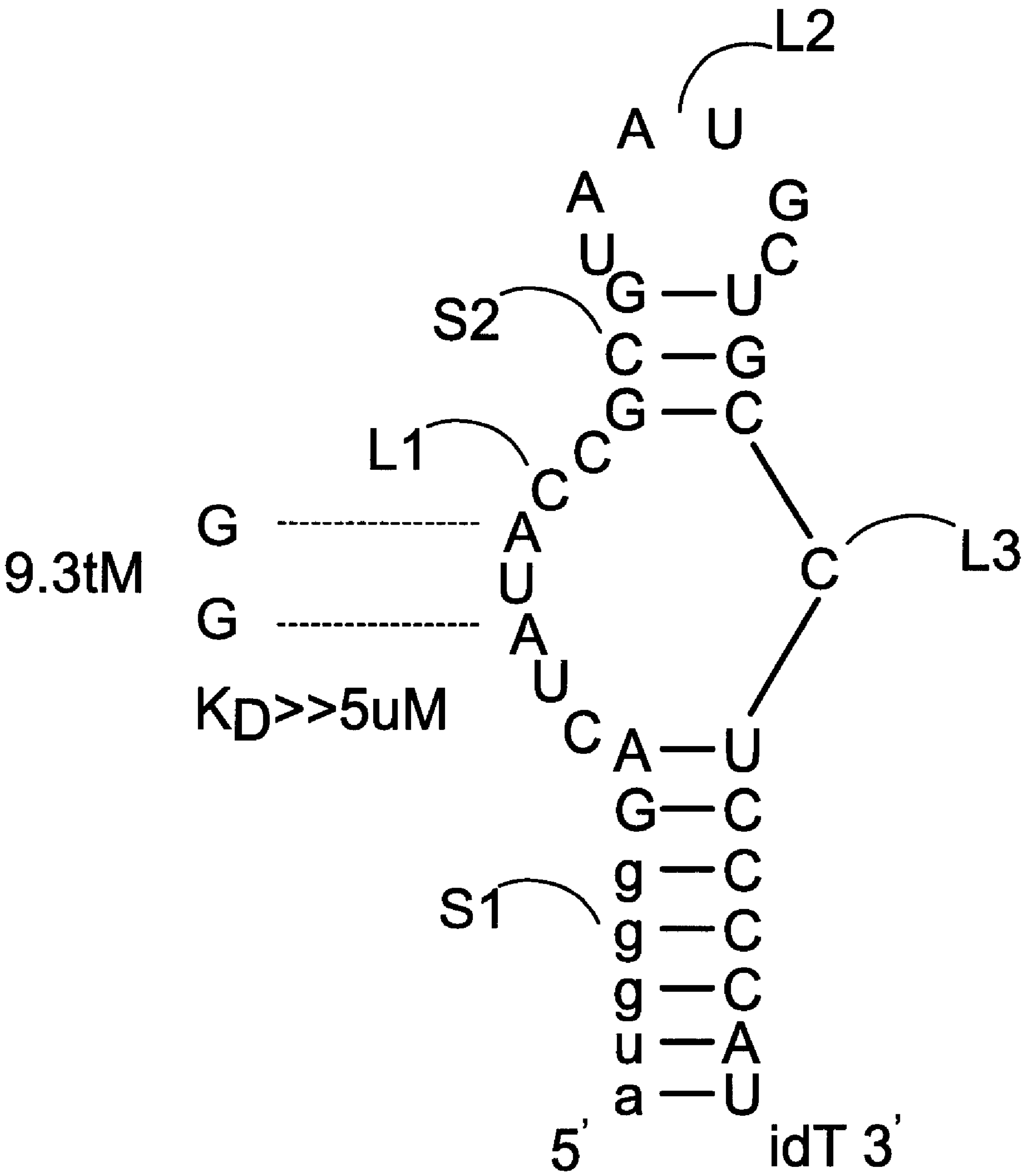
FIG. 20 depicts the secondary structure of coagulation factor IXa RNA aptamer 9.3$^t$ (SEQ ID NO:70). The A-G substitutions that are used to create the mutant control aptamer 9.3$^{tM}$ ($K_D$ for factor IXa>>5 μM) are also shown. S1 equals stem 1, L1 equals loop 1, S2 equals stem 2, L2 equals loop 2, and L3 equals loop 3.

Referring now to FIGS. 18 and 20, an alignment of FIX/FIXA aptamers of the present invention is presented, along with a proposed secondary structure of truncated aptamer 9-3$^t$ (SEQ ID NO: 70). As shown in FIGS. 18 and 20, the alignment of the FIX/FIXA aptamers suggest a first stem region S1 followed by a first loop region L1, and then a second stem region S2 and a second loop region L2. A third loop region L3 is also suggested. The motif AUA is common in the L1 region and thus, preferably, a FIX/FIXA aptamer of the present invention comprises the AUA motif. Thus AUA motif thus comprises a consensus sequence for this family of aptamers. Additionally, in the 5' direction, it is preferred that 2 additional nucleotides are present, and the nucleotides N in the 5' direction can be selected from the group including but not limited to C, U, G, A and identical combinations thereof. Thus, the sequence NNAUA is also a consensus sequence for this family of aptamers.

Continuing with FIGS. 18 and 20, it is also preferred that the S1 region preferably comprises about 5 nucleotides at the 5' end that form base pairs with about 5 base pairs at the 3' end to maintain the stem structure. By "pair forming" it is simply meant the ordinary complimentary base pair formation found in RNA molecules. To elaborate, the secondary structure of an RNA motif can be represented by contact in two dimensions between specific nucleotides. The most easily recognized secondary structure motifs are comprised of the Watson/Crick base pairs A:U and C:G. Non-Watson/Crick base pairs, often of lower stability, have been recognized, and include the pairs G:U, A:C, G:A, and U:U. (Base pairs are shown once; in RNA molecules the base pair X:Y by convention represents a sequence in which X is 5' to Y, whereas the base pair Y:X is also allowed.) A conventional nomenclature for the secondary structures thus includes stems, loops, hairpin loops, asymmetric bulged hairpin loops, symmetric hairpin loops, and pseudoknots.

II.B. Coagulation Factor VII Aptamers

In another embodiment, an RNA aptamer of the present invention selectively binds activated coagulation factor VII (FVIIa) or an inactive form thereof, i.e. (Factor VII). Preferably, the dissociation constant ranges from about 100 pM to about 10 nM. More preferably, the dissociation constant ranges from about 400 pM to about 10 nM, and can optionally comprise any value within the range, e.g. about 500 pM, about 600 pM, about 700 pM, about 800 pM, about 900 pM, about 1 nM, about 2.5 nM, or about 5 nM. Even more preferably, the $K_d$ is established using a double-filter nitrocellulose filter binding assay such as that disclosed by Wong and Lohman, 1993, *Proc. Natl. Acad. Sci. USA* 90, 5428-5432.

Referring now to FIG. 10, representative sequences of RNA aptamers of the present invention that bind to and inhibit the activity of coagulation factor FVIIa are disclosed. In a preferred embodiment of each of the sequences of FIG. 10, all cytidines are 2'-deoxy-2' aminocytidine and all uridines are 2'-deoxy-2'-aminouridine. Binding data for the aptamers of FIG. 10 are presented in the Laboratory Examples.

Table 4 shows additional sequences of RNA aptamers isolated to coagulation factor VIIa. Shown are the random-region derived sequences (5' to 3') of aptamers resulting from the selection against FVIIa. In a preferred embodiment, all pyrimidines are 2'fluoro-modified. The random region derived sequences are flanked by fixed sequences from the library as shown: 5' gggagagaggaagagggauggg (SEQ ID NO:102) -random region-cauaacccagaggucgau 3' (SEQ ID NO:103). Binding data for the aptamers of Table 4 are presented in the Laboratory Examples. In Table 4, the numerals "10" and "11" refer to the fact the aptamer was isolated after ten (10) rounds or eleven (11) rounds of SELEX, respectively.

TABLE 4

FVII/FVIIa Aptamers

| SEQ ID NO: | SELEX ROUND AND SPECIE | Randon Region of Aptamer Sequence |
|---|---|---|
| 74 | 11-15 | AAAGUACCGACUAGGUCCCACUGUUUAAGCAUCCCCGAAC |
| 75 | 10-15 | AAGCUCCAUCCAAGCGACGACACGCUCGUCCCGAAAAGAAU |
| 76 | 10-1, 10-5, 11-19 | AAGCUCCGUCCAAGCGACGACACGUUCGUCCCGAAAAGAAU |
| 77 | 11-6, 11-27 | ACAACGCCACCUUCCGCGCGACGCCGCGCCGACGAUAACU |
| 78 | 10-7 | ACAACGCCACCUUCCGCGCGACGCCGCGCCGACGUAUAACU |
| 79 | 11-1 | ACGAAAAUAUCUCCGUCAAGGACCUCCUGCCCCAAACACU |
| 80 | 11-17 | AGACGACACAUCCAAGCGUGAGAGAUCACCCGACAAGAAU |
| 81 | 11-20 | AUUUUUUCACACAUUCUUAAUUUUCACUUACCCGUCCCGAUC |
| 82 | 10-9 | CAAAGCACCCGUCCAAGCGACAGACAUGUCCCGCAGCCCU |
| 83 | 10-13 | CACCAUUUAUUCUUCAUUUUUCUUCGCCCAGUUCCUCCAA |
| 84 | 10-14 | CAUAAGCCGCCUCAGCUGACAAAGCCCUCCGCUUAGGCC |
| 85 | 11-23 | CCAAAGUGCUUCCGCGAAGUUCGACCAUUCGCCGCCUGCA |
| 86 | 10-11 | CCCCUCCGCCAACUUGGCCGCCUCAGGCACCAUCACCAAC |
| 87 | 10-2 | CCCGAUCUCCCCGAGGACCUCCACGGCCCGUCCGCCAGUUU |
| 88 | 11-3 | CCGCCUCAGCAAUCUAGCCCUCCGCCCGACCCUUCCGCUG |
| 89 | 11-12, 11-13 | CCGCCUCAGCGAGAUCUUCGCCCUCCGCCCAAGCCUCAAC |
| 90 | 11-25 | CCGCCUCAGGACGACACCGGUCCCCUCCGCCCGUCCGCGC |
| 91 | 10-3 | CCGCCUCAGGCAUCAGCCCCUCCGCCCGCCCACUUCAUCA |
| 92 | 10-12 | CCGCCUCAGUUACUUGAUAACCCUCCGCCCGCCCGCAGCU |
| 93 | 11-18 | CUUUACAUAUUACUUACUACAUUUUCAUAACACCACACGC |
| 94 | 11-7 | GACACCAUCCAAGCGACCAACCAAGGUCCCGCACAUAACU |
| 95 | 10-10 | GAUGCAACUCGAAAUGGCCGCCUCGCGUCAGCGUUCCGC |
| 96 | 10-4 | GCUUAUCUUAUAUCACUUUUUCUUCCCAAUCCUUCAAGU |
| 97 | 10-6, | |
| 98 | 11-5 | UAACCAACCAAGCGUCCAAAAACCUGGACCCGCCAAGAAU |
| 99 | 11-14 | UAACCAACCAAGCGUCCAAAAAUCUGGACCCGCCAAGAAU |
| 100 | 11-10 | UCUGACGUUCCACCGUCCUCGAAGGCGACCAGAGCGUUAC |
| 101 | 11-8, 11-16 | UGCCGCCUCAGCCACACGGCCCUCCGCGCCCGCCACAAGC |

II.C. Coagulation Factor X Aptamers

In another embodiment, an RNA aptamer of the present invention selectively binds activated coagulation factor Xa (FXa) or an inactive form thereof, i.e. (Factor X). Preferably, the dissociation constant ranges from about 100 pM to about 10 nM. More preferably, the dissociation constant ranges from about 400 pM to about 10 nM, and can optionally comprise any value within the range, e.g. about 500 pM, about 600 pM, about 700 pM, about 800 pM, about 900 pM, about 1 nM, about 2.5 nM, or about 5 nM. Even more preferably, the $K_d$ is established using a double-filter nitrocellulose filter binding assay such as that disclosed by Wong and Lohman, 1993, *Proc. Natl. Acad. Sci. USA* 90, 5428-5432.

Referring now to FIGS. 6A-6B, representative sequences of RNA aptamers of the present invention that bind to and inhibit the activity of FXa are disclosed. In a preferred embodiment of each of the sequences of FIGS. 6A-6B, all cytidines are 2'-deoxy-2' fluorocytidine and all uridines are 2'-deoxy-2'-fluorouridine. Binding data for the aptamers of FIGS. 6A and 6B are presented in the Laboratory Examples.

Table 5 shows additional sequences of RNA aptamers isolated to coagulation factor X/Xa. Binding data for the aptamers of Table 5 are presented in the Laboratory Examples, including Example 12. In Table 5, the numerals "10" and "11" refer to the fact the aptamer was isolated after ten (10) rounds or eleven (11) rounds of SELEX, respectively. The FXa sequences listed in table 5 are flanked by fixed sequences that are the same as the fixed sequences described in the preceding section on aptamers to factor VIIa. That is, the 5' and 3' flanking sequences are, respectively, SEQ ID NOs:102 and 103.

TABLE 5

| SEQ ID NO: | SELEX Round And Specie No. Clone | Sequence | Kd (nM) |
|---|---|---|---|
| 104 | F11-8 | AgAuuAGCCCCAGCGAGAuAAuACuuGGCCCCGCuACuAC | 2.2 |
| 105 | D7-9 | uAAAuAGCCCCAGCGAGAuucuACuuGGCCCCGCuACuAC | 2.633 |
| 106 | D6-6 | AAAAuAcgCCannCGAGAuuAuACuuGGCCCCGCuAauAC | 3.1 |
| 107 | F11-7 | AAAAuAGCCCCAGCGAGAuAAuACuuGGCCCCGCuAuuAC | 3.6 |
| 108 | D7-6 | AAAAuAGCCCCAGCGAGAuAAuACuuGGCCCCGCuAgcAC | 3.8 |
| 109 | D6-2 | AAAAuAGCCCCAGCGAGAuAAuACuuGGCCCCGCuACaAC | 4.6 |
| 110 | D7-1 | AgAAugGCCCCAGCGAGAuuAuACuuGGCCCCGCcAauAC | 4.7 |
| 111 | D6-1 | AAAAuAGCCCCAGCGAGAugAuACuuGGCCCCGCuAauAC | 4.8 |
| 112 | D7-7 | AgAAuAcgCCuAGCGAGAagAuACuuGGCCCCCGugCaAC | 5.8 |
| 113 | D6-3 | AAAAuAGCCCCAGCGAGAuAAuACuuGGCCCCGCuguuAC | 5.9 |
| 114 | D6-9 | AAAuuuGCCCCAGCGAGAuAAuACuuGGCCCCGCaACuAC | 6.5 |
| 115 | D4-7 | AuAAuAGCCCCAGCGAGAuAAuACuuGGCCCCGCuACuAa | similar to 10-14 |
| 116 | D7-2 | AgAAuAGCCCCAGCGAGAuAAuACuuGGCCCCGCuAauAC | 8.1 |
| 117 | D6-4 | AAAuuuGCCCuAGCGAGAuuAuACuuGGCCCCGCgAaaaAC | 8.5 |
| 118 | E10-12 | AAAAuAGCCCCAGCGAGAuAAuACuuGGCCCCGCgAacAC | 11.7 |
| 119 | D6-7 | ugcAuAGCCCCAGCGAGAuAAuACuuGGCCCCGCuACaAC | 13.2 |
| 120 | D7-8 | ngAuuAGCCCnAGCGAGAuAnuACuuGGCCCCGCuACnuC | 14.49 |
| 121 | D4-8 | AAAAuAaCCaCAGCGAGAucAuACuuGGCCCCGuuACuAC | 2 fold higher |
| 122 | D4-10 | AAAAuAGCCCuAGCGAGAuAAuACuuGGCCCCGCcACaua | 2 fold higher |
| 123 | D6-10 | cAgAuAGCCaCAGCGAGAucAuACuuGGCCCCGCuACuAC | 18.7 |
| 124 | D4-5 | AgAAuAGCCCCAGCGAGAuAAucCuuGGCCCCGCuACugC | 21.66 |
| 125 | D4-6 | AAncuAGCCCnAGCGAGAuAuuACuuGGCCCCGCnACuAC | 3 fold higher |
| 126 | D7-5 | AAAcuAGCCuCAGCGAGAuAAuACuuGGCCCCGCuACuAC | 26.1 |
| 127 | E10-11 | CCAGAAGCGCuCACuACAACGuuGAACCCCCCGuCCACAC | 27.11 |

TABLE 5-continued

| SEQ ID NO: | SELEX Round And Specie No. Clone | Sequence | Kd (nM) |
|---|---|---|---|
| 128 | E10-8 | CCAAAAGCGGACuGAAGACGuGuuuCCCCCAuCuCCGuGA | 28.38 |
| 129 | E9-8 | CCAGAAGGAACuAAACACCuGAACCCCCCAuCGCGAGAGA | 29.81 |
| 130 | F11-6 | CCAGCAACGuCACACGAACGGAAuACCCCCCAuuGAAAAC | 33.6 |
| 131 | E10-4 | uCuuAGAuAuAGAACuCCGAGAGGACuGACCGuACAGAAC | 37.44 |
| 132 | D7-4 | AgAAuAGCCCCAGCGAGAucguACuuGGCCCCGCuAguAC | 39.3 |
| 133 | E9-3 | CCAAAAGCGCAuACACCuGCGuGuuuCCCCCGCCAACAGu | 46.55 |
| 134 | E10-1 | CCAuuGCuNCCCuGAACANGGGCNCCACNCCGCCuNCACAGu | 51.7 |
| 135 | E9-9 | CCAGAACACCAGuGAACCCCCCAGCCCCuuCuCACCAGAu | 52.81 |
| 136 | E9-5 | CCAGAAGCGACACuAACGCuGAACCCCCCAGuCCCuuCACGuG | 53.5 |
| 137 | E9-2 | AuACCGAGCACGCAAAACACACAAuGCCCAAGCAGGACu | 58.6 |
| 138 | E9-4 | AGCCCGAGAAAAuAACGCGuuCCACCAuACuACuAAGC | 65 |
| 139 | D4-3 | uAAAuAGCCCCAGCGAGAuAAuACuuGGCCCCGCaACuAC | 65.5 |
| 140 | E10-7 | AGuCCGACuGGAGAACANGuACuCuAuAAGCACuuNCAuNCAN | 69.45 |
| 141 | F11-10 | CuCGGCAGAAGACACGCAuuCACCuGGuGCCACCuCGuAA | 84.43 |
| 142 | E10-6 | GCCGuCGCCAGGAAuCAAACuGCuACuCCAuCCCGGGCA | 85.7 |
| 143 | E9-6 | CCAGAAGCuAAACACuCAuAACCACGCuGAACCCCCCAAC | 95.1 |
| 144 | E9-10 | CCAGAACCAACuGCGGuGAACCCCCCAuACCGCGACACAu | 130.4 |
| 145 | D4-2 | AAcuuAGCCuCAGCGAGAuAAcgCuuGGCCCCGCuAagAC | 540 |
| 146 | D4-9 | uAAguuGCCCCAGCGAGAuAguACuuGGCCCCGCuACuAa | >240 |
| 147 | E 9-1 | AAAAuAGCCCCAGCGAGAuAAuACuuGGCCCCGCuACuAA | |

II.D. Thrombin Aptamers

In another embodiment, an RNA aptamer of the present invention selectively binds coagulation factor thrombin (activated) (Factor IIa (FIIa)), or an inactive form thereof (i.e. prothrombin, factor VII). Preferably, the dissociation constant ranges from about 100 pM to about 10 nM. More preferably, the dissociation constant ranges from about 400 pM to about 10 nM, and can optionally comprise any value within the range, e.g. about 500 pM, about 600 pM, about 700 pM, about 800 pM, about 900 pM, about 1 nM, about 2.5 nM, or about 5 nM. Even more preferably, the $K_d$ is established using a double-filter nitrocellulose filter binding assay such as that disclosed by Wong and Lohman, 1993, *Proc. Natl. Acad. Sci. USA* 90, 5428-5432.

Referring now to FIG. 11, representative full-length thrombin aptamer sequences are disclosed, along with dissociation constants ($K_d$) for human and porcine thrombin. Significantly, 13 rounds of the toggle SELEX method disclosed herein in accordance with the present invention produced these aptamers. A preferred consensus sequence of these aptamers comprises AACAA. A preferred embodiment of a thrombin aptamer sequences comprises the sequence referred to as toggle 25 (TOG25; SEQ ID NO: 55). A truncated form of this aptamer was also prepared, and the truncate is referred to herein as TOG 25 short (SEQ ID NO: 57).

Figure 15:
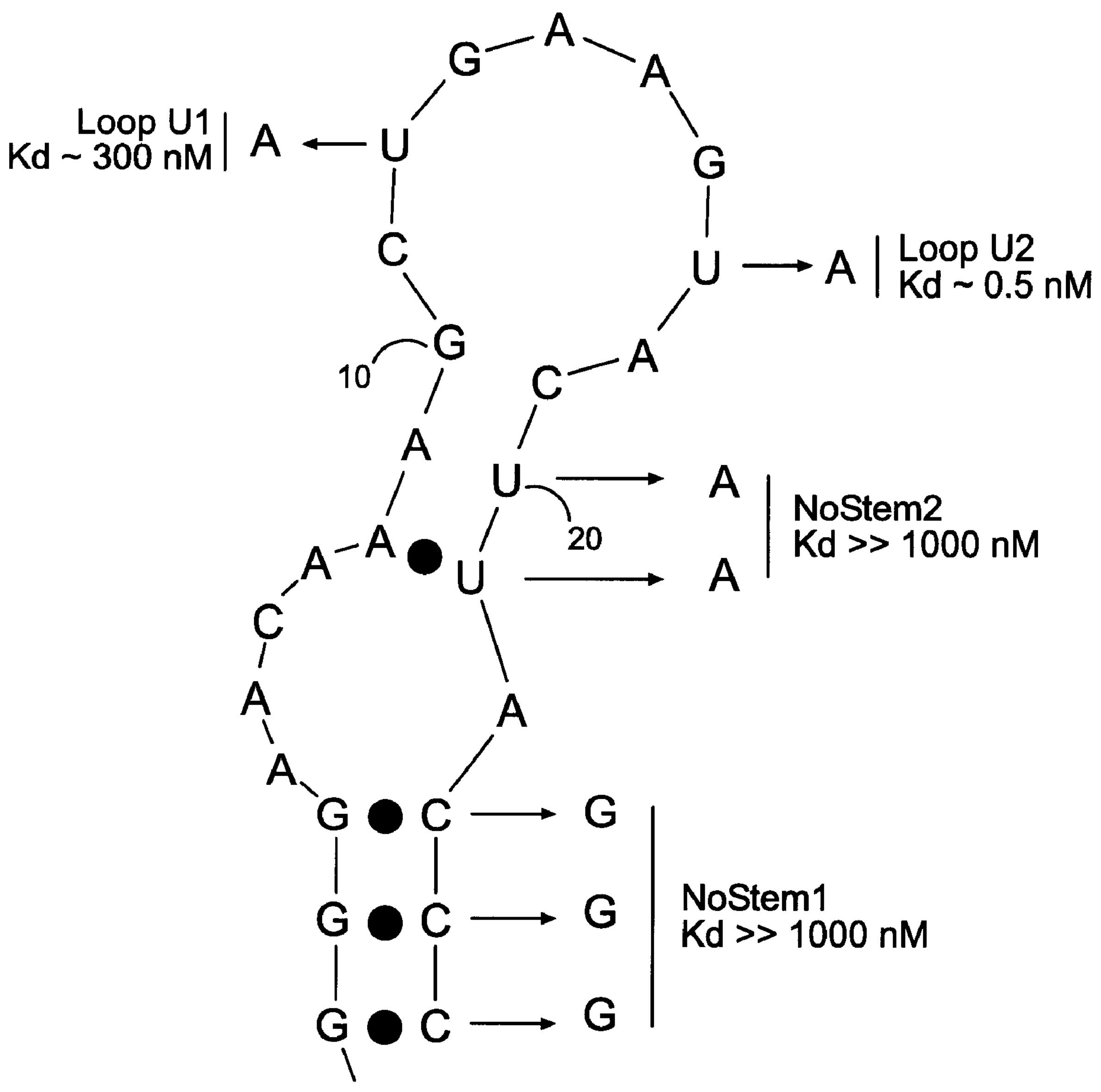
FIG. 15 is a schematic of a proposed structure of a 25-MER truncate of TOG 25 (TOG 25 short, SEQ ID NO: 57). The "wild-type" truncate binds human thrombin with a $K_d$ of about 1 nM. The binding affinity of various mutants designed to disrupt the stem (no stem, SEQ ID NO: 58), BULGE (BULGE Us, SEQ ID NO: 59), and loop sequence (loop U1, SEQ ID NO: 60, and loop U2, SEQ ID NO: 61) are also shown.

As shown in FIG. 15, a thrombin RNA aptamer of the present invention preferably comprises about 3 pair forming nucleotides followed by the AACAA consensus sequence and two additional pair forming nucleotides. As shown in FIG. 15, the pair forming nucleotides form pairs with complementary nucleotides proximate to the 3' end of the TOG 25 short aptamer.

II.E. E2F Aptamers

In another embodiment, an RNA aptamer of the present invention selectively binds E2-F, also referred to as "an E2F family member". Thus, the terms "E2-F" and "E2-F family member" encompass any E2F family member, whether now known or hereafter identified. Representative E2F family members include but are not limited to E2F-1, E2F-2, E2F-3, E2F-4, E2F-5 and E2F-6. Preferably, the dissociation constant ranges from about 100 pM to about 50 nM. More preferably, the dissociation constant ranges from about 400 pM to about 10 nM, and can optionally comprise any value within the range, e.g. about 500 pM, about 600 pM, about 700 pM, about 800 pM, about 900 pM, about 1 nM, about 2.5 nM, about 5 nM, or about 10 nM. Even more preferably, the $K_d$ is established using a double-filter nitrocellulose filter binding assay such as that disclosed by Wong and Lohman, 1993, *Proc. Natl. Acad. Sci. USA* 90, 5428-5432.

Referring now to FIG. 17, representative sequences of RNA aptamers (SEQ ID NO: 62-69) that bind to and inhibit the activity of E2F family members including E2F-3 are disclosed. Each of the aptamers (SEQ ID NO: 64-69) are preferably bounded at their 5' end by the 5 primer sequence 5'P of SEQ ID NO: 62 and are preferably bounded at their 3' end by the 3 primer sequence 3'P of (SEQ ID NO: 63). These primers were identified after 10 rounds of SELEX wherein the SELEX method was modified in accordance with the matrix conditions described in Examples 1 and 2. The approximate $K_d$'s for these aptamers are set forth in Table 6.

TABLE 6A

Approximate $K_d$'s for E2F Aptamers

| Aptamer No. | SEQ ID NO. | $K_d$ |
|---|---|---|
| 10-1 and 10-8 | 64 | 1.5 nM |
| 10-2 | 65 | 3 nM |
| 10-3, 10-7, 10-11 and 10-12 | 66 | 1 nM |
| 10-4 | 67 | 5 nM |
| 10-5 | 68 | 2.5 nM |
| 10-6 | 69 | 2 nM |

Thus, RNA aptamer ligands that selectively bind to an E2F family member, e.g. E2F-3, are disclosed herein. Among other utilities as disclosed herein, these aptamers have utility in the control of cell proliferation, which is of central importance to the proper development of a multi-cellular organism, the homeostatic maintenance of tissues, and the ability of certain cell types to respond appropriately to environmental cues. E2F is a family of transcription factors and modulation of E2F activity is envisioned to be particularly effective in repeating a wide variety of proliferative events in view of the control of E2F activity occurring as the end result of G1 cyclin dependent kinase regulatory cascades that involve the Rb family of proteins. See, e.g., Sherr, C. J., *Cell,* 73:1059-1065 (1993); Hunter, T., *Cell* 75:839-841 (1993); Nevins J. R., *Science* 258:424-429 (1992); Helin, K. and Harlow, E., *Trends Cell Biol.* 3:43-46 (1993); La Thangue, N. B., *Trends Biochem. Sci.* 19:180-114 (1994); Sherr, C. J. and Roberts, J. M., *Genes Dev.* 9:1149-1143 (1995); Weinberg, R. A. *Cell* 81:323-330 (1995) Harbour, J. W. and Dean, D. C., *Genes and Development* 14:2393-2409 (2000); and Black, A. R. and Azizkhan-Clifford, J., *Gene* 237:281-302 (1999).

Table 6B shows additional sequences of RNA aptamers isolated to an E2F family member. Shown are the random-region derived sequences (5' to 3') of aptamers resulting from the selection against E2F. In a preferred embodiment, all pyrimidines are 2'fluoro-modified. The random region derived sequences are flanked by fixed sequences from the library as shown: 5' GGG GGA AUU CUA AUA CGA CUC ACU AUA GGG AGA GAG GAA GAG GGA UGG G (SEQ ID NO:188)-random region-C AUA ACC CAG AGG UCG AUA GUA CUG GAU CCC CCC 3' (SEQ ID NO:63). Binding data in the form of $K_d$ values are also shown.

TABLE 6B

E2F Aptamers

| SEQ ID NO: | Random Region of Aptamer Sequence | $K_d$ |
|---|---|---|
| 189 | GCUGCCGCGCCUGGACCCCACCCACAUAUGGGCCACACAC | 1.5 nM |
| 190 | AAUGACAAU UGACUCGGAAACCCUCAUGUUCCAACACCGG | |
| 191 | CCUACUCUCCACACCUGGUUUUAUGCUCUACACACCUCAC | |
| 192 | CUGCCCCGACCACAAAGGACGGAACCCUACCCACAGUGGG | |
| 193 | CAUAAAAGCAAUUUGCCACCGGCGUACGGCACCCCAAUAU | |
| 194 | CACCUAUGCCAUCAGGCCUCAAUCUCCGGCAGCGACUCUA | |
| 195 | AUCAACCACAGGAAGAGUGCAGCCAUAGCACACAGACCA | |
| 196 | GCGACAUACCCCACCCACACUGGCACAACGCGCAAUGCCG | |
| 197 | CUUCAAAGGUCCUGUAUCCAGCCACCCCACUGACAGGA | |
| 198 | CUACCCAGCAAGGUCAACCCUACCCACACUGG | 1.75 nM |
| 199 | AUCUUAAAGAUCACCGGCGUUCGGCAACACCCGACCCAAA | |
| 200 | GCACUAAACUUCGAUUACCCCCCACCCACACUGGCUGCAC | 4 nM |
| 201 | CAGAUUACCCUACCCACACUGCGUGCGGACAACCAUUGGC | 0.4 nM |
| 202 | GCACAAAUGAGAACACGAGUUCACCCCGCCCACACUGGA | |
| 203 | GCGCAGAUCAACCCUACCCAUACUGGGCUCCUUGUGAAGG | |
| 204 | CAAGCGCUGAAACCAAUGCACCCCACCCCACACUGGUGUAC | 1.25 nM |
| 205 | AUGUGAAACACAGAAGCCCUGUACAGACCGCCGACUGUCA* | |
| 206 | CAAACUCACAGACACCAACUGCAGGAGCACCCACCACGAC | |
| 207 | CGAACGAACUGUGGACCCUACCCACACUGGGCCAAGCGAU | 0.4 nM |

TABLE 6B-continued

| E2F Aptamers | | |
|---|---|---|
| SEQ ID NO: | Random Region of Aptamer Sequence | $K_d$ |
| 208 | CGCCCUGGAACGAGAUUCCUGUAAACCCCCAUCUAGUAGA | |
| 209 | CAAGGUGACCGCGAACCCUACCCGCCGCACGGUAACAGCG | |
| 210 | CAUCCAGACUACUGGCCCAACCCGCCGCUCCAACCCCGUG | |
| 211 | CUCUCUCCGUAACCAACAAGUCCCAAUGAACAACCACCAU | |
| 212 | CACUGAACGAAUGGCAACCGCCAAACCCUACCCACACUGG* | 0.2 nM |
| 213 | CAAGCGUAUACCCUACCCACACUGAGCUACAUUGCGCUGA | 8 nM |
| 214 | GCCGAGAGUGAGUGACCACAACCCCGCCCACACUGGAAUA | 1.5 nM |
| 215 | UUUCCUAUGGCGAUAACUUCAGCCACGCCGGCGCCCCGUG | 30 nM |
| 216 | CGUCACUCCGUCCCAGCCGACGAAGUCCGUAAUUCCUCCA | 45 nM |
| 217 | CCACCCGAAGCAAAUCAAGCCCGACGGCGCUCGGACCAAC | 15 nM |
| 218 | CGAACUGAAGCUAGCGUAACCCUACCCACACUGCACGUG | 0.5-4 nM |
| 219 | ACCUCGACCCUUCACCUGACUCUCCCAGAAGUUCUGUUUC | 2 nM |
| 220 | CAAUCCAUACGCACCCGGUCCACACUGGGUUGGAGCNNN | 1-40 nM |
| 221 | AAUGGAAUCACUGAAGGCCCUCCGUAGCACCUAACACAGU* | 1.5 nM |
| 222 | GCAUCCUGCCAGCGGCGACGGACCUUCGCCCACAGGCCUC | 2 nM |
| 223 | UUAUAUAGCACACUGAAGCCCUCAGCAAAACCUCCACAGG* | 1.5 nM |
| 224 | UAUGAAAUCACAGAAGCCCGCGUUCGACACCUCC A CUGUU* | 3 nM |
| 225 | CAAACUCACAGACUCCAACUGCAGGAGCACCCACCCACACUGGG ACAG | 0.25-2.5 nM |
| 226 | AUCCCCGCCGUAAGCCGUCCUGAUGGACACCACACGCCGC* | 2 nM |

II.F. Angiopoietin-1 (Ang1) and Angiopoietin-2 (Ang2) Aptamers

Tie2 is an endothelial receptor tyrosine kinase (RTK) that is required for both embryonic vascular development and pathological angiogenesis. Tie2 is unique among RTKs in that it has two ligands with apparently opposing actions. Angiopoietin-1 (Ang1) is an activating ligand while Angiopoietin-2 (Ang2) is thought to be a naturally occurring antagonist for Tie2. Mice lacking Tie2 or Ang1 die midway through gestation due to abnormalities of vascular morphogenesis characterized by deficient recruitment of supporting smooth muscle cells and pericytes. Moreover, Ang1 promotes endothelial cell survival and blocks the increases in vascular permeability induced by vascular endothelial growth factor (VEGF), supporting a role for Ang1 in the stabilization and maintenance of the adult vasculature. In contrast, Ang2 is required for VEGF-mediated angiogenesis, and in the absence of endothelial mitogens Ang2 may induce vascular regression.

The exact mechanism of action of the Angiopoietins remains to be elucidated. For example, high-dose Ang2 can induce downstream activation of Akt and endothelial cell survival, suggesting that it does not simply exert a dominant negative effect on Tie2. The need for improved understanding of these ligands' function is particularly important in the study of tumor angiogenesis, as several studies have now shown that inhibition of Tie2 with a soluble receptor blocks tumor growth, angiogenesis, and metastasis. However, it is unclear whether these effects are due to inhibition of the effects of Ang1 or Ang2, since a soluble receptor would bind both ligands. Specific inhibitors of these ligands have the potential to more precisely modulate Tie2 signaling and serve as valuable therapeutic agents. The present invention provides RNA aptamer ligands for Ang1 and Ang2.

A random library of 2'-fluoro modified RNA was created with the following sequence:

GGGAGAGAGGAAGAGGGAUGGG (SEQ ID NO:149)-$N_{40}$—CAUAACCCAGAGGUC-GAUAGUACUGGAUCCCCCC (SEQ ID NO:150), where $N_{40}$ is a random region.

In vitro selection was performed using recombinant human angiopoietin-1* (ANG1*; Regeneron Pharmaceuticals, Tarrytown, N.Y.). After 9 rounds of SELEX, the pool was cloned and sequenced, and a single random region sequence (ANG9-4-SEQ ID NO:151) was identified:

ACUCGAACAUUUCCACUAACCAACCAUACUAAAGCACCGC.

Figure 24:
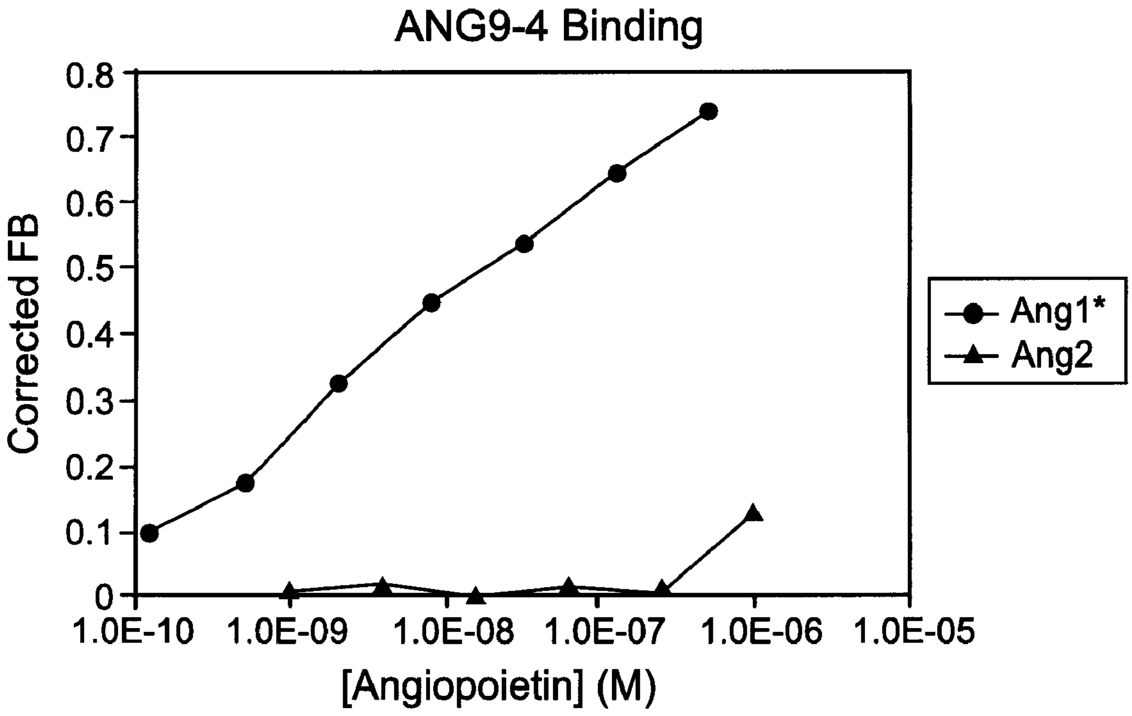
FIG. 24 is a line graph wherein direct binding (corrected fraction bound (FB)) of ANG9-4 RNA aptamer (SEQ ID NO:151) is plotted as a function of protein concentration. ANG9-4 binds Ang1 (solid circles) with a $K_d$ of ~10 nM and binds the related antagonist Ang2 with a $K_d$ of >1 μM (>100-fold specificity)(solid triangles).

In FIG. 24, direct binding (corrected fraction bound) of ANG9-4 RNA is plotted as a function of protein concentration. ANG9-4 binds Ang1 with a $K_d$ of ~10 nM and binds the related antagonist Ang2 with a $K_d$ of >1 μM (>100-fold specificity). Additional data pertaining to Ang1 aptamers is presented in the Laboratory Examples.

Table 7 sets forth additional representative Ang1 aptamers. Analysis of earlier SELEX rounds revealed several unique clones with random region sequences bearing similarities to ANG9-4. Aptamer sequences are as follows: GGGAGAGAGGAAGAGGGAUGGG (SEQ ID NO:149)-$N_{40}$ (SEQ ID NO: 150)
CAUAACCCAGAGGUCGAUAGUACUGGAUCCCCCC.

TABLE 7

Ang1 Aptamers

| SEQ ID NO: | Clone - SELEX round number and specie | Random region ($N_{40}$) |
|---|---|---|
| 152 | 9-4 | ACUCGAACAUUUCCACUAACCAACCAUACUAAAGCACCGC |
| 153 | 7-2 | GACCACCAACACACCACAUACUGCUUUGUACCAACAUUC |
| 154 | 6-1 | CCCAGCGAACACACAACAGAACACGAACGGAUCCGAGCAA |
| 155 | 6-2 | GUCACAAACUACCUUCAUCCUUCGCUUGAUACAACAUUC |
| 156 | 6-7 | ACACCAAGGACCCAACGACCCUCGCUUGACACAGUCAUUC |
| 157 | 6-8 | AUGAACAACACCCAAACUUGCUUCAACCGCAUCCACA |
| 158 | 6-11 | GACCUCACGCACUGCUAAGCGGCUCUGAUGGAGCUCUAUG |
| 159 | 6-13 | CCACCUCCGAAAAAUCACAAUCUGCCCUUGACACCAGCUAG |
| 160 | 6-17 | CCUCAUUGGCCCUGCCACGCUCGGACAACCGUUCCGCUCA |
| 161 | 6-21 | UCCAGUGCAGUUCCAUAACCGCUACUCAGCGCGUGAUUAG |

TABLE 7-continued

Ang1 Aptamers

| SEQ ID NO: | Clone - SELEX round number and specie | Random region ($N_{40}$) |
|---|---|---|
| 162 | 6-22 | UUUCGAGCAACCUCCCAACAAUCUAACCGUAACCCUCCAG |
| 163 | 6-27 | CAACAUCAGCACGCCUGAACCUUCGCUUGCAACAGCAUUC |
| 164 | 6-29 | CCACCUCCGAAAAAUCACAAUCUGCCCUUGACACCAGCUAG |
| 165 | 6-31 | UUACACCAUCGACCAAACUAUGCGCCGUACCACUAUACGA |

For Angiopoietin-2 (Ang2) Aptamers, a random library of 2'-fluoro modified RNA was created with the sequence:

GGGAGGACGAUGCGG (SEQ ID NO:166) —$N_{40}$—CAGACGACUCGCUGAGGAUCCGAGA (SEQ ID NO:167).

Figure 27:
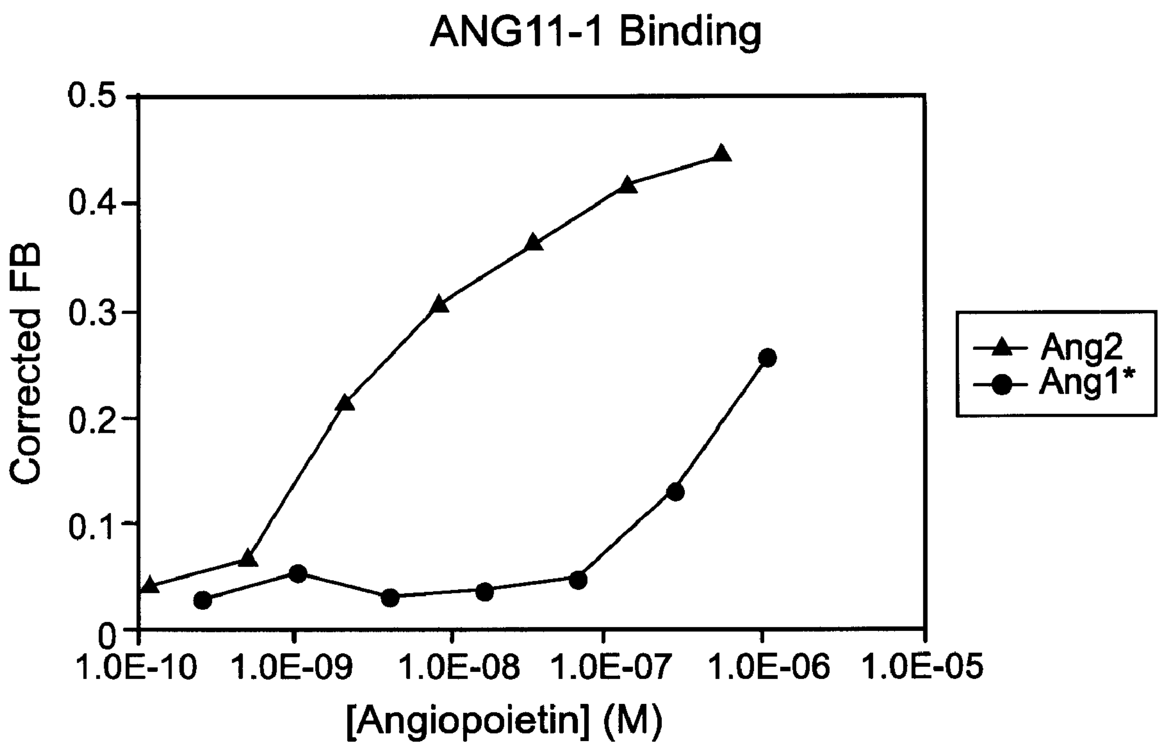
FIG. 27 is a line graph wherein direct binding (corrected fraction bound (FB)) of ANG11-1 RNA is plotted as a function of protein concentration. ANG11-1 binds Ang2 (solid triAngles) with a $K_d$ of <10 nM and binds Ang1* with a $K_d$ of ~1 μM (>100-fold specificity)(solid circles).

In vitro selection was performed using recombinant human angiopoietin-2 (Ang2; R&D Systems, Minneapolis, Minn.). To enhance the specificity of the Ang2 selection, molecules that bound the related agonist Angiopoietin-1* (Ang1*; Regeneron Pharmaceuticals) were discarded (negative selection) prior to rounds of positive selection for Ang2. After 11 rounds, the pool was cloned and sequenced, and a family of RNAs with a 12-nucleotide consensus region (italics) was identified and was represented by one dominant random region sequence (ANG11-1): ACUAGCCUCAUCAGCU-CAUG UGCCCCUCCGCCUGGAUCAC (SEQ ID NO:168). As shown in FIG. 27, direct binding (corrected fraction bound) of ANG11-1 RNA is plotted as a function of protein concentration. ANG11-1 binds Ang2 with a $K_d$ of <10 nM and binds Ang1* with a $K_d$ of ~1 μM (>100-fold specificity).

Table 8 sets forth additional representative Ang2 aptamers. Analysis of clones from rounds 9 and 11 revealed several unique random region sequences containing at least one of two conserved motifs, indicated by italics or underlining. Aptamer sequences are as follows: GGGAGGACGAUGCGG (SEQ ID NO:166) —$N_{40}$—CAGACGACUCGCUGAGGAUCCGAGA (SEQ ID NO:167).

TABLE 8

Ang2 Aptamers

| SEQ ID NO: | Clone - SELEX round number and specie | Random region ($N_{40}$) | Frequency | $K_d$ |
|---|---|---|---|---|
| 168 | 11-1 | ACUAGCCU*CAUCAGCUCAUG*UGCCCCUCCGCCUGGAUCAC | 10 of 26 | ~5 nM |
| 169 | 11-2 | UGACCAAGCCU<u>CACGUUGAAC</u>CUGCCAGUAGACCCCGCCCA | 1 of 26 | |
| 170 | 11-3 | UUAAC*CAUCAGCUCAUG*GCCCCUGCCCUCUCAAGGACCAC | 1 of 26 | ~10 nM |

TABLE 8-continued

Ang2 Aptamers

| SEQ ID NO: | Clone - SELEX round number and specie | Random region ($N_{40}$) | Fre-quency | $K_d$ |
|---|---|---|---|---|
| 171 | 11-4 | CACCAGACCGA*CAUCAGC*UUAUGGCCCCUCACCCACA CCG | 1 of 26 | |
| 172 | 11-6 | GGAGCGCAAUUCGCCUCGCAAGUUGAACUCCGCUGG CGG | 1 of 26 | |
| 173 | 11-9 | UAA*GCUC*UUUGGCUUAGCCCGACACGUUGAACUCCA GAGU | 1 of 26 | |
| 174 | 11-10 | CACGGUACCACCAAGUCACACGUUGAACUCCAUGCA GCUG | 1 of 26 | |
| 175 | 11-15 | CCACCGAUCG*CAUCAGCUCAU*GGCCCCUCCCGACCC GCCA | 1 of 26 | |
| 176 | 11-19 | CCAGACGUUCUCGCCCCGCCGAUCAUCAGCGCUGGC CCUAU | 1 of 26 | |
| 177 | 11-26 | CACUACCACGCCAU*AUCAGCU*AAUGGCCCCUCCCUA CGCA | 1 of 26 | |
| 178 | 11-30 | CACUCAGCGCCCUGCGAAACGUUGCCGCCUCCCAAC GUCU | 1 of 26 | |
| 179 | 11-32 | ACUCACCAGUCACC*AUCAGCUCAUG*CGCCCCUCCCC CGAC | 1 of 26 | |
| 180 | 11-34 | CUCUUUUUGUCCCCGCACGUUGAACUCCUGUCCCUC UACU | 1 of 26 | |
| 181 | 11-36 | UGACGGUUCUUCUCUCGCCUCUGG*AGCUCU*CGUCUC GAU | 2 of 26 | |
| 182 | 9-1 | CACUUUA GCUCACGCCACCGCACGUUGAACGCCCA UCCCG | 1 of 8 | |
| 183 | 9-2 | CAAUGCAG*CAUCAGCUCAU*GGCCCCUCCACAAGCGC GAAU | 1 of 8 | |
| 184 | 9-3 | CAUGUCUACAACAAUCUCGCCCGUUGAGUCUCGUCG AAUU | 2 of 8 | |
| 185 | 9-5 | CGAU CU UU UCGUCAACCGCACGUUGAACUCGGC UCGGCAC | 1 of 8 | ~5 nM |
| 186 | 9-6 | CACCCGUCCGUCCAAAUCCGCUUCGUUGGACCCCAU CUU | 1 of 8 | |

Figure 30:
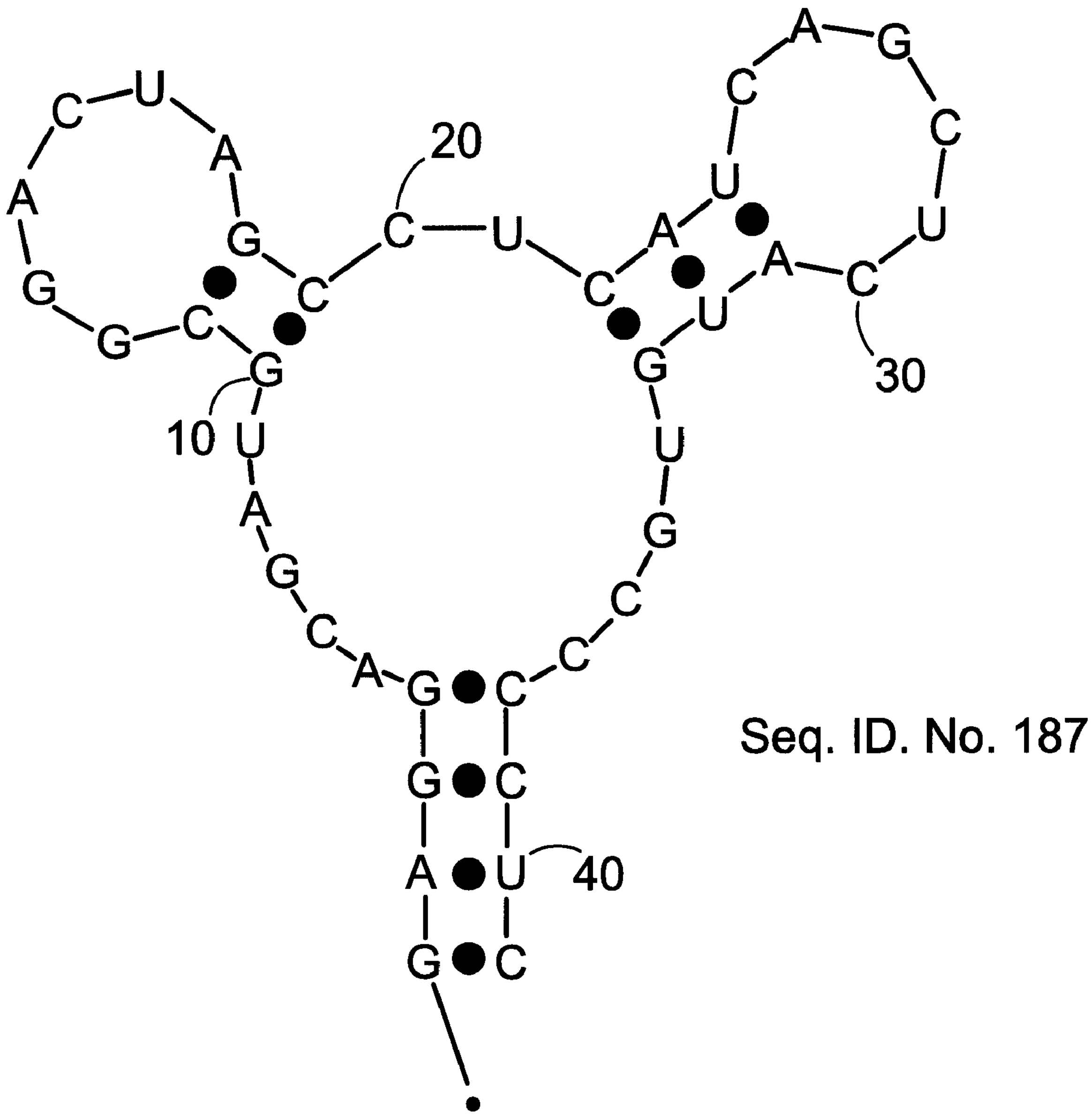
FIG. 30 is a secondary structure schematic of ANG11-1.41, prepared via application of sequence alignment and RNA-folding algorithms to the predominant sequence family suggests a common stem-looped structure, which incorporated the conserved sequence motif. Scrambling the 6-nucleotide consensus loop sequence (CAGCUC>ACUCCG) disrupts the ability of the truncate to bind Ang2 ($K_d$>1000 nM), as does mutation of the sequence comprising the terminal stem (($K_d$~1000 nM).

Referring now to FIG. 30, application of sequence alignment and RNA-folding algorithms to the predominant sequence family suggests a common stem-looped structure that incorporated the conserved sequence motif. Shown is a truncated form (dubbed 11-1.41) of the above-noted aptamer 11.1 (SEQ ID NO:168). The sequence of 11-1.41 is GAGGACGAUGCGGACUAGCCUCAUCAGCU-CAUGUGCCCCUC (SEQ ID NO: 187). Scrambling the 6-nucleotide consensus loop sequence (CAGCUC>ACUCCG) disrupts the ability of the truncate to bind Ang2 ($K_d$>1000 nM), as does mutation of the sequence comprising the terminal stem (($K_d$~1000 nM).

II.G. General Considerations for Aptamers

When a consensus sequence is identified, oligonucleotides that contain that sequence can be made by conventional synthetic or recombinant techniques. These aptamers can also function as target-specific aptamers of this invention. Such an aptamer can conserve the entire nucleotide sequence of an isolated aptamer, or can contain one or more additions, deletions or substitutions in the nucleotide sequence, as long as a consensus sequence is conserved. A mixture of such aptamers can also function as target-specific aptamers, wherein the mixture is a set of aptamers with a portion or portions of their nucleotide sequence being random or varying, and a conserved region that contains the consensus sequence. Additionally, secondary aptamers can be synthesized using one or more of the modified bases, sugars and linkages described herein using conventional techniques and those described herein.

In some embodiments of this invention, aptamers can be sequenced or mutagenized to identify consensus regions or domains that are participating in aptamer binding to target, and/or aptamer structure. This information is used for generating second and subsequent pools of aptamers of partially known or predetermined sequence. Sequencing used alone or in combination with the retention and selection processes of this invention, can be used to generate less diverse oligonucleotide pools from which aptamers can be made. Further selection according to these methods can be carried out to generate aptamers having preferred characteristics for diagnostic or therapeutic applications. That is, domains that facilitate, for example, drug delivery could be engineered into the aptamers selected according to this invention.

Although this invention is directed to making aptamers using screening from pools of non-predetermined sequences of oligonucleotides, it also can be used to make second-generation aptamers from pools of known or partially known sequences of oligonucleotides. A pool is considered diverse even if one or both ends of the oligonucleotides comprising it are not identical from one oligonucleotide pool member to another, or if one or both ends of the oligonucleotides comprising the pool are identical with non-identical intermediate regions from one pool member to another. Toward this objective, knowledge of the structure and organization of the target protein can be useful to distinguish features that are important for biochemical pathway inhibition or biological response generation in the first generation aptamers. Structural features can be considered in generating a second (less random) pool of oligonucleotides for generating second round aptamers.

Those skilled in the art will appreciate that comparisons of the complete or partial amino acid sequences of the purified protein target to identify variable and conserved regions is useful. Comparison of sequences of aptamers made according to this invention provides information about the consensus regions and consensus sequences responsible for binding. It is expected that certain nucleotides will be rigidly specified and certain positions will exclusively require certain bases. Likewise, studying localized regions of a protein to identify secondary structure can be useful. Localized regions of a protein can adopt a number of different conformations including beta strands, alpha helices, turns (induced principally by proline or glycine residues) or random structure. Different regions of a polypeptide interact with each other through hydrophobic and electrostatic interactions and also by formation of salt bridges, disulfide bridges, etc. to form the secondary and tertiary structures. Defined conformations can be formed within the protein organization, including beta sheets, beta barrels, and clusters of alpha helices.

It sometimes is possible to determine the shape of a protein target or portion thereof by crystallography X ray diffraction or by other physical or chemical techniques known to those skilled in the art. Many different computer programs are available for predicting protein secondary and tertiary structure, the most common being those described in Chou, P. Y. and Fasman, G. D. (1978) *Biochemistry,* 13:222-245, and Gamier et al. (1978) *J. Mol. Biol.,* 120:97-120. Generally, these and other available programs are based on the physical and chemical properties of individual amino acids (hydrophobicity, size, charge and presence of side chains) and on the amino acids' collective tendency to form identifiable structures in proteins whose secondary structure has been determined. Many programs attempt to weight structural data with their known influences. For example, amino acids such as proline or glycine are often present where polypeptides have share turns. Long stretches of hydrophobic amino acids (as determined by hydropathy plot), usually have a strong affinity for lipids.

Data obtained by the methods described above and other conventional methods and tools can be correlated with the presence of particular sequences of nucleotides in the first and second generation aptamers to engineer second and third generation aptamers. Further, according to this invention, second generation aptamers can be identified simply by sequentially screening from pools of oligonucleotides having more predetermined sequences than the pools used in earlier rounds of selection.

These methods can be used to design optimal binding sequences for any desired protein target (which can be portions of aptamers or entire aptamers) and/or to engineer into aptamers any number of desired targeted functions or features. Optimal binding sequences will be those which exhibit high relative affinity for target, i.e., affinity measured in $K_d$ in at least in the nanomolar range, and, for certain drug applications, the nanomolar or picomolar range. In practicing this invention, studying the binding energies of aptamers using standard methods known generally in the art can be useful generally, consensus regions can be identified by comparing the conservation of nucleotides for appreciable enhancement in binding.

Structural knowledge can be used to engineer aptamers made according to this invention. For example, stem structures in the aptamer pool can be vital components in some embodiments where increased aptamer rigidity is desired. According to the teachings of the instant invention, a randomly generated pool of oligonucleotides having the stem sequences can be generated. After aptamers are identified which contain the stem (i.e., use the stem in primers), one can put cross-linkers in the stem to covalently fix the stem in the aptamer structure. Cross-linkers also can be used to fix an aptamer to a target.

Once an aptamer has been identified, it can be used, either by linkage to, or use in combination with, other aptamers identified according to these methods. One or more aptamers can be used in this manner to bind to one or more targets.

II.G.1. Techniques for Identifying Improved Nucleic Acid Ligands

In order to produce nucleic acids desirable for use as a pharmaceutical, it is preferred that the nucleic acid ligand binds to the target in a manner capable of achieving the desired effect on the target; be as small as possible to obtain the desired effect; be as stable as possible; and be a specific ligand to the chosen target. In most, if not all, situations it is preferred that the nucleic acid ligand has the highest possible affinity to the target. Modifications or derivatizations of the ligand that confer resistance to degradation and clearance in situ during therapy, the capability to cross various tissue or cell membrane barriers, or any other accessory properties that do not significantly interfere with affinity for the target molecule can also be provided as improvements.

One of the uses of nucleic acid ligands derived by SELEX or another approach is to find ligands that alter target molecule function. Thus, it is a good procedure to first assay for inhibition or enhancement of function of the target protein. One could even perform such functional tests of the combined ligand pool prior to cloning and sequencing. Assays for the biological function of the chosen target are generally available and known to those skilled in the art, and can be easily performed in the presence of the nucleic acid ligand to determine if inhibition occurs.

Enrichment will supply a number of cloned ligands of probable variable affinity for the target molecule. Sequence comparisons can yield consensus secondary structures and primary sequences that allow grouping of the ligand sequences into motifs. Although a single ligand sequence (with some mutations) can be found frequently in the total population of cloned sequences, the degree of representation of a single ligand sequence in the cloned population of ligand sequences cannot absolutely correlate with affinity for the target molecule. Therefore mere abundance is not the sole criterion for judging "winners" after SELEX and binding assays for various ligand sequences (adequately defining each motif that is discovered by sequence analysis) are required to weigh the significance of the consensus arrived at by sequence comparisons. The combination of sequence comparison and affinity assays should guide the selection of candidates for more extensive ligand characterization.

An important avenue for narrowing down what amount of sequence is relevant to specific affinity is to establish the boundaries of that information within a ligand sequence. This is conveniently accomplished by selecting end-labeled fragments from hydrolyzed pools of the ligand of interest so that 5' and 3' boundaries of the information can be discovered. To determine a 3' boundary, one can perform a large-scale in vitro transcription of the PCR'd ligand, gel purifies the RNA using UV shadowing on an intensifying screen, phosphatases the purified RNA, phenol extracts extensively, labels by kinasing with $^{32}P$, and gel purifies the labeled product (using a film of the gel as a guide). The resultant product can then be subjected to pilot partial digestions with RNase T1 (varying enzyme concentration and time, at 50° C. in a buffer of 7M urea, 50 mM sodium citrate pH 5.2) and alkaline hydrolysis (at 50 mM $NaCO_3$, adjusted to pH 9.0 by prior mixing of 1M bicarbonate and carbonate solutions; test over ranges of 20 to 60 minutes at 95° C.). Once optimal conditions for alkaline hydrolysis are established (so that there is an even distribution of small to larger fragments) one can scale up to provide enough material for selection by the target (usually on nitrocellulose filters).

One then sets up binding assays, varying target protein concentration from the lowest saturating protein concentration to that protein concentration at which approximately 10% of RNA is bound as determined by the binding assays for the ligand. One should vary target concentration (if target supplies allow) by increasing volume rather than decreasing absolute amount of target; this provides a good signal to noise ratio as the amount of RNA bound to the filter is limited by the absolute amount of target. The RNA is eluted as, for example, in SELEX and then run on a denaturing gel with T1 partial digests so that the positions of hydrolysis bands can be related to the ligand sequence.

The 5' boundary can be similarly determined. Large-scale in vitro transcriptions are purified as described above. There are two methods for labeling the 3' end of the RNA. One method is to kinase Cp with $^{32}P$ (or purchase $^{32}P$—Cp) and ligate to the purified RNA with RNA ligase. The labeled RNA is then purified as above and subjected to very identical protocols. An alternative is to subject unlabeled RNAs to partial alkaline hydrolyses and extend an annealed, labeled primer with reverse transcriptase as the assay for band positions. One of the advantages over pCp labeling is the ease of the procedure, the more complete sequencing ladder (by dideoxy chain termination sequencing) with which one can correlate the boundary, and increased yield of assayable product. A disadvantage is that the extension on eluted RNA sometimes contains artifactual stops, so it can be important to control by spotting and eluting starting material on nitrocellulose filters without washes and assaying as the input RNA.

The result is that it is possible to find the boundaries of the sequence information required for high affinity binding to the target.

II.G.2. Assessment of Nucleotide Contributions to Affinity

Once a minimal high affinity ligand sequence is identified, it can be useful to identify the nucleotides within the boundaries that are crucial to the interaction with the target molecule. One method is to create a new random template in which all of the nucleotides of a high affinity ligand sequence are partially randomized or blocks of randomness are interspersed with blocks of complete randomness for use in a SELEX method for example, preferably a modified or toggle SELEX method as disclosed herein. Such "secondary" SELEXes produce a pool of ligand sequences in which crucial nucleotides or structures are absolutely conserved, less crucial features preferred, and unimportant positions unbiased. Secondary SELEXes can thus help to further elaborate a consensus that is based on relatively few ligand sequences. In addition, even higher-affinity ligands can be provided whose sequences were unexplored in the original SELEX.

Another method is to test oligo-transcribed variants (i.e. nucleotide substitution) where the consensus sequence can be unclear.

Another useful set of techniques are inclusively described as chemical modification experiments. Such experiments can be used to probe the native structure of RNAs, by comparing modification patterns of denatured and non-denatured states. The chemical modification pattern of an RNA ligand that is subsequently bound by target molecule can be different from the native pattern, indicating potential changes in structure upon binding or protection of groups by the target molecule. In addition, RNA ligands will fail to be bound by the target molecule when modified at positions crucial to either the bound structure of the ligand or crucial to interaction with the target molecule. Such experiments in which these positions are identified are described as "chemical modification interference" experiments.

There are a variety of available reagents to conduct such experiments that are known to those skilled in the art (see, Ehresmann et al., *Nuc. Acids. Res.,* 15:9109-9128, (1987)). Chemicals that modify bases can be used to modify ligand RNAs. A pool is bound to the target at varying concentrations and the bound RNAs recovered (much as in the boundary experiments) and the eluted RNAs analyzed for the modification. An assay can be by subsequent modification-dependent base removal and aniline scission at the baseless position or by reverse transcription assay of sensitive (modified) positions. In such assays bands (indicating modified bases) in unselected RNAs appear that disappear relative to other bands in target protein-selected RNAs. Similar chemical modifications with ethylnitrosourea, or via mixed chemical or enzymatic synthesis with, for example, 2'-methoxys on ribose or phosphorothioates can be used to identify essential atomic groups on the backbone. In experiments with 2'-methoxy vs. 2'-OH mixtures, the presence of an essential OH group results in enhanced hydrolysis relative to other positions in molecules that have been stringently selected by the target.

Comparisons of the intensity of bands for bound and unbound ligands can reveal not only modifications that interfere with binding, but also modifications that enhance binding. A ligand can be made with precisely that modification and tested for the enhanced affinity. Thus chemical modification experiments can be a method for exploring additional local contacts with the target molecule, just as "walking" (see below) is for additional nucleotide level contacts with adjacent domains.

A consensus of primary and secondary structures that enables the chemical or enzymatic synthesis of oligonucleotide ligands whose design is based on that consensus is provided herein via a SELEX method, preferably a modified or toggle SELEX method as disclosed herein. Because the replication machinery of SELEX requires that rather limited variation at the subunit level (ribonucleotides, for example), such ligands imperfectly fill the available atomic space of a target molecule's binding surface. However, these ligands can be thought of as high-affinity scaffolds that can be derivatized to make additional contacts with the target molecule. In addition, the consensus contains atomic group descriptors that are pertinent to binding and atomic group descriptors that are coincidental to the pertinent atomic group interactions. Such derivatization does not exclude incorporation of cross-linking agents that will give specifically directly covalent linkages to the target protein. Such derivatization analyses can be performed at but are not limited to the 2' position of the ribose, and thus can also include derivatization at any position in the base or backbone of the nucleotide ligand.

The present invention thus includes nucleic acid ligands wherein certain chemical modifications have been made in order to increase the in vivo stability of the ligand or to enhance or mediate the delivery of the ligand. Examples of such modifications include chemical substitutions at the ribose and/or phosphate positions of a given RNA sequence. See, e.g., Cook et al., PCT Application WO 9203568; U.S. Pat. No. 5,118,672 to Schinazi et al.; Hobbs et al., *Biochem* 12:5138 (1973); Guschlbauer et al., *Nucleic Acids Res.* 4:1933 (1977); Shibahara et al., *Nucl. Acids. Res.* 15:4403 (1987); Pieken et al., *Science* 253:314 (1991), each of which is specifically incorporated herein by reference.

A logical extension of this analysis is a situation in which one or a few nucleotides of the polymeric ligand is used as a site for chemical derivative exploration. The rest of the ligand serves to anchor in place this monomer (or monomers) on which a variety of derivatives are tested for non-interference with binding and for enhanced affinity. Such explorations can result in small molecules that mimic the structure of the initial ligand framework, and have significant and specific affinity for the target molecule independent of that nucleic acid framework. Such derivatized subunits, which can have advantages with respect to mass production, therapeutic routes of administration, delivery, clearance or degradation than the initial ligand, can become the therapeutic and can retain very little of the original ligand. Thus, the aptamer ligands of the present invention can allow directed chemical exploration of a defined site on the target molecule known to be important for the target function.

II.G.3. Walking Experiments

After a minimal consensus ligand sequence has been determined for a given target, it is possible to add random sequence to the minimal consensus ligand sequence and evolve additional contacts with the target, perhaps to separate but adjacent domains. This procedure has been referred to in the art as "walking".

A walking experiment can involve two experiments performed sequentially. A new candidate mixture is produced in which each of the members of the candidate mixture has a fixed nucleic acid region that corresponds to a nucleic acid ligand of interest. Each member of the candidate mixture also contains a randomized region of sequences. According to this method it is possible to identify what are referred to as "extended" nucleic acid ligands, which contain regions that can bind to more than one binding domain of a target.

II.G.4. Covariance Analysis

In conjunction with empirical methods for determining the three dimensional structure of nucleic acids, computer modeling methods for determining structure of nucleic acid ligands can also be employed.

Secondary structure prediction is a useful guide to correct sequence alignment. It is also a highly useful stepping-stone to correct 3D structure prediction, by constraining a number of bases into A-form helical geometry.

Tables of energy parameters for calculating the stability of secondary structures exist. Although early secondary structure prediction programs attempted to simply maximize the number of base-pairs formed by a sequence, most current programs seek to find structures with minimal free energy as calculated by these thermodynamic parameters. There are two problems in this approach that should be borne in mind. First, the thermodynamic rules are inherently inaccurate, typically to 10% or so, and there are many different possible structures lying within 10% of the global energy minimum. Second, the actual secondary structure need not lie at a global energy minimum, depending on the kinetics of folding and synthesis of the sequence. Nonetheless, for short sequences, these caveats are of minor importance because there are so few possible structures that can form.

The brute force predictive method is a dot-plot: make an N by N plot of the sequence against itself, and mark an X everywhere a base pair is possible. Diagonal runs of X's mark the location of possible helices. Exhaustive tree-searching methods can then search for all possible arrangements of compatible (i.e., non-overlapping) helices of length L or more; energy calculations can be done for these structures to rank them as more or less likely. The advantages of this method are that all possible topologies, including pseudoknotted conformations, can be examined, and that a number of suboptimal structures are automatically generated as well. The disadvantages of the method are that it can run in the worst cases in time proportional to an exponential factor of the sequence size, and cannot (depending on the size of the sequence and the actual tree search method employed) look deep enough to find a global minimum.

An elegant predictive method, and currently the most used, is the Zuker program. Zuker (1989) *Science* 244:48-52. Originally based on an algorithm developed by Ruth Nussinov, the Zuker program makes a major simplifying assumption that no pseudoknotted conformations will be allowed. This permits the use of a dynamic programming approach that runs in time proportional to only N3 to N4, where N is the length of the sequence. The Zuker program is the only program capable of rigorously dealing with sequences of than a few hundred nucleotides, so it has come to be the most commonly used by biologists. However, the inability of the Zuker program to predict pseudoknotted conformations is a serious consideration. Where pseudoknotted RNA structures are suspected or are recognized by eye, a brute-force method capable of predicting pseudoknotted conformations should be employed.

A central element of comparative sequence analysis is sequence covariations. A covariation is when the identity of one position depends on the identity of another position; for instance, a required Watson-Crick base pair shows strong covariation in that knowledge of one of the two positions gives absolute knowledge of the identity at the other position. Covariation analysis has been used previously to predict the secondary structure of RNAs for which a number of related sequences sharing a common structure exist, such as tRNA, rRNAs, and group I introns. It is now apparent that covariation analysis can be used to detect tertiary contacts as well.

Stormo and Gutell (1992) *Nucleic Acids Research* 29:5785-5795 have designed and implemented an algorithm that precisely measures the amount of covariations between two positions in an aligned sequence set. The program is called "MIXY"-Mutual Information at position X and Y. Consider an aligned sequence set. In each column or position, the frequency of occurrence of A, C, G, U, and gaps is calculated. Call this frequency f(bx), the frequency of base b in column x. Now consider two columns at once. The frequency that a given base b appears in column x is f(bx) and the frequency that a given base b appears in column y is f(by). If position x and position y do not care about each other's identity—that is, the positions are independent; there is no covariation—the frequency of observing bases bx and by at position x and y in any given sequence should be just f(bxby)=f(bx)f(by). If there are substantial deviations of the observed frequencies of pairs from their expected frequencies, the positions are said to covary.

The amount of deviation from expectation can be quantified with an information measure M(x,y), the mutual information of x and y:

$$M(x, y) = \sum_{b_x b_y} f(b_x b_y) \ln \frac{f(b_x b_y)}{f(b_x) f(b_y)}$$

M(x,y) can be described as the number of bits of information one learns about the identity of position y from knowing just the identity of position y from knowing just the identity of position x. If there is no covariation, M(x,y) is zero; larger values of M(x,y) indicate strong covariation. Covariation values can be used to develop three-dimensional structural predictions.

In some ways, the problem is similar to that of structure determination by NMR. Unlike crystallography, which in the end yields an actual electron density map, NMR yields a set of interatomic distances. Depending on the number of interatomic distances one can get, there can be one, few, or many 3D structures with which they are consistent. Mathematical techniques had to be developed to transform a matrix of interatomic distances into a structure in 3D space. The two main techniques in use are distance geometry and restrained molecular dynamics.

Distance geometry is the more formal and purely mathematical technique. The interatomic distances are considered to be coordinates in an N-dimensional space, where N is the number of atoms. In other words, the "position" of an atom is specified by N distances to all the other atoms, instead of the three (x,y,z) coordinates typically considered. Interatomic distances between every atom are recorded in an N-by-N distance matrix. A complete and precise distance matrix is easily transformed into a 3 by N Cartesian coordinates, using matrix algebra operations. The trick of distance geometry as applied to NMR is dealing with incomplete (only some of the interatomic distances are known) and imprecise data (distances are known to a precision of only a few angstroms at best). Much of the time of distance geometry-based structure calculation is thus spent in pre-processing the distance matrix, calculating bounds for the unknown distance values based on the known ones, and narrowing the bounds on the known ones. Usually, multiple structures are extracted from the distance matrix that are consistent with a set of NMR data; if they all overlap nicely, the data were sufficient to determine a unique structure. Unlike NMR structure determination, covariance gives only imprecise distance values, but also only probabilistic rather than absolute knowledge about whether a given distance constraint should be applied.

Restrained molecular dynamics can also be employed, albeit in a more ad hoc manner. Given an empirical force field that attempts to describe the forces that all the atoms feel (van der Weals, covalent bonding lengths and Angles, electrostatics), one can simulate a number of femtosecond time steps of a molecule's motion, by assigning every atom at a random velocity (from the Boltzmann distribution at a given temperature) and calculating each atom's motion for a femtosecond using Newtonian dynamical equations; that is "molecular dynamics". In restrained molecular dynamics, one assigns extra ad hoc forces to the atoms when they violate specified distance bounds.

With respect to RNA aptamers, the probabilistic nature of data with restrained molecular dynamics can be addressed. The covariation values can be transformed into artificial restraining forces between certain atoms for certain distance bounds; varying the magnitude of the force according to the magnitude of the covariance.

NMR and covariance analysis generates distance restraints between atoms or positions, which are readily transformed into structures through distance geometry or restrained molecular dynamics. Another source of experimental data which can be utilized to determine the three dimensional structures of nucleic acids is chemical and enzymatic protection experiments, which generate solvent accessibility restraints for individual atoms or positions.

II.H. Utility of the Aptamers

The aptamers and modified aptamers of the invention are useful in diagnostic, research and therapeutic contexts. For diagnostic applications, aptamers are particularly well suited for binding to biomolecules that are identical or similar between different species. Classes of molecules such as coagulation factors and transcription factors generally do not serve as good antigens because they are not easily recognized as foreign by the immune systems of animals that can be used to generate antibodies. Antibodies are generally used to bind analytes that are detected or quantitated in various diagnostic assays. Aptamers represent a class of molecules that can be used in place of antibodies for diagnostic and purification purposes.

The aptamers of the invention are therefore particularly useful as diagnostic reagents to detect the presence or absence of the target substances to which they specifically bind. Such diagnostic tests are conducted by contacting a sample with the specifically binding oligonucleotide to obtain a complex that is then detected by conventional techniques. For example, the aptamers can be labeled using radioactive, fluorescent, or chromogenic labels and the presence of label bound to solid support to which the target substance has been bound through a specific or nonspecific binding means detected. Alternatively, the specifically binding aptamers can be used to effect initial compiexation to the support. Techniques for conducting assays using such oligomers as specific binding partners are generally known to track those for standard specific binding partner based assays.

This invention also permits the recovery and deduction of oligomeric sequences that bind specifically to target proteins and specific portions thereof. Therefore, these oligonucleotides can be used as a separation tool for retrieving the substances to which they specifically bind. By coupling the oligonucleotides containing the specifically binding sequences to a solid support, for example, proteins or other cellular components to which they bind can be recovered in useful quantities. In addition, these oligonucleotides can be used in diagnosis by employing them in specific binding assays for the target substances. When suitably labeled using detectable moieties such as radioisotopes, the specifically binding oligonucleotides can also be used for in vivo imaging or histological analysis.

It can be commented that the mechanism by which the specifically binding oligomers of the invention interfere with or inhibit the activity of a target substance is not always established, and is not a part of the invention. The oligomers of the invention are characterized by their ability to target specific substances regardless of the mechanisms of targeting or the mechanism of the effect thereof.

For use in research, the specifically binding oligonucleotides of the invention are especially helpful in effecting the isolation and purification of substances to which they bind. For this application, typically, the oligonucleotide containing the specific binding sequences is conjugated to a solid support and used as an affinity ligand in chromatographic separation of the target substance. The affinity ligand can also be used to recover previously unknown substances from sources that do not contain the target substance by virtue of binding similarity between the intended target and the unknown substances. Furthermore, as data accumulate with respect to the nature of the nonoligonucleotide/oligonucleotide-specific binding, insight can be gained as to the mechanisms for control of gene expression.

The aptamers described herein can be used as a separation reagent for retrieving the targets to which they specifically bind. By coupling the oligonucleotides containing the specifically binding sequences to a solid support, for example, the target substances can be recovered in useful quantities. In addition, these oligonucleotides can be used in diagnosis by employing them in specific binding assays for the target substances. When suitably labeled using detectable moieties including radioisotopes such as $^{19}F$, $^{99M}Tc$, $^{131}I$, $^{90}Y$, $^{111}In$, $^{123}I$, $^{15}N$, $^{32}$ or $^{33}P$, the specifically binding oligonucleotides can also be used for in vivo or in vitro diagnosis, imaging or histological analysis by techniques known in the art.

For application in such various uses, the aptamers of the invention can be coupled to auxiliary substances that enhance or complement the function of the aptamer. Such auxiliary substances include, for example, labels such as radioisotopes, fluorescent labels, enzyme labels and the like; specific binding reagents such as antibodies, additional aptamer sequence, cell surface receptor ligands, receptors per se and the like; toxins such as *diphtheria toxin, tetanus toxin* or *ricin*; drugs such as antiinflammatory, antibiotic, or metabolic regulator pharmaceuticals, solid supports such as chromatographic or electrophoretic supports, and the like. Suitable techniques for coupling of aptamers to desired auxiliary substances are generally known for a variety of such auxiliary substances, and the specific nature of the coupling procedure will depend on the nature of the auxiliary substance chosen. Coupling can be direct covalent coupling or can involve the use of synthetic linkers such as those marketed by Pierce Chemical Co., Rockford, Ill.

Thus, the aptamers or modified aptamers of the invention can be used alone in therapeutic applications or can be used as targeting agents to deliver pharmaceuticals or toxins to desired targets. The aptamers can be used in diagnostic procedures and advantageously in this application include label. They can be used as reagents to separate target molecules from contaminants in samples containing the target molecules in which application they are advantageously coupled to solid support.

III. SYNTHESIS OF RNA APTAMERS

In a representative embodiment of the present invention, an RNA aptamer is synthesized on a solid support column, using conventional techniques such as those described by Beaucage et al. (1981) *Tetrahedr. Letters* 22:1859-1862 and Sinha et al., (1984) *Nucleosides and Nucleotides* 3:157-171, both of which are incorporated by reference. The final DMT-group is removed from the resulting RNA aptamer. Alternately, if large-scale synthesis is used, the RNA aptamer can be made by scale-up of the solid support method or the RNA aptamer can be made by using solution phase techniques, particularly if the desired end-product is a relatively short oligonucleotide. A starting material for the synthesis process can be a 5'-non-tritylated RNA oligoribo-nucleotide or analog of the desired primary structure, which preferably can have protected bases, and which is preferably bound to a solid-support. Any conventionally used protecting groups can be used. Typically $N_6$-benzoyl is used for adenine, $N_4$-benzoyl for cytosine, $N_2$-isobutyryl for guanine and $_{N2}$-benzoyl for 2-amino purine. Other useful protecting groups include phenoxyacetyl (PAC) and t-butoxyacetyl (TAC). Conveniently, the more base labile protection groups should be used for the synthesis of the RNA or analog fragment; those of ordinary skill in the art know these groups. Such groups can help to prevent hydrolysis of the generated tri- or diphosphates, which are generally quite stable under basic conditions, but could be subject to some hydrolysis. Other envisioned modifications are disclosed in U.S. Pat. No. 6,011,020, incorporated herein by reference, and include but are not limited to the incorporation of bioavailability enhancing molecules such as PEG or cholesterol via a covalent linkage.

A capped RNA or analog of this invention can be of any length, the only limit being that of the synthesis technique employed to prepare the RNA or analog. Currently, a preferred length is ranges from approximately 15 to 100 bases, but with improvements in synthetic technology the length of the oligonucleotide is expected to increase. For purposes of this invention, it is preferred that the capped RNA or analog be less than approximately 100 bases in length, and preferably less than about 40 bases in length.

In addition, nucleoside analogs such as 2'-deoxy, 2'-halo, 2'-amino (not substituted or mono- or disubstituted), 2'-mono, di- or trihalomethyl, 2'-O-alkyl, 2'-O-halo-substituted alkyl, 2'-alkyl, azido, phosphorothioate, sulfhydryl, methylphosphonate, fluorescein, rhodamine, pyrene, biotin, xanthine, hypoxanthine, 2,6-diamino purine, 2-hydroxy-6-mercaptopurine and pyrimidine bases substituted at the 6-position with sulfur or 5 position with halo or $C_{1-5}$ alkyl groups, abasic linkers, 3'-deoxy-adenosine as well as other available "chain terminator" or "non-extendible" analogs (at the 3'-end of the RNA), and the like can be incorporated during the RNA synthesis. Further, various labels such as $^{32}P$ or $^{33}P$ and the like can likewise be incorporated during the synthesis, resulting in novel RNA analogs produced by this process. Other envisioned modifications are disclosed in U.S. Pat. No. 6,011,020, incorporated herein by reference, and include but are not limited to the incorporation of 3' caps, such an inverted DT cap, or an inverted abasic cap, or combination thereof.

IV. THERAPEUTIC METHODS

A method of modulating the biological activity of a coagulation pathway factor is provided in accordance with the present invention. In a preferred embodiment, the method comprises: (a) administering to a warm blooded vertebrate in need thereof an effective amount of an RNA aptamer that selectively binds a coagulation pathway factor, the RNA aptamer having a dissociation constant for the coagulation pathway factor of about 20 nM or less; and (b) modulating the biological activity of the coagulation pathway factor in the warm-blooded vertebrate through the administering of the RNA aptamer in step (a).

A method of treating cardiovascular disease in a warm-blooded vertebrate is also provided in accordance with the present invention. The method comprises administering an effective amount of an RNA aptamer that selectively binds a coagulation pathway factor, the RNA aptamer having a dissociation constant for the coagulation pathway factor of about 20 nM or less, to a vertebrate subject suffering from cardiovascular disease, whereby cardiovascular disease in the vertebrate subject is treated.

A method of modulating E2F activity in a warm-blooded vertebrate in which such modulation is desired is also provided. The method comprises: (a) administering to the warm-blooded vertebrate an effective amount of an RNA aptamer that selectively binds an E2F family member, the RNA aptamer having a dissociation constant for the E2F family member of about 20 nM or less; and (b) modulating E2F in the warm-blooded vertebrate through the administering of the RNA aptamer of step (a).

The patient treated in the present invention in its many embodiments is desirably a human patient, although it is to be understood that the principles of the invention indicate that the invention is effective with respect to all vertebrate species, including warm-blood vertebrates (e.g. birds and mammals), which are intended to be included in the term "patient". In this context, a mammal is understood to include any mammalian species in which treatment of cardiovascular disease is desirable, particularly agricultural and domestic mammalian species.

Contemplated is the treatment of mammals such as humans, as well as those mammals of importance due to being endangered (such as Siberian tigers), of economical importance (animals raised on farms for consumption by humans and/or social importance (animals kept as pets or in zoos) to humans, for instance, carnivores other than humans such as cats and dogs), swine (pigs, hogs, and wild board), ruminants (such as cattle, oxen, sheep, giraffes, deer goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans.

The present method for treating cardiovascular disease in a tissue contemplates contacting a tissue in which cardiovascular disease is occurring, or is at risk for occurring, with a composition comprising a therapeutically effective amount of an RNA aptamer capable of binding a coagulation factor. Thus, the method comprises administering to a patient a therapeutically effective amount of a physiologically tolerable composition containing the RNA aptamer.

The dosage ranges for the administration of the RNA aptamer depend upon the form of the modulator, and its potency, as described further herein, and are amounts large enough to produce the desired effect in which coagulation is modulated, which can correspondingly ameliorate cardiovascular disease and the symptoms of cardiovascular disease. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The individual physician in the event of any complication can also adjust the dosage.

A therapeutically effective amount is an amount of an RNA aptamer sufficient to produce a measurable modulation of coagulation in the tissue being treated, i.e., a coagulation-modulating amount, an E2F activity-modulating amount coagulation, and/or angiogenesis factor activity (e.g. Ang1 or Ang2 activity)-modulating amount. Modulation of coagulation, E2F activity, and/or angiogenesis factor activity (e.g. Ang1 or Ang2 activity) can be measured in situ by immunohistochemistry by methods disclosed in the Laboratory Examples, or by other methods known to one skilled in the art. By the term "modulate" and grammatical variations thereof, it is intended an increase, decrease, or other alteration of any or all biological activities or properties a target.

Insofar as a coagulation modulator, E2F modulator, or angiogenesis factor activity (e.g. Ang1 or Ang2 activity) modulator can take the form of RNA aptamers it is to be appreciated that the potency, and therefore an expression of a "therapeutically effective" amount can vary. However, as shown by the methods presented in the Laboratory Examples, one skilled in the art can readily assess the potency of a candidate RNA aptamer of this invention.

A preferred RNA aptamer has the ability to substantially bind to a target in solution at modulator concentrations of less than one (1) micromolar (μM), preferably less than 0.1 μM, and more preferably less than 0.01 μM. By "substantially" is meant that at least a 50 percent reduction in target biological activity is observed by modulation in the presence of the a target, and at 50% reduction is referred to herein as an $IC_{50}$ value.

The RNA aptamers of the present invention can be administered parenterally by injection or by gradual infusion over time. Although the tissue to be treated can typically be accessed in the body by systemic administration and therefore most often treated by intravenous administration of therapeutic compositions, other tissues and delivery techniques are provided where there is a likelihood that the tissue targeted contains the target molecule. Thus, an RNA aptamer of the present invention can be administered orally, topically to a vascular tissue, intravenously, intraperitoneally, intramuscularly, subcutaneously, intra-cavity, transdermally, and can be delivered by peristaltic techniques. Representative, non-limiting approaches for topical administration to a vascular tissue include (1) coating or impregnating a blood vessel tissue with a gel comprising an aptamer of the present invention, for delivery in vivo, e.g. by implanting the coated or impregnated vessel in place of a damaged or diseased vessel tissue segment that was removed or by-passed; (2) delivery via a catheter to a vessel in which delivery is desired; and (3) pumping an aptamer composition of the present invention into a vessel that is to be implanted into a patient.

The therapeutic compositions comprising an RNA aptamer polypeptide of the present invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

The present invention contemplates therapeutic compositions useful for practicing the therapeutic methods described herein. Therapeutic compositions of the present invention contain a physiologically tolerable carrier together with an RNA aptamer as described herein, dissolved or dispersed therein as an active ingredient. In a preferred embodiment, the therapeutic composition is not immunogenic when administered to a subject for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a patient without the production of undesirable physiological effects such as nausea, dizziness, gastric upset and the like.

Pharmaceutically useful compositions comprising an RNA aptamer of the present invention can be formulated according to known methods such as by the admixture of a pharmaceutically acceptable carrier. Examples of such carriers and methods of formulation can be found in *Remington's Pharmaceutical Sciences*. To form a pharmaceutically acceptable composition suitable for effective administration, such compositions will contain an effective amount of the aptamer. Such compositions can contain admixtures of more than one aptamer.

Therapeutic or prophylactic compositions of the invention are administered to an individual in amounts sufficient to modulate coagulation and/or to treat or prevent cardiovascular disease. The effective amount can vary according to a variety of factors such as the individual's condition, weight, sex and age. Other factors include the mode of administration. Generally, the compositions will be administered in dosages adjusted for body weight, e.g. dosages ranging from about 1 μg/kg body weight to about 1 mg/kg body weight.

As noted above, the pharmaceutical compositions can be provided to the individual by a variety of routes such orally, topically to a vascular tissue, intravenously, intraperitoneally, intramuscularly, subcutaneously, intra-cavity, transdermally, and can be delivered by peristaltic techniques. Representative, non-limiting approaches for topical administration to a vascular tissue include (1) coating or impregnating a blood vessel tissue with a gel comprising an aptamer of the present invention, for delivery in vivo, e.g. by implanting the coated or impregnated vessel in place of a damaged or diseased vessel tissue segment that was removed or by-passed; (2) delivery via a catheter to a vessel in which delivery is desired; and (3) pumping an aptamer composition of the present invention into a vessel that is to be implanted into a patient. Alternatively, the aptamer can be introduced into cells by microinjection, or by liposome encapsulation. Advantageously, aptamers of the present invention can be administered in a single daily dose, or the total daily dosage can be administered in several divided doses.

Aptamers can be particularly useful for the treatment of diseases where it is beneficial to inhibit coagulation, E2F activity, and/or angiogenesis factor activity (e.g. Ang1 or Ang2 activity), or prevent such activity from occurring. The pharmaceutical compositions are administered in therapeutically effective amounts, that is, in amounts sufficient to generate a coagulation-, E2F activity-, and/or angiogenesis factor activity (e.g. Ang1 or Ang2 activity)-modulating response, or in prophylactically effective amounts, that is in amounts sufficient to prevent a coagulation factor from acting in a coagulation cascade, to prevent an E2F activity-mediated response, or to prevent an angiogenesis factor activity (e.g. Ang1 or Ang2 activity)-mediated response. The therapeutically effective amount and prophylactically effective amount can vary according to the type of aptamer. The pharmaceutical composition can be administered in single or multiple doses.

Aptamers synthesized or identified according to the methods disclosed herein can be used alone at appropriate dosages defined by routine testing in order to obtain optimal modulation of coagulation, E2F activity, and/or angiogenesis factor activity (e.g. Ang1 or Ang2 activity) while minimizing any potential toxicity. In addition, co-administration or sequential administration of other agents can be desirable. For combination treatment with more than one active agent, where the active agents are in separate dosage formulations, the active agents can be administered concurrently, or they each can be administered at separately staggered times.

The dosage regimen utilizing the aptamers of the present invention is selected in accordance with a variety of factors including type, species, age, weight, sex and medical condition of the patient; the severity of the condition to be treated; the route of administration; the renal and hepatic function of the patient; and the particular aptamer employed. A physician of ordinary skill can readily determine and prescribe the effective amount of the aptamer required to prevent, counter or arrest the progress of the condition. Optimal precision in achieving concentrations of aptamer within the range that yields efficacy without toxicity requires a regimen based on the kinetics of the aptamer's availability to target sites. This involves a consideration of the distribution, equilibrium, and elimination of the aptamer.

In the methods of the present invention, the aptamers herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrup, suppositories, gels and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that can be employed include glycerin and the like. For parenteral administration, sterile suspensions and solutions are desired. Isotonic preparations that generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention can also be coupled with soluble polymers as targetable drug carriers. Such polymers can include polyvinyl-pyrrolidone, pyran copolymer, polyhydroxypropylmethacryl amidephenol, polyhydroxy-ethylaspartamidephenol, or polyethyl-eneoxidepolylysine substituted with palmitoyl residues. Furthermore, the compounds of the present invention can be coupled (preferably via a covalent linkage) to a class of biodegradable polymers useful in achieving controlled release of a drug, for example, polyethylene glycol (PEG), polylactic acid, poly-epsilon caprolactone, polyhydroxy butyric acid, polyorthoesters, polyacetals, polydihydro-pyrans, polycyanoacrylates and cross-linked or amphipathic block copolymers of hydrogels. Cholesterol and similar molecules can be linked to the aptamers to increase and prolong bioavailability.

V. METHODS OF IDENTIFYING APTAMERS

A method of identifying a ligand to a target from a candidate mixture of potential ligands is also provided in accordance with the present invention. Products, i.e. ligands, produced or identified by a method of the present invention are also provided.

In one embodiment the method preferably comprises: (a) preparing a candidate mixture of potential ligands; (b) contacting the candidate mixture with a target substrate in a lower stringency buffer, wherein ligands having increased affinity to the target relative to the candidate mixture bind to the target; (c) removing unbound candidate mixture; and (d) collecting the ligands that are bound to the target to produce a first collected ligand mixture. More preferably, the method further comprises: (e) contacting the first collected ligand mixture with the target in a higher stringency buffer, wherein ligands having increased affinity to the target relative to the first collected ligand mixture bind to the target; (1) removing unbound ligands; and (g) collecting the ligands that are bound to the target to produce a second collected ligand mixture to thereby identify ligands to the target. Even more preferably, ligands in the first or second collected ligand mixture are enriched or expanded by any suitable technique, e.g. amplification, prior to contacting the first collected ligand mixture with the target in the higher stringency buffer, after collecting the ligands that bound the target in the higher stringency buffer, or both. Optionally, the contacting and expanding or enriching steps are repeated as necessary to produce a desired ligand.

In an alternative embodiment, the method comprises: (a) immobilizing a target on a substrate; (b) preparing a candidate mixture of potential ligands; (c) passing the candidate mixture over the substrate in a lower stringency buffer, wherein ligands having increased affinity to the immobilized target relative to the candidate mixture bind to the immobilized target; (d) passing a wash buffer over the substrate to remove unbound candidate mixture; (e) passing an eluting buffer over the substrate to elute the ligands that are bound to the immobilized target to produce an eluted ligand mixture; (f) passing the eluted ligand mixture over a substrate comprising immobilized target in a higher stringency buffer, wherein ligands having increased affinity to the immobilized target relative to the eluted ligand mixture bind to the immobilized target; (g) passing a wash buffer over the substrate to remove unbound ligands; and (h) passing an eluting buffer over the substrate to elute the ligands that are bound to the immobilized target to thereby identify ligands to the target. With respect to the alternative embodiment, it also preferred that ligands in the eluted ligand mixture are enriched or expanded by any suitable technique, e.g. amplification, prior to contacting the eluted ligand mixture with the target in the higher stringency buffer, after eluting ligands that bound the target in the higher stringency buffer, or both. Optionally, the contacting and expanding or enriching steps are repeated as necessary to produce as desired ligand. Thus, it is possible that the second collected ligand mixture can comprise a single ligand.

The method is applicable to any target as defined herein for which a ligand is sought. Representative targets are also disclosed in U.S. Pat. Nos. 5,756,291 and 5,817,785 herein incorporated by reference. In a preferred embodiment, the method further comprises amplifying the eluted ligand to yield a ligand-enriched mixture, whereby a ligand to the target is identified. The ligand mixture can comprise a candidate mixture of any ligand as defined herein, including but not limited to nucleic acids. In this case, the candidate mixture of nucleic acids comprises single strand nucleic acids. The single stranded nucleic acids can comprise deoxyribonucleic acids.

Preferably, the single stranded nucleic acids are ribonucleic acids. In this case amplification can be accomplished, for example, via reverse transcriptase PCR reactions, as disclosed in U.S. Pat. No. 5,817,785, herein incorporated by reference. Optionally, the candidate mixture of nucleic acids can comprise 2'-modified ribonucleic acids. For example, the 2'-modified ribonucleic acids can comprise 2'-fluoro (2'-F) modified nucleic acids.

Representative wash and eluting buffers are disclosed in U.S. Pat. Nos. 5,475,096 and 5,861,254, each of which incorporated herein by reference. In a preferred embodiment of the present invention in which a test nucleic acid mixture is incubated with target protein, the nucleic acid/protein mixture is filtered through a nitrocellulose filter and washed with appropriate buffer to remove free nucleic acids. Protein/nucleic acids often remain bound to the filter. Filter washing procedure can be optimized to reduce background binding. Such optimization of the filter washing procedures is within the skill of the ordinary artisan.

Any suitable eluting buffer as would be apparent to one of ordinary skill in the art after reviewing the disclosure of the present invention presented herein can also be employed in the present inventive method. For example, with respect to nucleic acid ligands, in order to proceed to the amplification step, selected nucleic acids must be released from the target after partitioning. This process is preferably done without chemical degradation of the selected nucleic acids and preferably results in amplifiable nucleic acids. For example, selected RNA molecules can be eluted from nitrocellulose filters using a freshly made solution containing 200 μl of a 7M urea, 20 mM sodium citrate (pH 5.0), 1 mM EDTA solution combined with 500 μl of phenol (equilibrated with 0.1M sodium acetate pH 5.2). A solution of 200 μl 7M urea with 500 μl of phenol can also be employed. In this case, the eluted solution of selected RNA can then extracted with ether, ethanol precipitated, and the precipitate re-suspended in water. A number of different buffer conditions for elution of selected RNA from the filters can be used. For example, without limitation non-detergent aqueous protein denaturing agents such as quanidinium chloride, quanidinium thiocyanate, etc., as are known in the art, can be used. The specific solution used for elution of nucleic acids from the filter can be routinely selected by one of ordinary skill in the art.

As is understood in the art, the concentration of various ions, in particular, the ionic strength, and the pH value impact on the value of the dissociation constant of the target/ligand complex. Thus, the terms "lower stringency" and "higher stringency" pertain to such buffer conditions (e.g. binding buffer conditions) as salt concentration, ionic strength generally, pH, temperature, or organic solvents, as will be readily appreciated by those skilled in the art after review of the disclosure presented herein.

The method can further comprise step (i): repeating steps (e), (f) and (g) (preferred embodiment) or repeating steps (f), (g) and (h) (alternative embodiment) in a higher stringency buffer. Optionally, the higher stringency buffer comprises a physiological buffer. As used herein, "physiological conditions" means the salt concentration and ionic strength in an aqueous solution that characterize fluids found in human metabolism commonly referred to as physiological buffer or physiological saline. In general, these are represented by an intracellular pH of 7.1 and salt concentrations (in mM) of $Na^+$: 3-15; $K^+$: 140; $Mg^{+2}$: 6.3; $Ca^{+2}$:10-14; $Cl^-$:3-15, and an extracellular pH of 7.4 and salt concentrations (in mM) of $Na^+$:145; $K^+$:3; $Mg^{+2}$: 1-2; $Ca^{+2}$: 1-2; and $Cl^-$: 110. The use of physiological conditions in the ligand selection method is important, particularly with respect to those ligands that can be intended for therapeutic use.

V.A. Modified SELEX

Systematic Evolution of Ligands by EXnonential Enrichment, SELEX, is essentially a powerful iterative affinity purification process that can be employed to isolate rare ligands from nucleic-acid combinatorial libraries. As such, it is necessary to establish conditions under which the desired activity (e.g., binding a coagulation factor, angiogenesis factor or E2F) can be detected in the initial randomized library prior to initiating the SELEX process. In addition, to purify ligands possessing this activity from other sequences within the randomized pool, the signal of the desired activity must be above the "noise" of library binding to the partitioning scheme (i.e., the fraction of sequences binding to the partitioning media due to target protein binding must be greater than those binding in a target independent manner).

Generally, the SELEX process can be defined by the following series of steps:

(1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below; (b) to facilitate mimicry of a sequence known to bind to the target; or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

(2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

(3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5-50%) are retained during partitioning.

(4) Those nucleic acids selected during partitioning as having the relatively higher affinity to the target are then amplified to create a new candidate mixture that is enriched in nucleic acids having a relatively higher affinity for the target.

(5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The desired characteristics for a given nucleic acid ligand can vary. All nucleic acid ligands are capable of forming a complex with the target. In some cases, it is desired that the nucleic acid ligand will serve to inhibit one or more of the biological activities of the target. In other cases, it is desired that the nucleic acid ligand serves to modify one or more of the biological activities of the target. In other cases, the nucleic acid ligand serves to identify the presence of the target, and its effect on the biological activity of the target is irrelevant.

In order to identify conditions that are preferred for the initiation of the SELEX process (i.e., signal to noise ratio >2) a matrix strategy to test for target dependent versus target independent binding of the library under different conditions is provided in accordance with the present invention. While this strategy is employed to identify SELEX conditions that are physiologic or that approach physiologic for the target protein, it could readily be applied to identify very non-physiologic conditions if one desired to use an aptamer in downstream processes that require solvents that are non-physiologic.

In one embodiment of the matrix, the monovalent salt concentration and pH of the binding buffer are varied in combination to test monovalent salt concentrations from 10 (low stringency) to 150 mM (high stringency) and a pH range from 7.0-8.0 in binding reactions with radiolabeled randomized library RNA and varying concentrations of target protein. All binding buffers also contain physiologic concentrations of the appropriate divalent metal ions (depends on the in vivo compartment of the target) and excipient as needed to maintain the protein in solution in a native state. This systematic variation of these critical parameters allows for the rapid identification of the buffer conditions and target concentration under which the SELEX process can be successfully initiated. In some cases, the initial conditions are non-physiologic with respect to the monovalent salt concentration, the pH, or both. In these cases, the matrix strategy can be employed again in subsequent rounds of the SELEX process to determine when the conditions (i.e. binding buffer) of the SELEX can be changed. This strategy is repeated every few rounds until the SELEX process can be continued under physiologic conditions.

V.B. Toggle Method

Another embodiment of a method of identifying a ligand to a target from a candidate mixture of potential ligands is provided in accordance with the present invention. Products, i.e., ligands, produced or identified via the method are also provided in accordance with the present invention.

The method preferably comprises: (a) providing a target selected from a first species of organism; (b) preparing a candidate mixture of potential ligands; (c) contacting the candidate mixture with the target, wherein ligands having increased affinity to the target from the first species of organism relative to the candidate mixture bind to the immobilized target from the first species of organism; (d) removing unbound candidate mixture; (e) collecting the ligands that are bound to the target from the first species of organism to produce a first collected ligand mixture for the target; (f) contacting the first collected ligand mixture with a target from a second species of organism, the target from the second species having at least a portion thereof that is substantially homologous to the same portion in the target from the first species, wherein ligands having increased affinity to the target from the second species relative to the first collected ligand mixture bind to the target; (g) removing unbound first collected ligand mixture; and (h) collecting the ligands that are bound to the target from the second species of organism to form a second collected ligand mixture thereby identify ligands to the target.

Preferably, ligands in the first or second collected ligand mixture are enriched or expanded by any suitable technique, e.g. amplification, prior to contacting the first collected ligand mixture with the target from the second species of organism, after collecting the ligands that bound the target from the second species of organism, or both. Optionally, the contacting and expanding or enriching steps are repeated as necessary to produce a desired ligand. Thus, it is possible that the second collected ligand mixture can comprise a single ligand.

Another embodiment of a method of identifying a ligand to a target from a candidate mixture of potential ligands in accordance with the present invention comprises: (a) immobilizing a target on a substrate, the target comprising a target selected from a first species of organism; (b) preparing a candidate mixture of potential ligands; (c) passing the candidate mixture over the substrate, wherein ligands having increased affinity to the immobilized target from the first species of organism relative to the candidate mixture bind to the immobilized target from the first species of organism; (d) passing a wash buffer over the substrate to remove unbound candidate mixtures; (e) passing an eluting buffer over the substrate to elute the ligands that are bound to the immobilized target from the first species of organism to produce an eluted ligand mixture; (f) passing the eluted ligand mixture over a substrate comprising an immobilized target from a second species of organism, the target from the second animal species contacting the first collected ligand mixture, the target from the second species having at least a portion thereof that is substantially homologous to the same portion in the target from the first species, wherein ligands having increased affinity to the target from the second species relative to the first collected ligand mixture bind to the immobilized target; (g) passing a wash buffer over the substrate to remove unbound eluted ligand mixture; and (h) passing an eluting buffer over the substrate to elute the ligands that are bound to the immobilized target from the second species of organism to thereby identify ligands to the target.

Preferably, ligands in the first or second collected ligand mixture are enriched or expanded by any suitable technique, e.g. amplification, prior to contacting the first collected ligand mixture with the target from the second species of organism, after collecting the ligands that bound the target from the second species of organism, or both. Optionally, the contacting and expanding or enriching steps are repeated as necessary to produce a desired ligand. Thus, it is possible that the second collected ligand mixture can comprise a single ligand.

Optionally, the method can further comprise further comprising step (i): repeating steps (f), (g) and (h) one or more times, wherein each additional time alternates between the target from the first species and the target from the second species. The method can also further comprise amplifying the eluted ligand to yield a ligand-enriched mixture, whereby a ligand to the target is identified.

The method is applicable to any target and to any ligand as defined herein for which a ligand is sought. Representative targets are also disclosed in U.S. Pat. No. 5,756,291, herein incorporated by reference. Alternation of the target between homologous proteins of different species ensures that the products of selection will bind to both proteins, most likely to domains conserved between the two proteins. Because conserved domains tend to be functionally important, driving the selection with homologous proteins can be advantageous even when species cross-reactivity is not necessarily sought. Similarly, the toggle approach is generalizable to homologous proteins of different viral strains and to related proteins of the same species (such as receptor or ligand families with redundant or overlapping function), where cross-reactivity can improve in vivo efficacy. Thus, the phrase "the target from the second species having at least a portion thereof that is substantially homologous to the same portion in the target from the first species" includes but is not limited to conserved domains.

The term "substantially homologous" in the context of two or more polypeptide sequences is measured by polypeptide sequences having about 35%, or 45%, or preferably from 45-55%, or more preferably 55-65%, or most preferably 65% or greater amino acids which are identical or functionally equivalent. Percent "identity" and methods for determining identity are defined herein below. Further, this term also encompasses proteins typically referred to in the art as homologues, e.g. porcine and human thrombin as disclosed in the Examples.

Optimal alignment of sequences for comparison can be conducted, e.g., by the local homology algorithm of Smith and Waterman (1981) *Adv Appl Math* 2:482, by the homology alignment algorithm of Needleman and Wunsch (1970) *J Mol Biol* 48:443, by the search for similarity method of Pearson and Lipman (1988) *Proc Nati Acad Sci USA* 85:2444, by computerized implementations of these algorithms (GAP, BESTFIT, FASTA, and TFASTA in the Wisconsin Genetics Software Package, Genetics Computer Group, Madison, Wis.), or by visual inspection (See generally, Ausubel et al. (1992)).

A preferred algorithm for determining percent sequence identity and sequence similarity is the BLAST algorithm, which is described in Altschul et al. (1990) *J Mol Biol* 215: 403-410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff and Henikoff (1989) *Proc Natl Acad Sci USA* 89:10915.

In addition to calculating percent sequence identity, the BLAST algorithm also performs a statistical analysis of the similarity between two sequences. See, e.g., Karlin and Altschul (1993) *Proc Nati Acad Sci USA* 90:5873-5887. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

In a preferred embodiment, the method further comprises amplifying the eluted ligand to yield a ligand-enriched mixture, whereby a ligand to the target is identified. The ligand mixture can comprise a candidate mixture of nucleic acids. In this case, the candidate mixture of nucleic acids can comprise single strand nucleic acids. The single stranded nucleic acids can comprise deoxyribonucleic acids.

Preferably, the single stranded nucleic acids are ribonucleic acids. In this case amplification can be accomplished, for example, via reverse transcriptase PCR reactions, as disclosed in U.S. Pat. No. 5,817,785, herein incorporated by reference. Even more preferably, the candidate mixture of nucleic acids comprises 2'-modified ribonucleic acids. Even more preferably, the 2'-modified ribonucleic acids comprise 2'-fluoro (2'-F) modified nucleic acids.

Contemplated species of organism include plants, animals, bacteria, fungi, viruses or other organism. Preferred species of animals include warm-blooded vertebrates, including but not limited to humans, rats, mice, pigs, apes, monkeys, cats, dogs, cattle, oxen, sheep, goats and horses, or other mammal typically used in experiments. Additional species include domesticated fowl, i.e., poultry, such as turkeys, chickens, ducks, geese, guinea fowl, and the like, as they are also of economical importance to humans. Thus, the term "avian" as used herein refers to any avian species, including but not limited to *Gallinacea* sp., chicken, turkey, duck, goose, quail and pheasant. Chicken is currently preferred.

Fish represent a category of animals of interest for agricultural and ecological reasons. Representative fish species include, but are not limited to, trout, salmon, carp, shark, ray, flounder, sole, tilapia, medaka, goldfish, guppy, molly, platyfish, swordtail, zebrafish, loach, catfish, and the like. Representative general techniques that are applicable to fish have been described by Ozato et al, *Cell Differ,* 19:237-244 (1986), Inoue et al, *Cell Differ. Dev.,* 29:123-128 (1990), Rokkones et al, *J. Comp. Physiol*. B, 158:751-758 (1989), and Guyomard et al, *Biochimie,* 71:857-863 (1989), describing preparation of transgenic medaka, medaka, salmon and trout, respectively.

LABORATORY EXAMPLES

The following Laboratory Examples have been included to illustrate preferred modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following examples are intended to be exemplary only and that numerous changes, modifications and alterations can be employed without departing from the spirit and scope of the invention.

Example 1

Initial Condition Matrix to Coagulation Factor VIIa

Figure 8:
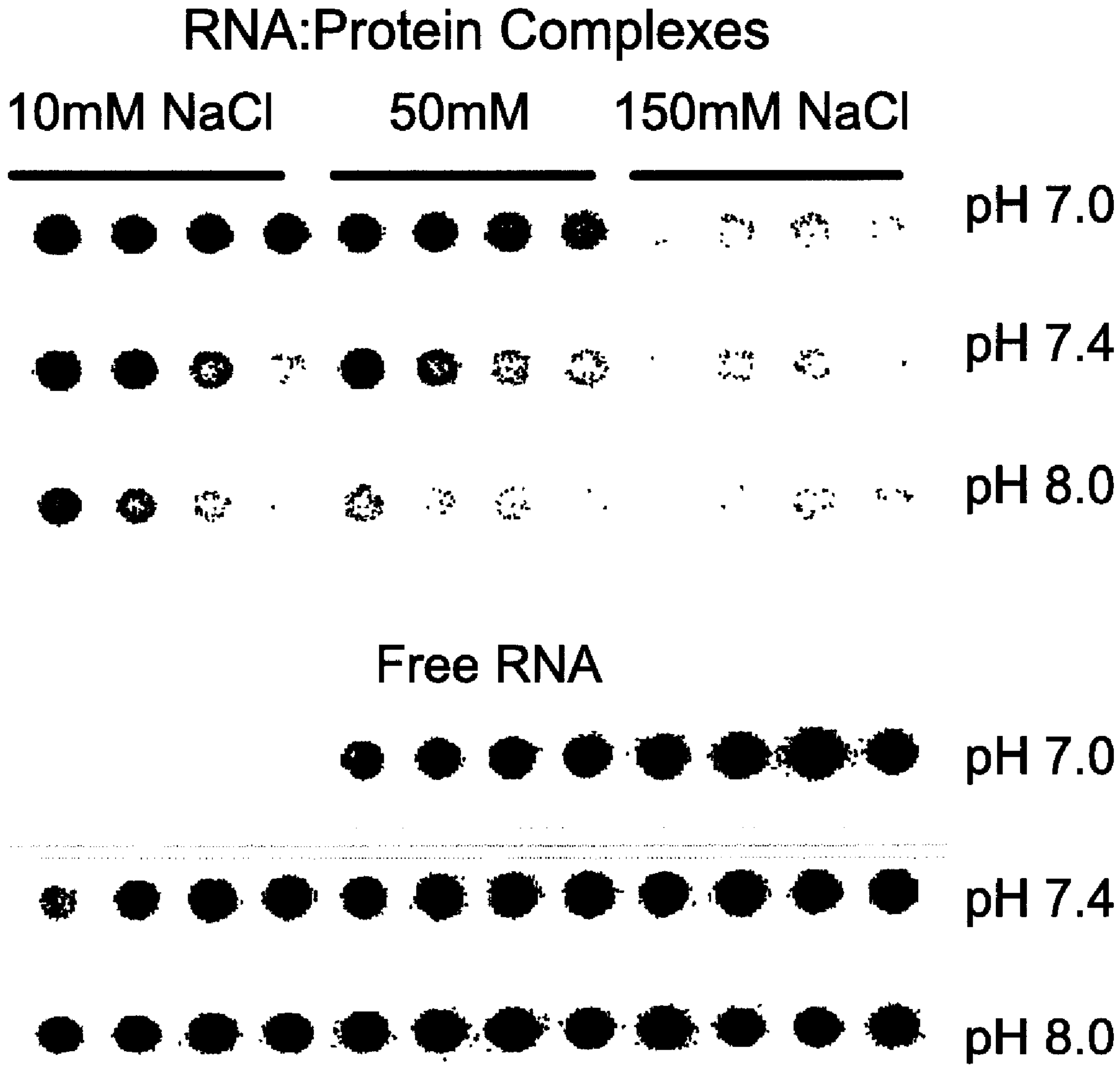
FIG. 8 is a PHOSPHORIMAGER® (Molecular Dynamics of Sunnyvale, Calif.) scan depicting initial condition matrix to coagulation factor VIIa. Radiolabeled 2'fluoropyrimidine-modified library RNA was incubated with varying concentrations of coagulation factor VIIa in 9 different buffers, and target-bound versus free RNA was determined using the double-filter nitrocellulose filter binding assay (Wong and Lohman, 1993, *Proc. Natl. Acad. Sci. USA* 90, 5428-5432).

Referring now to FIG. 8, radiolabeled 2'fluoropyrimidine-modified library RNA was incubated with varying concentrations of coagulation factor VIIa in 9 different buffers, and target-bound versus free RNA was determined using the double-filter nitrocellulose filter binding assay (Wong and Lohman, 1993, *Proc. Natl. Acad. Sci. USA* 90, 5428-5432). For all conditions, the binding buffers contain 20 mM Hepes at the pH shown, 2 mM $CaCl_2$, and NaCl at the concentration shown. From the left to right in each set of 4, the factor VIIa concentration is 5 μM, 1.67 μM, 0.56 μM and no target. The fraction of the pool that binds factor VIIa decreases dramatically as the monovalent salt increases, but is relatively unaffected by the change of pH at a given NaCl concentration. In addition, the fraction of RNA bound in the absence of target is much greater at lower NaCl concentrations and lower pH.

In this Example, there is essentially no target binding above background under physiologic conditions (pH 7.4, 150 mM NaCl). Thus, if the SELEX process were initiated under these conditions it would fail outright. Likewise, at pH 7.0, 50 mM NaCl, there is significant target dependent binding, but also significant target independent binding. Were the SELEX initiated under these conditions, it would also likely fail. Preferred initiating conditions are pH 7.4, 50 mM NaCl, with a relatively high (μM) concentration of factor VIIa.

Example 2

Initial Condition Matrix to Coagulation Factor IXa

Figure 9:
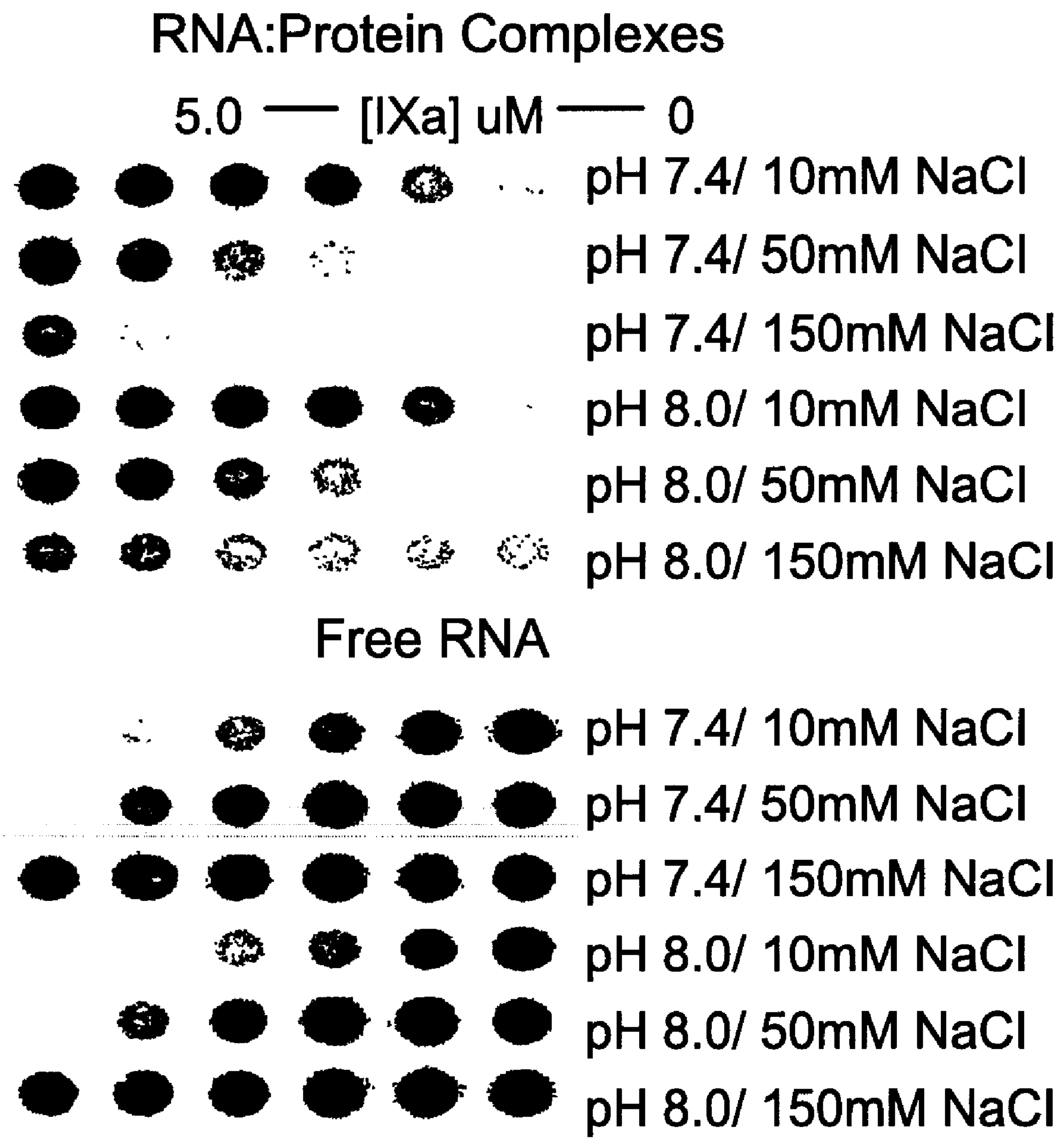
FIG. 9 is a PHOSPHORIMAGER® (Molecular Dynamics of Sunnyvale, Calif.) scan of an initial condition matrix to coagulation factor IXa. Radiolabeled 2'fluoropyrimidine-modified library RNA was incubated with varying concentrations of coagulation factor IXa in 6 different buffers, and target-bound versus free RNA was determined using the double-filter nitrocellulose filter binding assay.

Referring now to FIG. 9, radiolabeled 2'fluoropyrimidine-modified library RNA was incubated with varying concentrations of coagulation factor IXa in 6 different buffers, and target-bound versus free RNA was determined using the double-filter nitrocellulose filter binding assay. For all conditions, the binding buffers contain 20 mM Hepes at the pH shown, 2 mM $CaCl_2$, and NaCl at the concentration shown. From left to right in sets of 6, the FIXa concentration decreases 2 fold at each point from 5 μM to 0.31 μM, and the sixth point is the no target control.

The fraction of the pool that binds factor IXa decreases dramatically as the NaCl concentration increases. In this Example, there is low but detectable binding of the pool to factor IXa under physiologic conditions, and the SELEX process could be successfully initiated under these conditions. However, a preferred initiating condition would be pH 7.4, 50 mM NaCl, followed by a change to physiologic buffer in the early rounds of the SELEX process.

Example 3

Toggle SELEX

Species cross-reactivity facilitates the pre-clinical evaluation of potentially therapeutic molecules in animal models. This Example describes an in vitro selection strategy in which RNA ligands (aptamers) that bind both human and porcine thrombin were selected by "toggling" the protein target between human and porcine thrombin during alternating rounds of selection. The "toggle" selection process yielded a family of aptamers, all of which bound both human and porcine thrombin with high affinity. TOGGLE-25, a characteristic member, inhibited two of thrombin's most important functions: plasma clot formation and platelet activation. If appropriate targets are available, the toggle strategy is a simple measure that promotes cross-reactivity and can be generalizable to related proteins of the same species as well as to other combinatorial library screening strategies. This strategy should facilitate the isolation of ligands with needed properties for gene therapy and other therapeutic and diagnostic applications.

Figure 31:
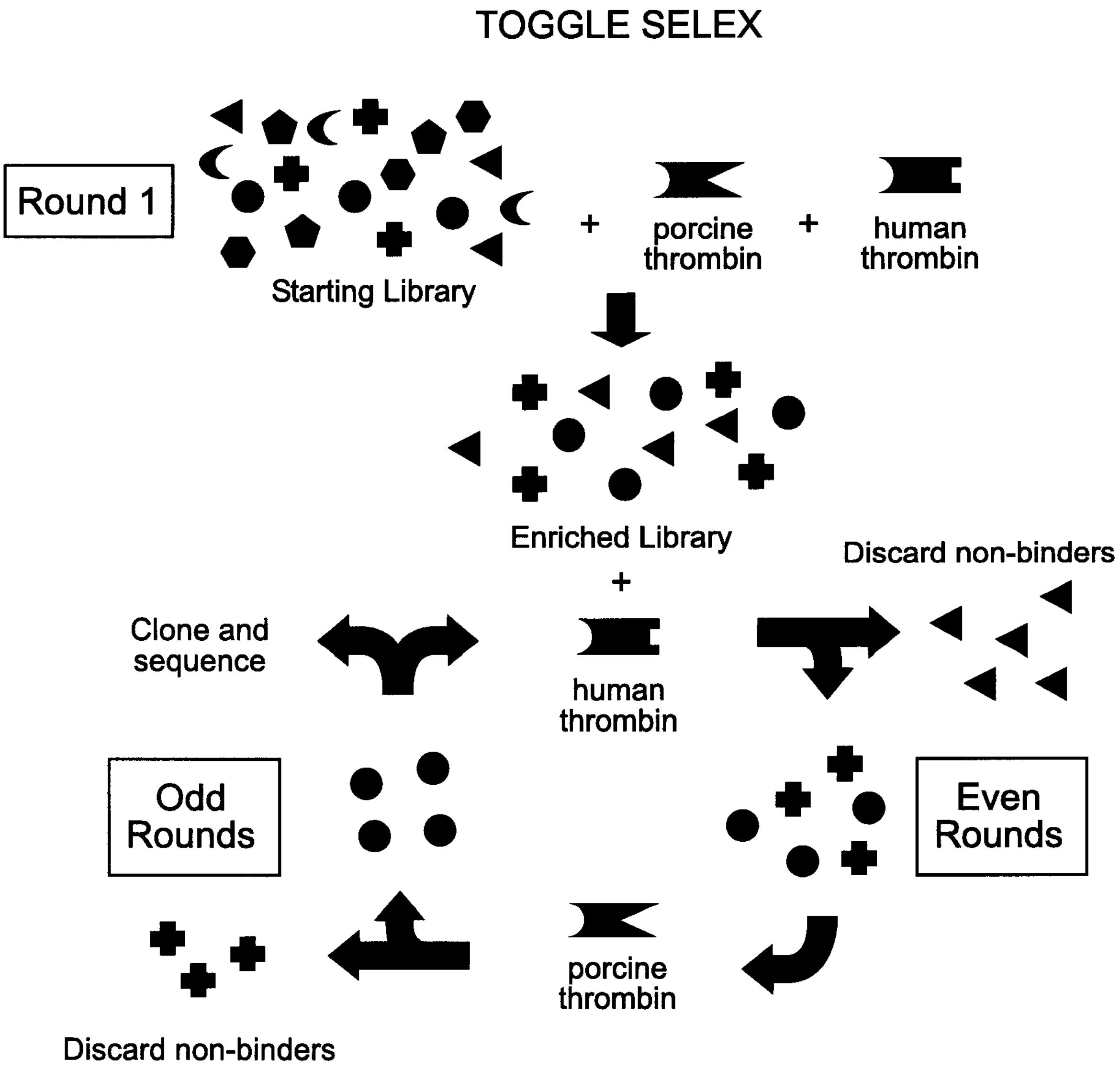
FIG. 31 is a schematic depicting the Toggle SELEX method of the present invention. Aptamers that bind both human and porcine thrombin were selected by "toggling" the protein target between human and porcine thrombin during alternating rounds of selection.

Anti-thrombin therapeutics have been of great interest due to thrombin's central role in blood coagulation as well as to its suggested role in cellular proliferation (intimal hyperplasia) following vascular injury. To develop a method for the generation of aptamers that would be clinically useful in humans and testable in animal models, a novel selection strategy was applied to this previously validated target. Nuclease-resistant RNA ligands that bind both human and porcine thrombin were selected by "toggling" the protein target between human and porcine thrombin during alternating rounds of selection (FIG. 31). Such cross-reactive aptamers inhibit both porcine and human thrombin activity as might be expected from ligands made to bind evolutionally conserved regions of a protein.

A library containing approximately $10^{14}$ different RNAs was screened for those molecules that bind both human and porcine thrombin. In the first round of in vitro selection, the starting library was incubated with both human and porcine thrombin (F2). RNAs that bound either protein were recovered and amplified to generate a library enriched in F2-binding RNAs. In round 2 of selection, the enriched library of RNAs was incubated with human F2 alone, and bound RNAs were recovered and amplified to generate a library of RNAs that had been further enriched for members that bound surfaces on human F2 (FIG. 31). In round 3, this human-focused library was incubated with porcine F2, and the subset of RNAs that bound the porcine protein were recovered and amplified to generate a library that had been further enriched for binding structural motifs that were conserved between the F2 homologs. This "toggle" selection process was repeated during rounds 4-13 of SELEX utilizing the human protein for even rounds and the porcine protein for odd rounds. In parallel, thirteen (13) rounds of standard SELEX were performed against the individual human and porcine proteins. To determine if toggle SELEX enriched for aptamers that cross-reacted with both human and porcine F2, binding properties of the RNA pools from various rounds of selection were evaluated.

Figure 32:
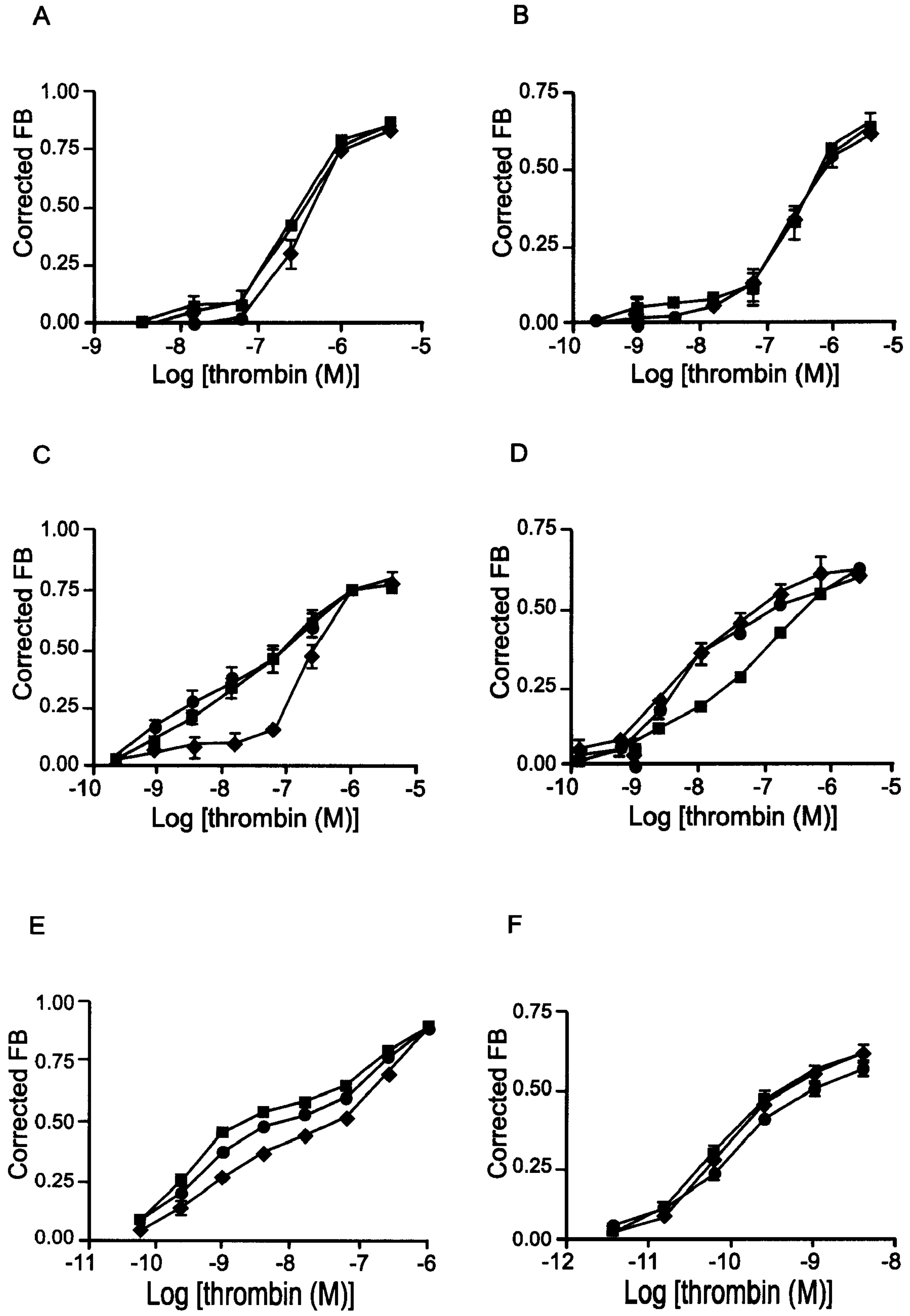
FIGS. 32A-32F depict RNA pool binding. The fraction of RNA bound, corrected for nonspecific binding to nitrocellulose (Corrected FB), is plotted as a function of thrombin concentration. The binding affinities of RNA pools from the toggle selection (●, circle), human thrombin selection (■, square), and porcine thrombin selection (♦, diamond) for human thrombin protein (FIGS. 32A, 32C, 32E) and porcine thrombin protein (FIGS. 32B, 32D, 32F) were compared after round 3 (FIGS. 32A, 32B), round 11 (FIGS. 32C, 32D), and round 13 (FIGS. 32E, 32F).

Early in the selection (round 3), no significant differences in the binding affinities of RNA pools from the human, toggle, or porcine selections were observed for either human F2 (FIG. 32A) or porcine F2 (FIG. 32B). By round 11, however, RNA pools selected against human F2 alone had less avid binding for porcine F2 (FIG. 32C), and RNA pools selected against porcine F2 alone had less avid binding for human F2 (FIG. 32D), suggesting the presence of species-specific ligands within these pools; whereas RNA pools generated via toggle SELEX bound both human and porcine F2 as well as did RNA pools generated against each protein alone (FIGS. 32C and 32D). With continued selection, the differential binding of porcine selection RNA pools for human F2 was diminished (FIG. 32E), and the differential binding of the human selection RNA pools for porcine F2 was lost (FIG. 32F), indicating the loss of species-specific ligands from these pools.

Three in vitro selections were performed in parallel: human thrombin, porcine thrombin, and a toggle selection using alternating rounds of human and porcine thrombin in a SELEX process as disclosed in Examples 1 and 2 above. After thirteen rounds of the SELEX process, the pools were cloned and sequenced. The random sequences of seven clones of high affinity for one another are shown in FIG. 11. Some of the sequences shown in FIG. 11 were represented in more than one selection but are only listed once in FIG. 11 for clarity.

Thus, the amplification products from round 13 of each selection were cloned and sequenced. Thirteen clones analyzed from the human selection had identical sequences (HUMAN-1). Consistent with round 13 binding data (FIGS. 32E and 32F), HUMAN-1 RNA bound both human and porcine F2 with high affinity. Thus, the selection to human F2 appears to have been driven to completion and yielded an aptamer that binds an epitope present on both the human and porcine proteins. Sequences from earlier rounds, when multiple aptamers were still present, were not analyzed. All sequences from the toggle selection and 10 of 14 sequences from the porcine selection shared a conserved motif with the predominant human selection sequence: ACAAAGCUGRAGWACUUA (SEQ ID NO:227), where R represents A or G and W represents A or U. RNAs possessing the consensus sequence shared similarly high binding affinities for both human F2 ($K_d$'s ranging from 1 to 4 nM) and porcine F2 (all $K_d$'s<1 nM). A representative RNA, TOGGLE-25, bound human F2 with a $K_d$ of 2.8±0.7 nM and bound porcine F2 with a $K_d$ of 83±3 pM. A unique RNA from the porcine selection (PIG-10) bound porcine F2 with a $K_d$ of 50±8 pM but bound human F2 with a $K_d$ of greater than 600 nM, demonstrating greater than 10,000-fold specificity for porcine F2 over human F2. Thus, the porcine thrombin selection yielded two classes of high affinity ligands. One recognizes an epitope that is conserved on human F2 while the other recognizes an epitope that is not conserved. Interestingly, the two RNAs compete for binding to porcine F2, suggesting that they bind overlapping regions of the protein. These two RNAs are further characterized below.

A fundamental problem in the development of new therapies is that potentially useful therapeutic agents might not progress from bench top to clinical trials due to lack of demonstrated efficacy in animal models. Drug discovery strategies generally employ human targets, and the inability to cross-react with homologous targets of other species can interfere with pre-clinical testing. This Example discloses a high-affinity inhibitor of the protease thrombin using a novel in vitro selection strategy. The "toggle" selection strategy exploits the malleability of iterative in vitro techniques and is generalizable to other combinatorial library screening strategies. Alternation of the target between homologous proteins of different species ensures that the products of selection will bind to both proteins, most likely to domains conserved between the two proteins. Because conserved domains tend to be functionally important, driving the selection with homologous proteins can be advantageous even when species cross-reactivity is not necessarily sought. Similarly, the toggle approach is generalizable to homologous proteins of different viral strains and to related proteins of the same species (such as receptor or ligand families with redundant or overlapping function), where cross-reactivity can improve in vivo efficacy.

For a relatively well-conserved protein like thrombin (85% amino acid homology between human and bovine thrombin (Butkowski, R. J., et al. (1977) *J. Biol. Chem.* 252:4942-4957), aptamers selected against human thrombin might cross-react with thrombin of other species. A single-stranded DNA aptamer to human thrombin inhibits thrombin function in canine and ovine models, although relative binding affinities have not been reported. DeAnda, A., Jr., et al. (1994) *Ann. Thorac. Surg.* 58:344-350; Griffin, L. C., et al. (1993) *Blood* 81:3271-3276. The single aptamer identified from round 13 of the selection against human thrombin happened to cross-react with porcine thrombin; however, aptamers from earlier rounds where species-specificity was observed were not analyzed, and these RNA pools likely included species-specific aptamers. The identification of a species-specific aptamer from the porcine selection underscores the point that—even for selection against a well-conserved protein—species cross-reactivity should not be assumed.

The "toggle" selection yielded a family of aptamers, all of which bound both human and porcine thrombin with high affinity. Although selection against both targets could theoretically sacrifice affinity for the human target, this "toggle" family demonstrated affinity for human thrombin similar to RNAs generated against human thrombin alone. Furthermore, the potential loss in binding affinity should be outweighed by the potential gain in activity expected from driving selection toward evolutionally conserved regions of the protein. TOGGLE-25, a characteristic member of the "toggle" family, inhibited two of thrombin's most important functions: plasma clot formation and platelet activation. Truncation of the full-length aptamer to approximately 40 nt or fewer is preferred for efficient chemical synthesis, but minimization can have varying effects on binding and inhibitory activity. A 25-nt truncate (TOGGLE-25t) retained the inhibitory activities of the full-length aptamer and demonstrated greater potency, particularly in plasma-based assays. The superiority of the TOGGLE-25t truncate in these assays might be attributable to slightly higher affinity for thrombin as well as theoretically less nonspecific binding to positively-charged plasma proteins.

Thrombin aptamers can fulfill a clinical need for more and better anticoagulants and antithrombotics. Widely utilized agents such as heparin and platelet surface receptor antagonists are effective but are limited by bleeding complications due to Heparin Induced Thrombocytopenia and irreversibility, respectively. The plasma stability of our aptamer has been increased by the substitution of endonuclease-resistant nucleotides, which typically confer an in vitro half-life of greater than 5 hours as compared to 30 to 60 minutes for DNA and seconds for unmodified RNA. Pieken, W. A., et al. (1991). *Science* 253:314-317; Beigelman, L., et al. (1995) *J. Biol. Chem.* 270:25702-25708. Due to its small size and stability in plasma, its in vivo half-life is governed by the rate of renal clearance, which can be reduced by the addition of various inert high molecular weight or hydrophobic groups Willis, M. C., et al. (1998) (published erratum appears in *Bioconjug Chem* September-October 1998; 9(5):633) *Bioconjug Chem.* 9:573-582; Tucker, C. E., et al. (1999). *Journal of Chromatography. B, Biomedical Sciences & Applications* 732:203-212. Depending on the planned application, therefore, our aptamer can be modified to have an in vivo half-life of minutes or hours. In addition, the high affinity of the aptamer can be exploited to more effectively block the thrombogenic and mitogenic effects of thrombin on platelets, fibroblasts, endothelium, and smooth muscle, which are believed to be mediated by proteolytic activation of a novel family of receptors, Protease-Activated Receptors or PARs.

Aptamers are a promising class of molecules, for target validation as well as for diagnosis and therapy. Nuclease-resistant aptamers have already proven to be useful reagents for the study of extracellular targets in a variety of disease processes, and animal studies have paved the way for the first clinical trials of an aptamer against VEGF in the wet form of age-related macular degeneration. In addition, gene therapeutic methods utilizing viral constructs have been used to "express" unmodified RNA aptamers against intracellular targets. Sullenger, B. A., et al. (1990) *Cell* 63:601-608; Good, P. D., et al. (1997) *Gene Ther.* 4:45-54. Species cross-reactivity will greatly facilitate the transition of these molecules from in vitro assays to animal models to human subjects. If the appropriate targets are available, the toggle strategy is a simple measure that promotes cross-reactivity. Because the selection process is performed in vitro, possible schemes to manipulate the specificity of an aptamer for the targeted protein(s) are virtually unlimited.

Accordingly, the present invention provides a method to isolate the therapeutic compounds against human (or other species) molecular targets such that the therapeutic compound cross-reacts with homologous molecular targets from another species. For example, this process can entail the selection of a therapeutic compound against a human target molecule of interest followed by selection against a homologous molecule from another species. This process yields compounds that can be evaluated in a predetermined preclinical animal model by isolating molecules that cross-react with the species that is of interest.

As disclosed in this Example, an aptamer to human thrombin that cross reacts with human porcine thrombin has been produced using this method. Moreover, this toggle selection approach is expected to yield compounds that interact with functionally conserved regions of the target molecule that are likely to be the functionally important regions on the target.

Example 4

Inhibition of the Activity of Coagulation Factor IXa

Referring now to FIG. 2A, it was shown that RNA 9.3 (SEQ ID NO:3) inhibits the FIXa/FVIIIa catalyzed activation of FX. In FIG. 2A, factor IXa (0.5 nM) was equilibrated with no RNA (▲), 10 nM control RNA (■), or 10 nM RNA 9.3 (●). The FX activation reaction was initiated by the addition of FVIIIa (1 nM), PC/PS vesicles (100 μM) and FX (200 nM). The amount of FXa formed over time at 37° C. was measured.

Figure 2B:
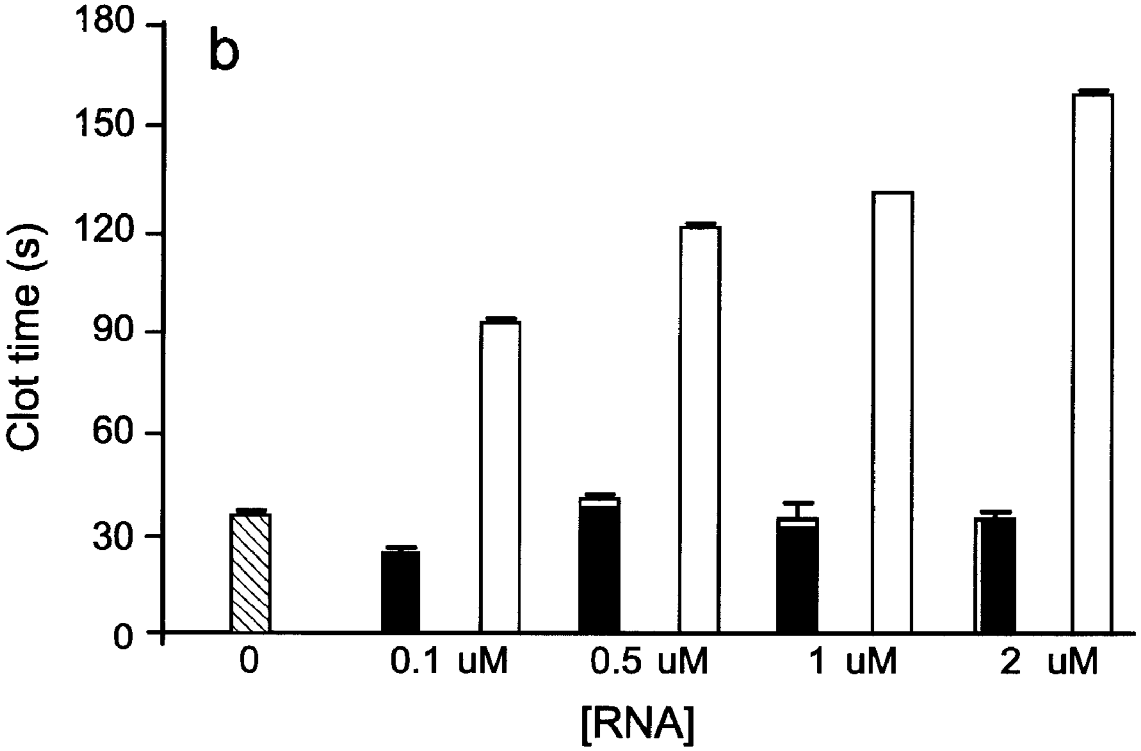
FIG. 2B is a bar graph showing that RNA 9.3 (SEQ ID NO:3) prolongs the clotting time of human plasma, thereby demonstrating RNA 9.3 (SEQ ID NO:3) inhibits the activity of coagulation factor IXa. The clotting time of normal human plasma was measured in an aPTT assay in the absence of RNA (striped bar), or in the presence of increasing concentrations of control RNA (solid bar) or RNA 9.3 (SEQ ID NO:3) (open bar). The clotting time is expressed as the mean±sem for duplicate measurements.

Referring now to FIG. 2B, it was shown that RNA 9.3 (SEQ ID NO:3) prolongs the clotting time of human plasma. The clotting time of normal human plasma was measured in an aPTT assay in the absence of RNA (striped bar), or in the presence of increasing concentrations of control RNA (solid bar) or RNA 9.3 (SEQ ID NO:3) (open bar). The clotting time is expressed as the mean±sem for duplicate measurements.

Example 5

Truncated FIXa Aptamers

The primary sequence of the minimal FIXa aptamers $9.3^t$ and $9.20^t$ are set forth in Table 1 above. The apparent $K_d$ for binding of the 9.3 truncate $9.3^t$ to FIXa ranges from about 1 to about 3 nM, and to FIX ranges from about six (6) to about ten (10) nM. The apparent $K_d$ of the $9.20^t$ truncate $9.20^t$ for FIXa is ~100-200 nM.

Figure 3A:
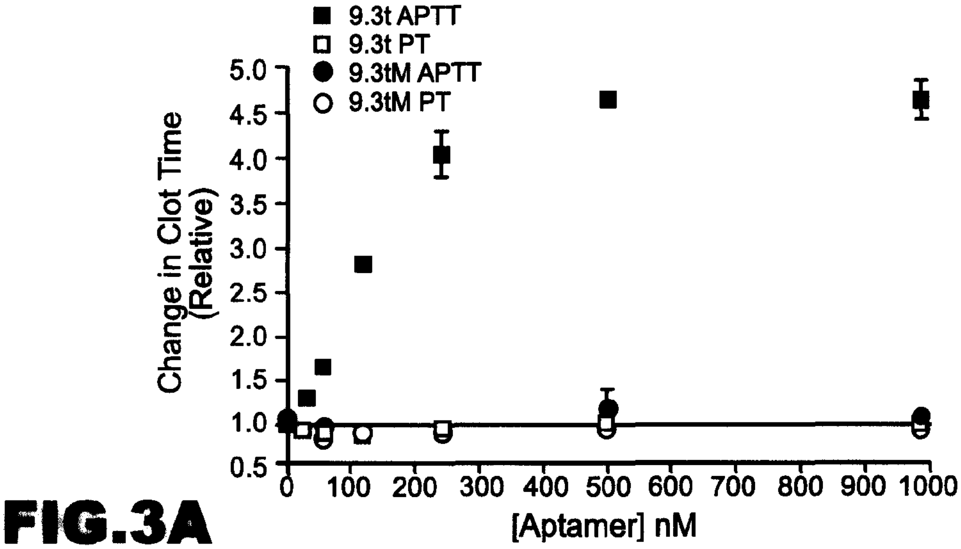
FIGS. 3A-3C show that aptamer 9.3t (SEQ ID NO:70) inhibits FIXa activity in pigs.
Figure 3B:
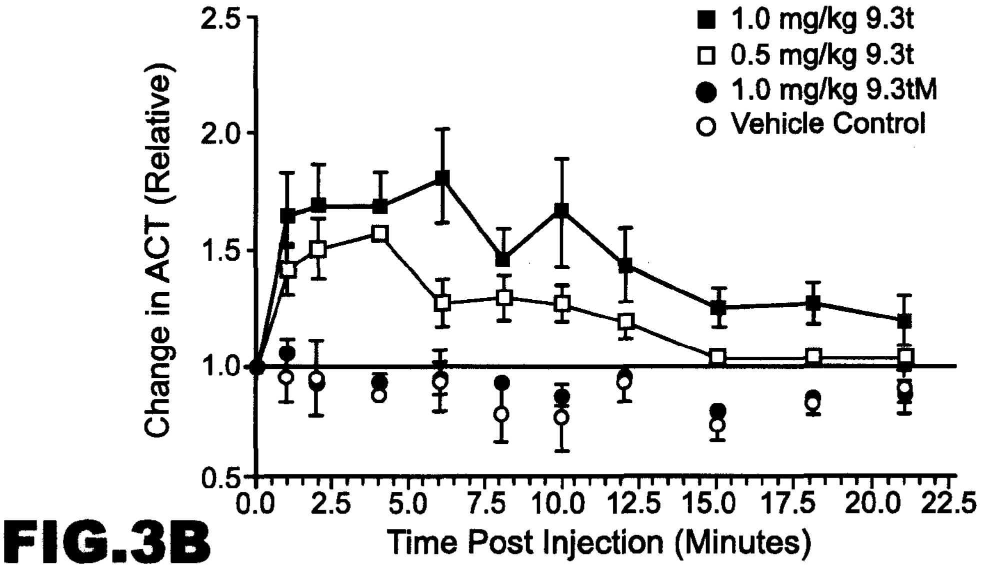
Figure 3C:
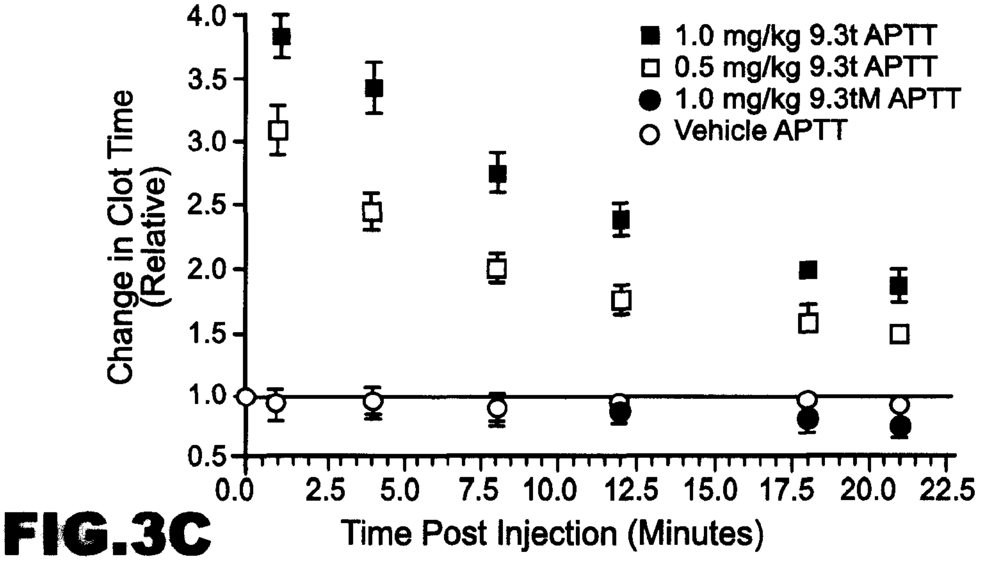
Figure 4A:
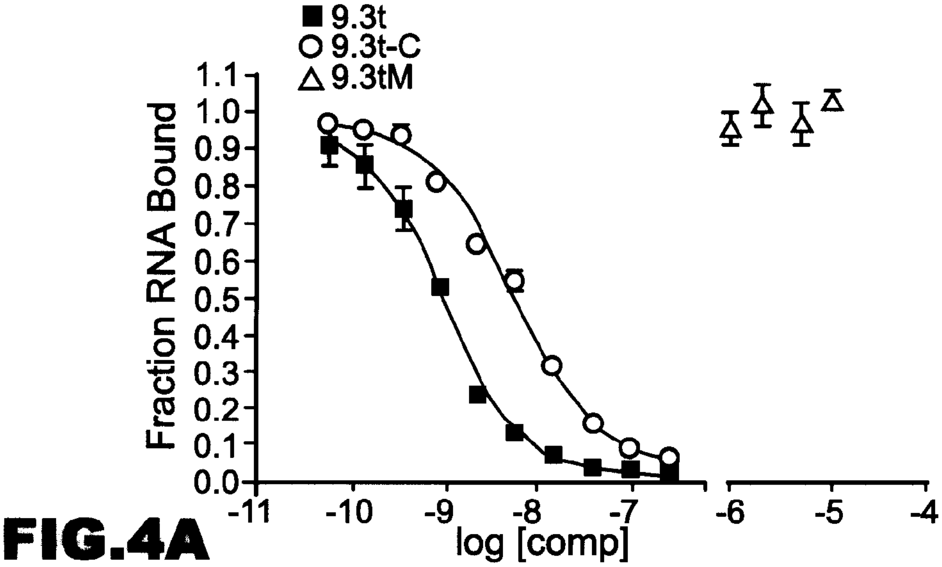
FIG. 4A is a line graph showing in vitro inhibitory activity of cholesterol modified aptamer $9.3^t$ (SEQ ID NO:70—cholesterol modified form referred to herein as $9.3^{t-C}$). Cholesterol addition has modest effect on the affinity of aptamer $9.3^{t-C}$ for FIXa based upon a competition binding assay to measure affinity of $9.3^{t-C}$ for FIXa. Competitors: ■, $9.3^{t,}$; O, $9.3^{t-C}$; Δ, $93^{tM}$.
Figure 4B:
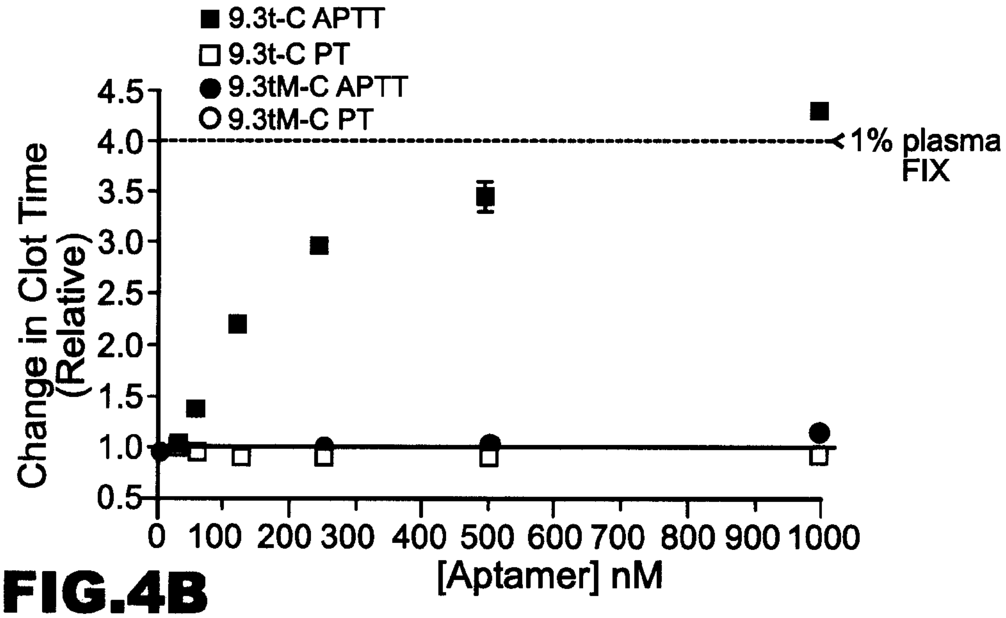
FIG. 4B is a plot depicting in vitro anticoagulant activity of aptamer $9.3^{t-C}$ in human plasma. ■, $9.3^{t-C}$ APTT; □, $9.3^{t-C}$ PT; ●, $9.3^{tM-C}$ APTT; O, $9.3^{tM-C}$ PT.
Figure 4C:
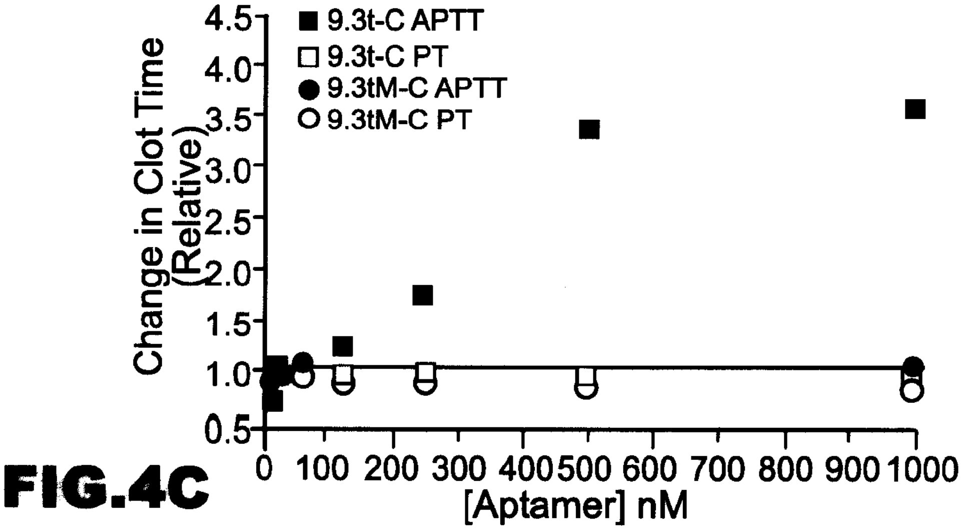
FIG. 4C is a plot depicting in vitro anticoagulant activity aptamer $9.3^{t-C}$ in pig plasma. ■, $9.3^{t-C}$ APTT; □, $9.3^{t-C}$ PT; ●, $9.3^{tM-C}$ APTT; O, $9.3^{tM-C}$ PT.

Referring now to FIGS. 3A-3C, $9.3^t$ prolongs the clotting time of pig plasma as well as clotting time in vivo in a dose dependent manner as determined by aPTT clotting assays, ACT assays, and PT assays. The dose response curve is consistent with substantially complete inactivation of FIX/FIXa activity.

Examples 6A and 6B

Systemic Anticoagulation Model In Swine

Examples 6A and 6B pertain to the evaluation of the ability of the truncated FIX/FIXa aptamer, RNA 9.3 truncated aptamer $9.3^t$ (SEQ ID NO:70), to systemically anti-coagulate small (2-4 kg) swine. The evaluation included three groups with 3 animals per group. The groups are vehicle control (20 mM Hepes, pH 7.4; 150 mM NaCl; 2 mM $CaCl_2$), about 0.5 mg/kg aptamer in vehicle, and about 1.0 mg/kg aptamer in vehicle.

The following procedures were performed for each animal. Under anesthesia, a venous catheter was placed in the femoral vein of the pig for sample injection, and an arterial catheter was placed in the femoral artery for serial withdrawal of blood samples. Prior to injection, and at times thereafter, blood samples were taken and processed. One portion of the sample (~0.4 mls) was used to measure, on site, an activated clotting time (ACT) to establish a baseline whole blood clot time for each animal A second portion of the sample (~2.7 mls) was aliquoted into citrate-containing Vacutainer™ tubes and processed to prepare plasma for coagulation assays (e.g. aPTT's). A third portion of sample (~2.5 mls) was aliquoted into EDTA-containing Vacutainer™ tubes and processed to prepare plasma to be used in the measurement of the plasma aptamer concentration. In addition, CBC's were performed prior to injection and at the end of the study.

Example 6A

Change in Clot Times Following Injection of Vehicle or FIX/FIXa Aptamer

Referring now to FIG. 3B, the change in the Activated Clotting Time (ACT) following treatment with aptamer was measured. The ACT increase is the ratio of the (pre-injection ACT/post injection ACT) for each time point, 1.0=no change (time 0=pre-injection). There is a clear dose-dependent increase in the ACT of the aptamer but not vehicle treated animals, with a peak at ~4 min post injection for the low dose, and 4-6 min post injection for the high dose. At the lower dose, the effect persists out to nearly 15 minutes post injection, while at the higher dose the ACT is still elevated at the conclusion of the experiment. Data is presented as the mean±sem.

Referring now to FIG. 3C, the change in the Prothrombin Time (PT) and activated Partial Thromboplastin Time (aPTT) following treatment with aptamer was also measured. The increase in the PT or APTT is the ratio of the (pre-injection clot time/post injection clot time) for each time point, 1.0=no change (time 0=pre-injection). The PT is sensitive to inhibitors of coagulation factors II, V, VII, and X, but not to inhibitors of factors VIII or IX. The APTT is sensitive to inhibitors of factor IX/IXa. There is a clear dose-dependent increase in the aPTT of aptamer treated but not vehicle treated animals, with the peak increase occurring at the earliest time point taken (1 minute). In contrast, the PT is unaffected by vehicle or either dose of aptamer, demonstrating the functional specificity of the FIX/FIXa aptamer for its target versus other coagulation factors.

An important difference between the aPTT/PT assays and the ACT assay is that in the aPTT and PT assays, the plasma is pre-warmed (3-5 minutes) ex vivo prior to measuring the clotting time. Therefore, while the ACT likely reflects the dynamics of the drug action in vivo (plasma distribution, kinetics of target binding etc.), the aPTT likely reflects the total plasma concentration of the aptamer at a given time post-injection. In FIG. 3C, data is presented as the mean±sem.

Example 6B

Change in Clot Times Following Injection of 0.5 mg/kg 5' Cholesterol

Modified FIX/FIXA Aptamer Versus Unmodified FIX/FIXa Aptamer

Figure 5A:
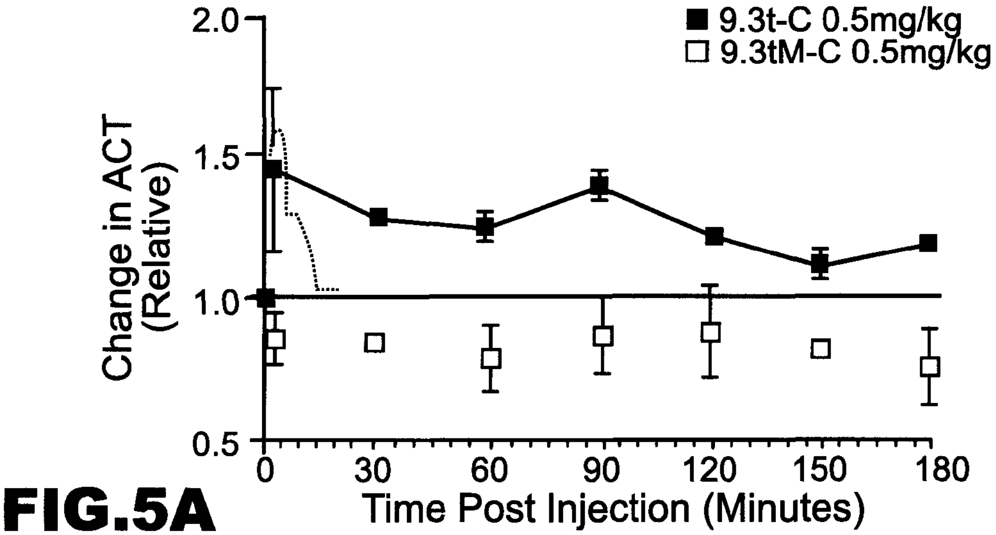
FIGS. 5A-5C depict in vivo anticoagulant activity of aptamer $9.3^{t-C.}$
Figure 5B:
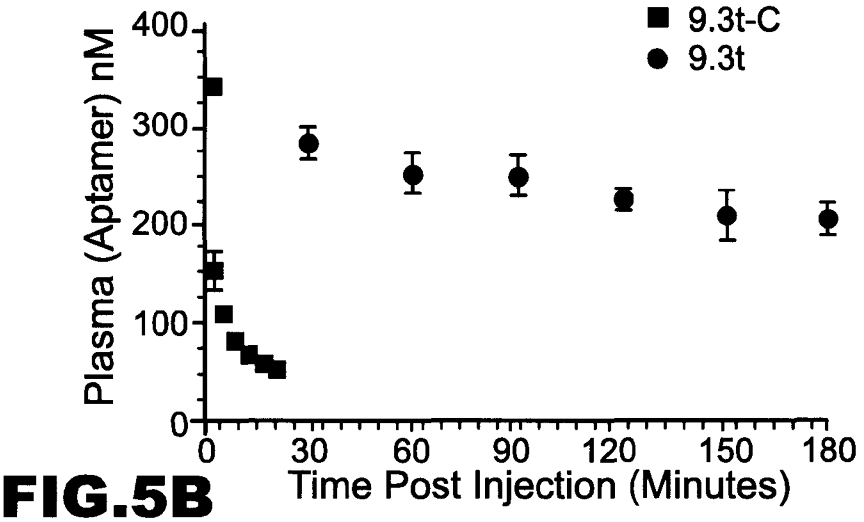

Referring now to FIGS. 5A and 5B, the change in the ACT following treatment with the cholesterol-modified aptamer was evaluated. The addition of cholesterol to an aptamer is expected to increase the plasma residence time of an aptamer following intravenous injection. The ACT increase is the ratio of the (pre-injection ACT/post injection ACT) for each time point, 1.0=no change (time 0=pre-injection). The duration of the increase in the ACT of the pig is clearly longer following injection of the cholesterol modified aptamer, RNA 9.3 truncated aptamer $9.3^{t-c}$ (SEQ ID NO:70)-C, versus RNA 9.3 truncated aptamer $9.3^t$ (SEQ ID NO:70). Following treatment with $9.3^t$, the effect persists out to between 15 to 20 minutes post injection, while following treatment with RNA 9.3 truncated aptamer $9.3^{t-c}$ (SEQ ID NO:70)-C, the ACT is still elevated at the conclusion of the experiment (about 180 minutes). Data is presented in FIGS. 5A and 5B is the average of duplicate measurements at each time point.

Figure 5C:
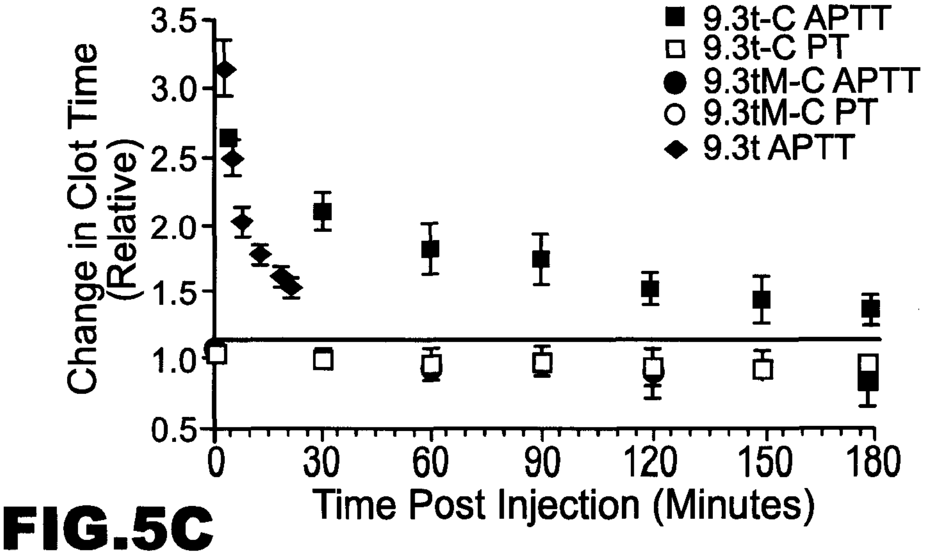

Referring now to FIG. 5C, the change in the PT and aPTT following treatment with cholesterol-modified aptamer is depicted. The increase in the PT or aPTT is the ratio of the (pre-injection clot time/post injection clot time) for each time point, 1.0=no change (time 0=pre-injection). The PT is sensitive to inhibitors of coagulation factors II, V, VII, and X, but not to inhibitors of factors VIII or IX. The aPTT is sensitive to inhibitors of factor IX/IXa. There is a clear dose-dependent increase in the aPTT of aptamer treated animals with the peak increase occurring at the earliest time point taken (1 minute); whereas the PT is unaffected by either aptamer (see also FIG. 3C).

Continuing with FIG. 5C, following treatment with RNA 9.3 truncated aptamer 9.3t (SEQ ID NO:70), the effect persists out to between about 30 minutes post injection (see also FIG. 3C), while following treatment with RNA 9.3 truncated aptamer 9.3t–c (SEQ ID NO:70)-C, the aPTT is still elevated at the conclusion of the experiment (about 180 minutes). In addition, although both aptamers give a similar initial aPTT increase, the increase in the aPTT of the pig following injection of RNA 9.3 truncated aptamer $9.3^{t-c}$ (SEQ ID NO:70)-C is greater than that increase following treatment with RNA 9.3 truncated aptamer $9.3^{t}$ (SEQ ID NO:70). This indicates that the plasma concentration of RNA 9.3 truncated aptamer $9.3^{t}$ (SEQ ID NO:70)-C decreases more slowly than the plasma concentration of RNA 9.3 truncated aptamer $9.3^{t}$ (SEQ ID NO:70) following intravenous injection. Data is presented in FIG. 5C is the average of duplicate measurements at each time point.

Example 7

Inhibition of the Activity of Coagulation Factor Xa

Figure 7A:
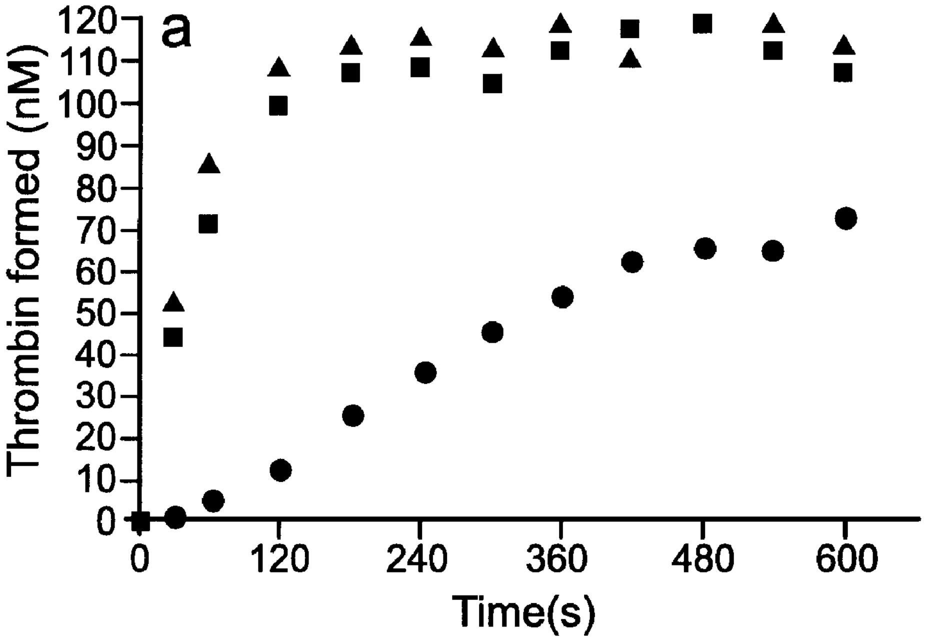
FIG. 7A is a plot of data points depicting that RNA 10.14 (SEQ ID NO:73) inhibits the FXa/FVa catalyzed activation of prothrombin, thereby demonstrating that RNA 10.14 inhibits the activity of coagulation factor Xa. Factor Xa (0.5 nM) was equilibrated with no RNA (▲), 100 nM control RNA (■), or 100 nM RNA 10.14 (●, SEQ ID NO:73). The prothrombin activation reaction was initiated by the addition of FVa (1 nM), PC/PS vesicles (100 μM) and prothrombin (200 nM), and the amount of thrombin formed over time at 37 C was measured.

RNA 10.14 (SEQ ID NO:73) inhibits the FXa/FVa catalyzed activation of prothrombin. As shown in FIG. 7A, factor Xa (0.5 nM) was equilibrated with no RNA (▲), 100 nM control RNA (■), or 100 nM RNA 10.14 (●), the prothrombin activation reaction was initiated by the addition of FVa (1 nM), PC/PS vesicles (100 μM) and prothrombin (200 nM), and the amount of thrombin formed over time at 37° C. was measured.

Figure 7B:
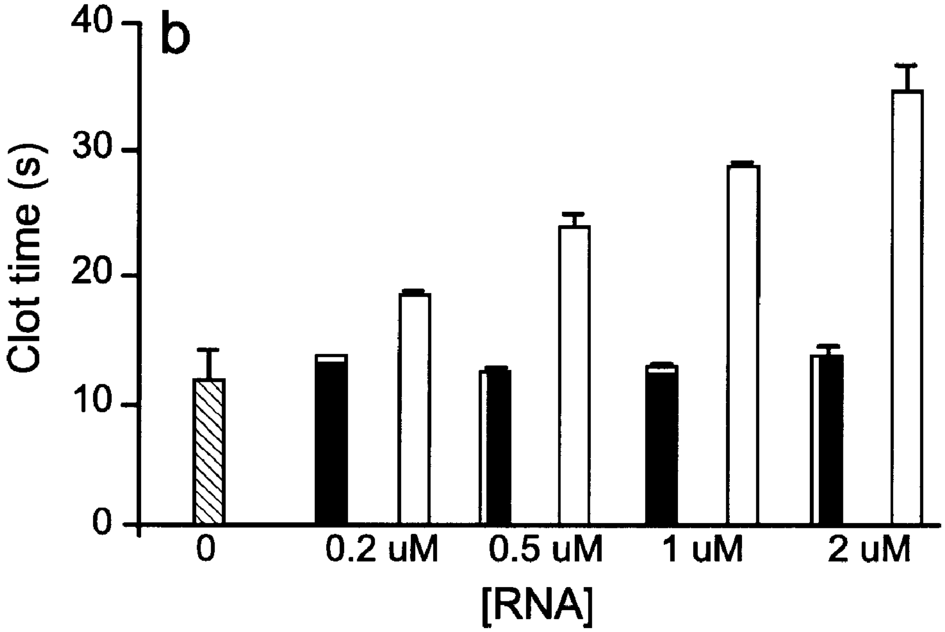
FIG. 7B is a bar graph depicting clotting time, thereby depicting that RNA 10.14 inhibits the activity of coagulation factor Xa The clotting time of normal human plasma was measured in a PT assay in the absence of RNA (striped bar), or in the presence of increasing concentrations of control RNA (solid bar) or RNA 10.14 (open bar). The clotting time is expressed as the mean±sem for duplicate measurements.

Referring now to FIG. 7B, the clotting time of normal human plasma was measured in a PT assay in the absence of RNA (striped bar), or in the presence of increasing concentrations of control RNA (solid bar) or RNA 10.14 (open bar). The clotting time is expressed as the mean±sem for duplicate measurements.

Example 8

Inhibition of Platelet Activation Using Thrombin RNA Aptamers

In this Example the ability of a thrombin RNA aptamer produced by the toggle SELEX method described in Example 3 to inhibit platelet activation was evaluated. Referring to FIGS. 11 and 12, human platelets were isolated and activated by 1 nM human thrombin, in the presence of 30 nM toggle 25 (TOG 25, SEQ ID NO: 55) RNA aptamer or nitrocellulose-binding control RNA aptamer. The protease activated receptor-1 (PAR-1) peptide ligand, SFLLRN (SEQ ID NO: 72), was used as a positive control. As shown in FIG. 12, the TOG 25 aptamer inhibited platelet activation to about 10%, which compared favorably to the platelet samples that included no activator.

Figure 13:
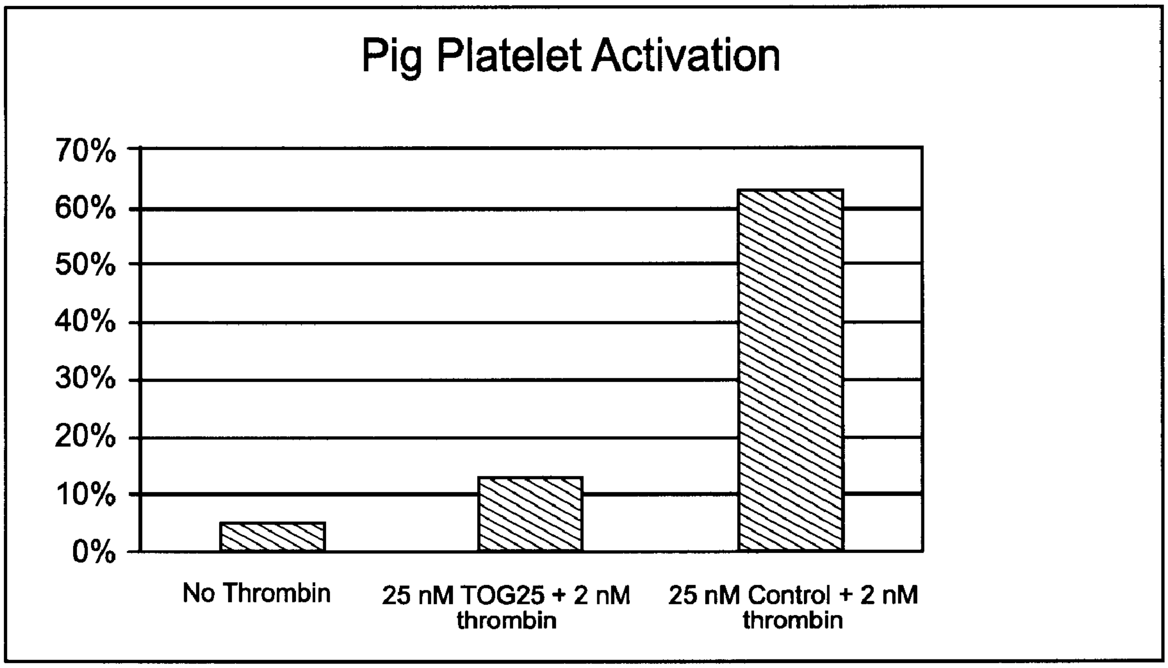
FIG. 13 is a bar graph depicting pig platelet activation by 2 nM pig thrombin, in the presence of 25 nM TOG 25 aptamer (SEQ ID NO: 55) or 25 nM nitrocellulose binding control aptamer.

Referring now to FIG. 13, porcine platelets were isolated and activated by 2 nM porcine thrombin in the presence of the 20 nM TOG 25 RNA aptamer or nitrocellulose-binding control RNA aptamer. As shown in FIG. 13, the TOG 25 aptamer was also able to inhibit pig thrombin in that the activation of the pig platelets was maintained at levels compared to that observed in samples where thrombin was not present.

Figure 14:
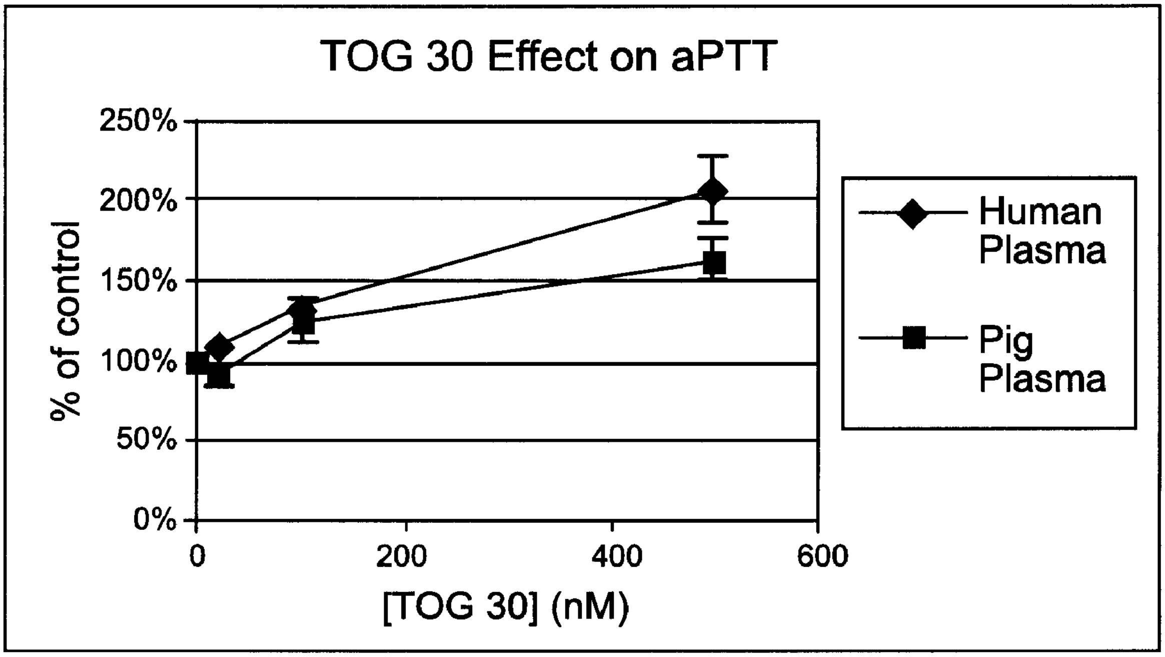
FIG. 14 is a line graph depicting activated partial thromboplastin time assays that were performed on pig (solid diamonds) and human (solid squares) plasma in the presence of increasing concentrations of TOG 30 aptamer (SEQ ID NO: 56). Control aptamer had no effect on APTT at these concentrations.

Referring now to FIG. 14, activated partial thromboplastin time (aPTT) assays were performed on human and pig plasma in the presence of increasing concentrations of the toggle 30 (TOG 30, SEQ ID NO: 56) RNA aptamer that was also prepared using the toggle SELEX method described in Example 3. As shown in FIG. 14, comparable effects were observed in both human and pig plasma with the TOG 30 RNA aptamer. A control aptamer had no effect on aPTT at these concentrations.

The data presented in this Example and in FIGS. 11-14 clearly indicate that the toggle SELEX method disclosed herein to provide aptamers that exhibit selectivity for multiple species. The toggle SELEX method of the present invention thus provides a methodology wherein an aptamer that is selected for a test species as well as an ultimate species in which the treatment is to be applied (e.g., pigs and humans) can be identified. This compatibility facilitates the identification of aptamers or other ligands that have activity in a test animal will also have activity in a subject that will ultimately be treated with the aptamer or other ligand.

Example 9

Mutation Analysis of Antithrombin RNA Aptamer

A proposed secondary structure of a 25 mer truncate of TOG 25 (TOG 25 short, SEQ ID NO: 57), is shown in FIG. 15. The nonmutated or "wild-type" truncate binds human thrombin with a $K_d$ of approximately 1 nM. Continuing with FIG. 15, the binding affinity of various mutants designed to disrupt the proposed stem region, the BULGE region, and the LOOP sequences are shown and are summarized as follows. In the NO STEM mutant, wherein cytosines are mutated to guanidine, the binding affinity is approximately 1 micromolar. In the BULGEUs region, uracil moieties are mutated to adenine and the resulting dissociation constant is much greater than 1 nM. These mutations thus substantially impair the binding affinity of the TOG 25 short aptamer to thrombin. In the LOOPUI mutation, uracil to adenine, produces an aptamer having a dissociation constant of about 250 nM. The LOOPU2 mutation, also uracil to adenine, produces an aptamer having a dissociation constant of about 1 nM. Thus, the mutations in the STEM and BULGE regions have greater impact than those in the LOOP regions.

Figure 16:
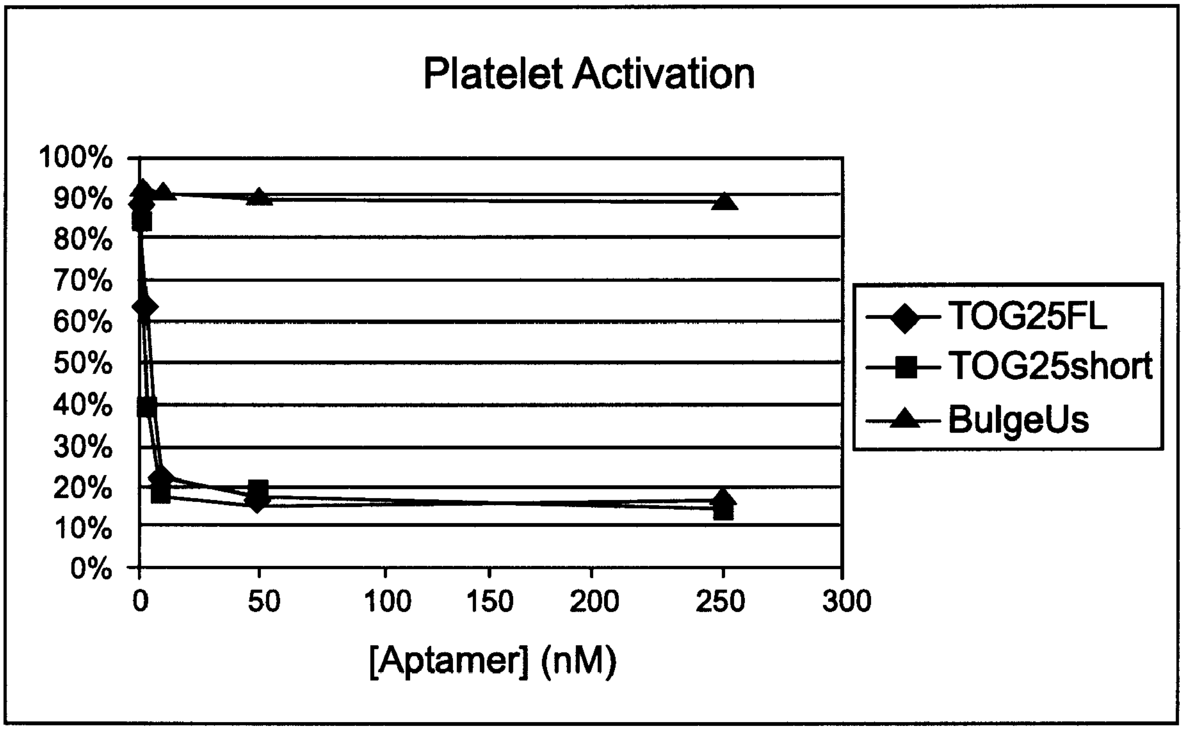
FIG. 16 is a line graph depicting activation of human platelets by 1 nM human thrombin in the presence of increasing concentrations of full length TOG 25 (TOGFL, SEQ ID NO:55, solid diamonds), truncated TOG 25 (TOG 25 short, SEQ ID NO: 57, solid squares), or a non-binding mutant truncate (BULGE Us, SEQ ID NO: 59, solid triAngles).

Referring now to FIG. 16, the ability of the full-length TOG 25 RNA aptamer, the TOG 25 short RNA aptamer, and the BULGEUs RNA aptamer to inhibit platelet activation is analyzed. Human platelets were isolated and activated by 1 nM human thrombin, in the presence of increasing combination of full length TOG 25 (TOG 25 FL, SEQ ID NO: 55), truncated TOG 25 (TOG 25 short, SEQ ID NO: 57), or a non-binding human truncate (BULGEUs, SEQ ID NO: 59). Both the TOG 25 FL and TOG 25 short aptamers substantially inhibit platelet activation, with observed levels of platelet activation below 20%. In contrast, the mutant BULGEUs aptamer did not demonstrate an ability to inhibit platelet activation, with activation levels of approximately 90%. These data thus provide guidance to the design and selection of aptamers that provide the desired modulator effects.

Example 10

Inhibition of the Activity of Coagulation Factor VIIa

Figure 19A:
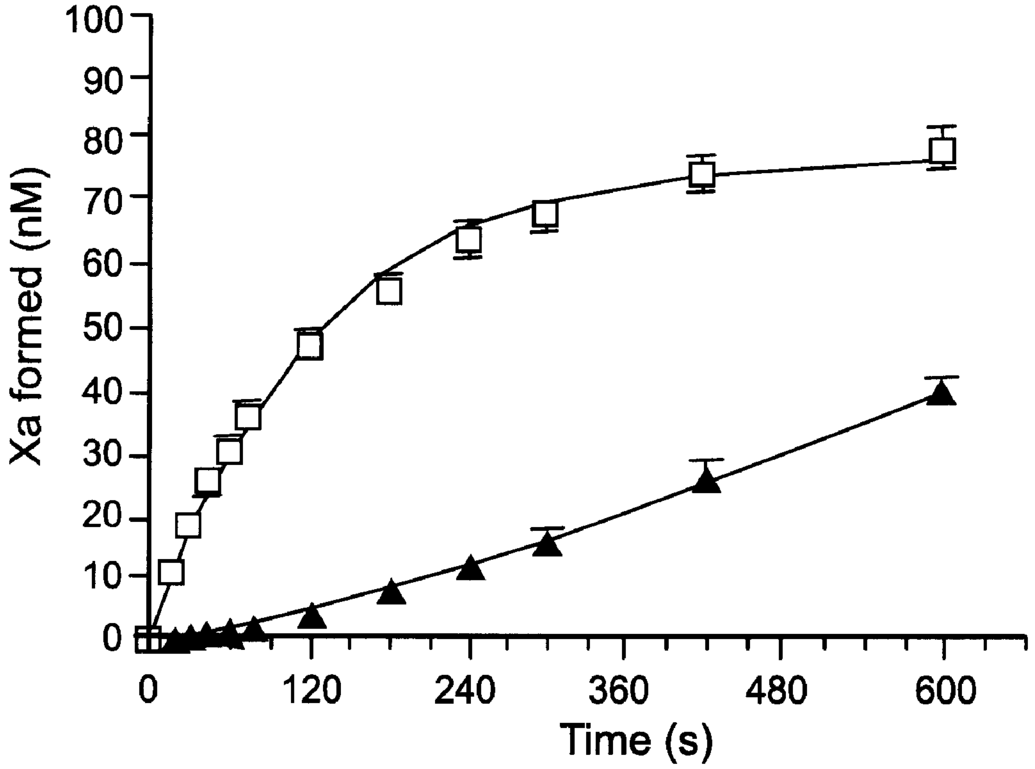
FIG. 19A is a line graph depicting that RNA 16.3 (SEQ ID NO: 41) inhibits the FVIIa/TF catalyzed activation of FX. Factors VIIa and X were equilibrated with no RNA (□), 1 μM RNA 16.3 m4 (■), or 1 μM RNA 16.3 (▲). The FX activation reaction was initiated by the addition of lipidated tissue factor, and the amount of FXa formed over time at 25° C. was measured. The amount of FXa formed over time is expressed as the mean±sem for three more experiments.
Figure 19B:
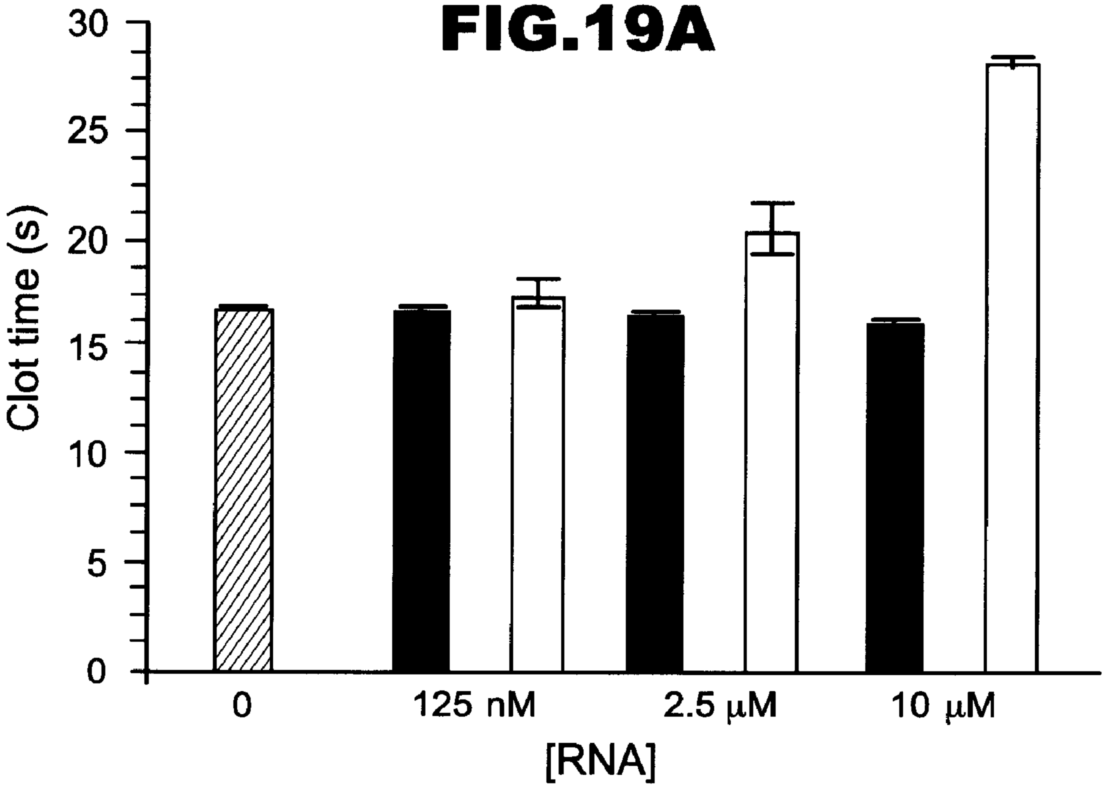
FIG. 19B is a bar graph that depicts that RNA 16.3 (SEQ ID NO: 41) prolongs the tissue factor induced clotting time of human plasma. The clotting time of normal human plasma was measured in a PT assay in the absence of RNA (striped bar), wherein the presence of varying concentrations of 16.3 m4 (solid bar) or RNA 16.3 (open bar). The clotting time is expressed as the mean±SEM for duplicate experiments.

Referring now to FIGS. 19A-19B, a factor VIIa aptamer RNA 16.3 (SEQ ID NO: 41) inhibits the activity of coagulation factor VIIa. RNA 16.3 inhibits the VIIa/TF catalyzed activation of FX. Factors VIIa and X were equilibrated with no RNA (□) 1 mM mutated non-binding RNA 16.3 m4 (■) as a composition control, or 1 μM RNA 16.3 (▲), and the FX activation was initiated by the addition of lapidated tissue factor. The amount of FXa formed over time at 25° C. was measured. The amount of FXa formed over time is expressed as the mean±sem for three or more experiments.

In FIG. 19B, it is shown that RNA 16.3 prolongs the tissue factor induced clotting time of human plasma. The clotting time of human plasma was measured in a PT assay in the absence of RNA (striped bar), wherein the presence of varying concentrations of RNA 16.3 mutated non-binding M4 (solid bar) or 16.3 (open bar). The clotting time is expressed as the mean±sem for duplicate experiments.

Example 11

Inhibition of the Activity of Coagulation Factor VIIa

A nuclease-resistant 2'amino pyrimidine-modified RNA aptamer that can block tissue factor/FVIIa catalyzed FX activation, and that can prolong the clotting time of human plasma are disclosed herein above in Section II.B., in FIG. 10, and in Example 10. While a potent antagonist at room temperature, it was discovered that this antagonist is much less potent at physiologic temperature (likely due to the reduced stability of duplexes containing the 2'amino modification). Therefore, this Example pertains to the generations of additional FVIIa antagonists by performing SELEX using a 2'fluoropyrimidine-modified RNA library at 37° C. (this modification yields duplexes with enhanced stability compared to standard RNA). Eleven (11) rounds of the SELEX experiment were completed.

Following completion of 11 rounds of SELEX against FVIIa, cDNAs from the rounds 10 and 11 pools were cloned and sequenced. Representative sequences are set forth in Table 4 above. The round 11 pool binds FVIIa with a $K_D$ of ~10 nM under physiologic conditions, which represents a >1000 fold enrichment in binding activity for FVIIa over the course of the SELEX process.

Figure 23A:
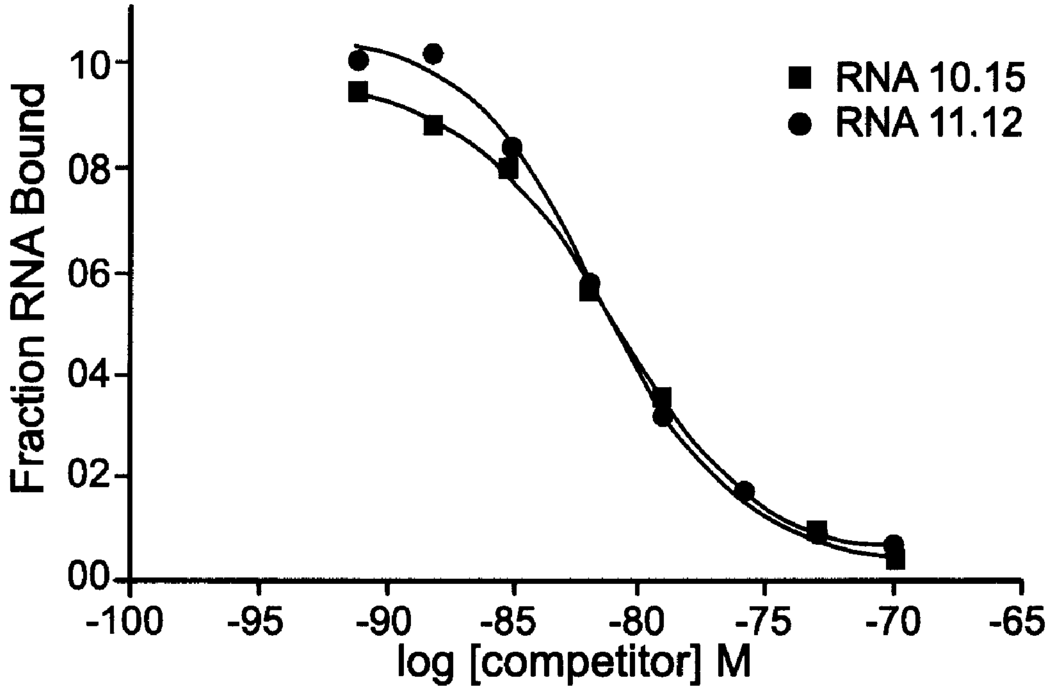
FIGS. 23A and 23B depict binding and inhibitory activity of FVIIa aptamers 10.15 (SEQ ID NO: 75, solid squares) and 11.12 (SEQ ID NO:88, solid diamonds).
Figure 23B:
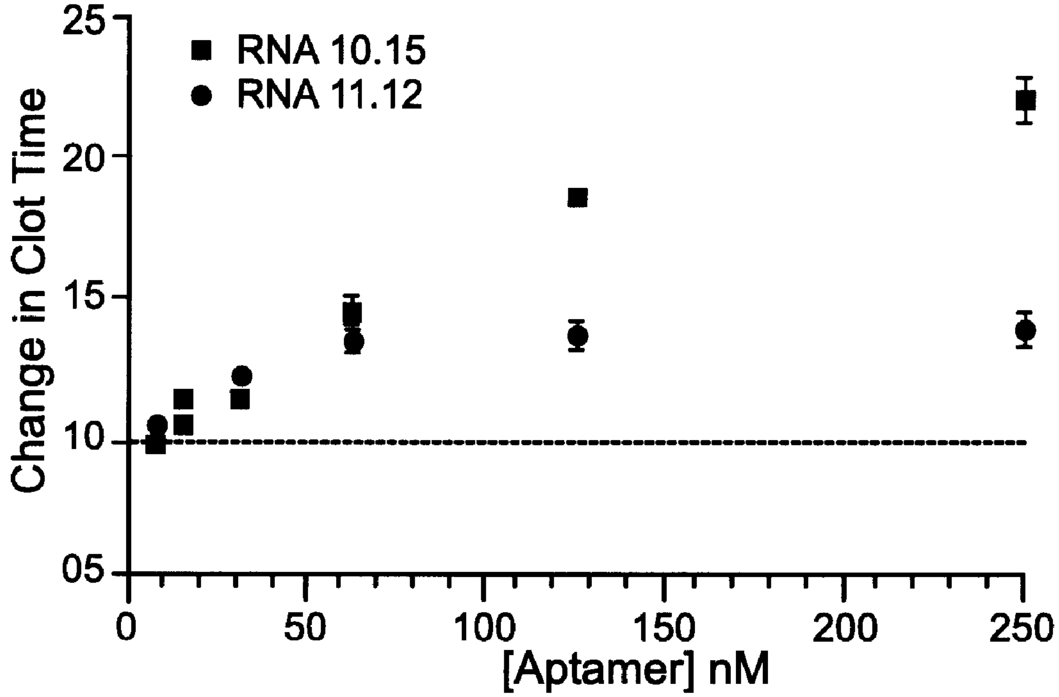

The highest affinity aptamers, sequences 10.15 (SEQ ID NO:75) and 11.12 (SEQ ID NO:88), both bind FVIIa tightly, with apparent $K_d$'s of ~5-8 nM under physiologic conditions (FIG. 23A). Both aptamers bind the zymogen FVII with similar affinity. Aptamers 10.15 and 11.12 are both potent anticoagulants of human plasma in vitro as demonstrated by their ability to prolong Prothrombin Time (PT) clotting assays (FIG. 23B). The in vitro anticoagulant activity of both aptamers is comparable to the anticoagulant activity of the most potent FVIIa antagonists currently available in the art. In addition, neither aptamer prolongs the clotting time of human plasma in Activated Partial Thromboplastin Time (APTT) clotting assays, as expected for specific FVIIa antagonists. Generating active truncates of both of these aptamers allows production of these aptamers by chemical synthesis for in vivo analysis.

Example 12

Inhibition of the Activity of Coagulation Factor Xa

Figure 21:
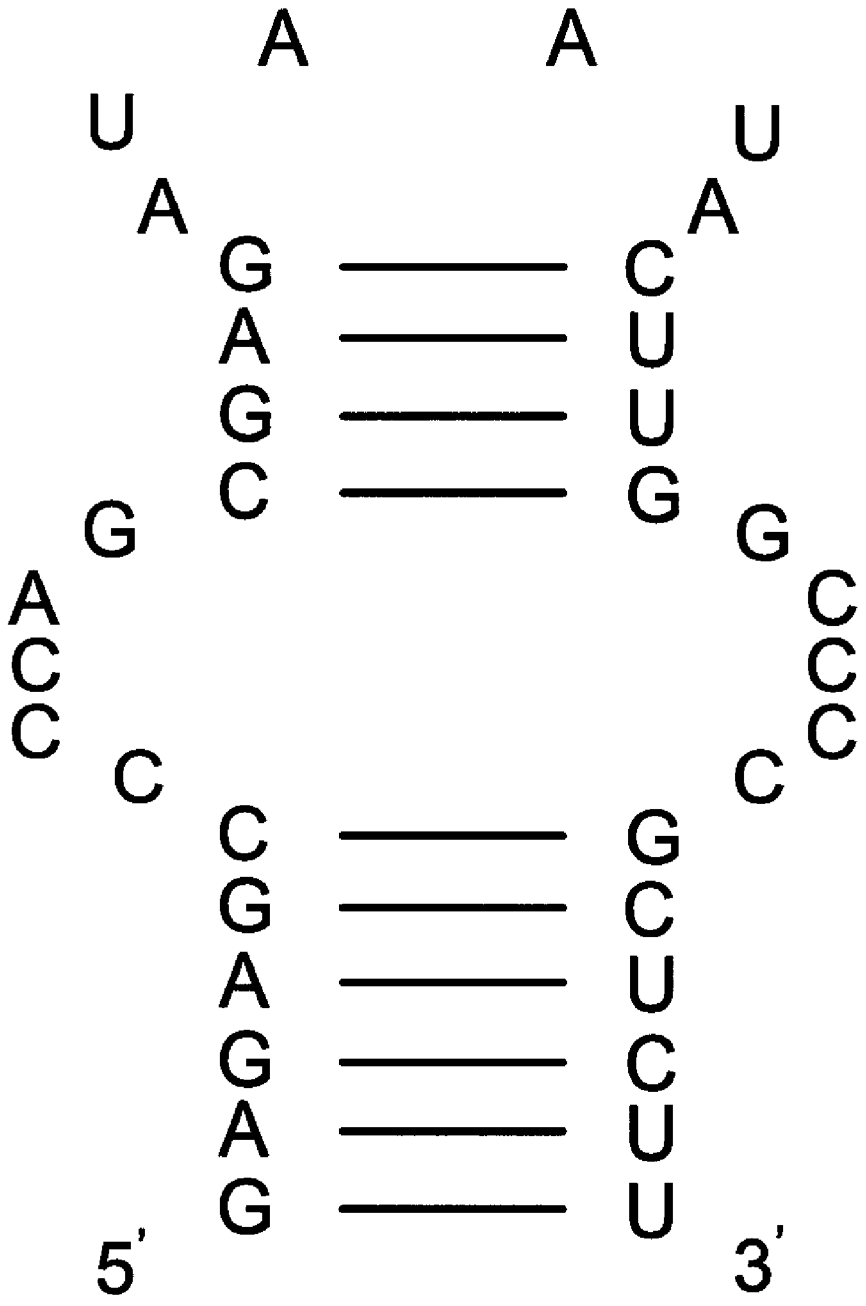
FIG. 21 depicts the secondary structure of the minimal form of the coagulation FXa aptamer 11.F7$^t$ (SEQ ID NO: 148) that retains full binding and inhibitory activity. Secondary structure was predicted by a combination of comparative sequence analysis and RNA folding algorithms.
Figure 22A:
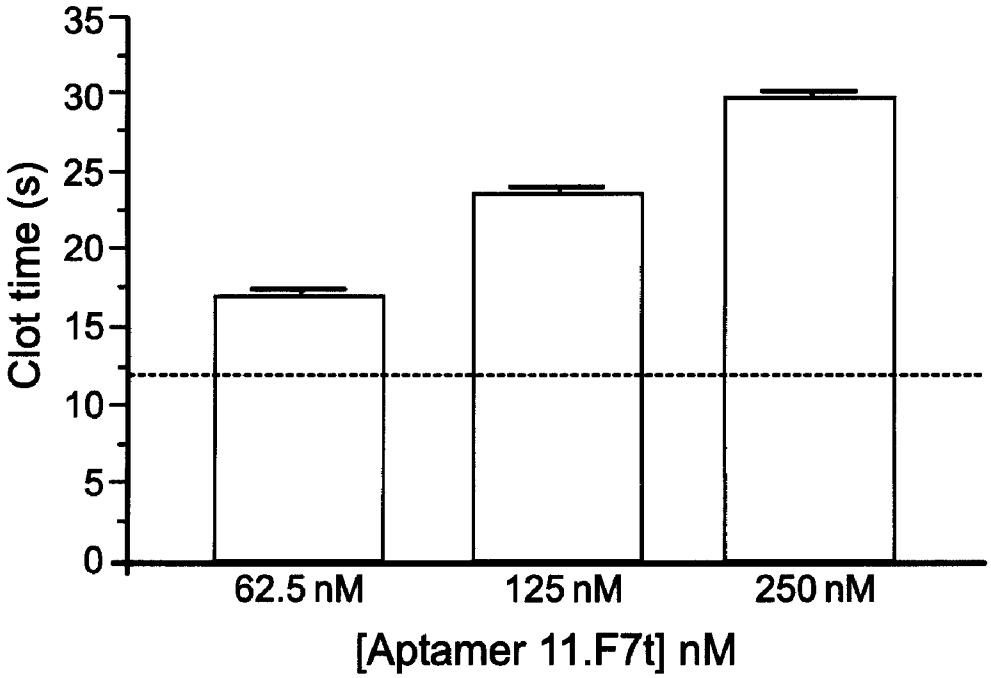
FIG. 22A is a histogram showing prothrombin time (PT) clotting assays in human plasma that demonstrate the anticoagulant activity of 11.7F$^t$ (SEQ ID NO: 148). Dashed lines in histogram represents baseline clotting times in the presence of non-FXa binding control aptamers of similar length.
Figure 22B:
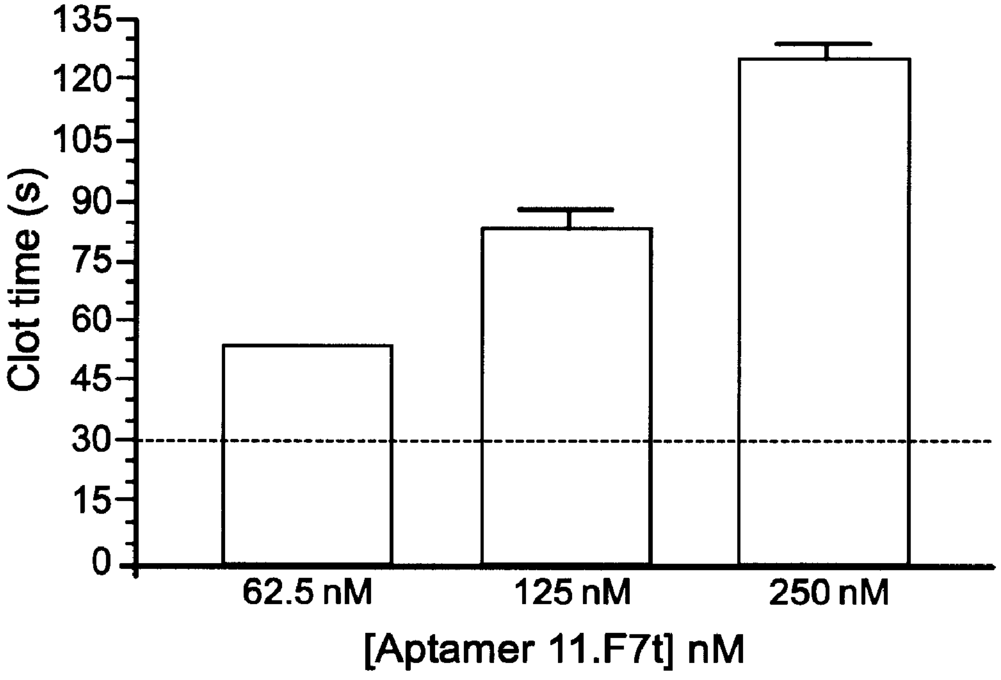
FIG. 22B is a histogram showing activated partial thromboplastin time (APTT) clotting assays in human plasma that demonstrate the anticoagulant activity of 11.F7$^t$ (SEQ ID NO: 148). Dashed lines in histogram represents baseline clotting times in the presence of non-FXa binding control aptamers of similar length.

This Example pertains to the isolation of active truncates of aptamers generated against coagulation factor Xa (FXa). Shown in FIG. 21 is the predicted secondary structure of a fully active 36 nucleotide version of aptamer 11.F7 (SEQ ID NO:148), a sequence related to the aptamer 10.14 (SEQ ID NO:73) described above. This aptamer, termed 11.F7$^t$, binds FXa with an apparent $K_d$ of ~1.5 nM, and exhibits at least several hundred fold specificity for FXa versus related coagulation factors VIIa, IXa, XIa, APC and thrombin. This truncate is a potent anticoagulant of human plasma in vitro as demonstrated by its ability to prolong both the PT (FIG. 22A) and APTT (FIG. 22B) clotting times. Based upon comparison to the in vitro anticoagulant activity of other FXa inhibitors described in the art, this aptamer is one of most potent FXa antagonists described. The activity of this aptamer in animal models of systemic anticoagulation and thrombosis is also provided, in accordance with the in vivo experiments disclosed in previous Examples.

Example 13

Modulation of the Activity of Ang1

Figure 25:
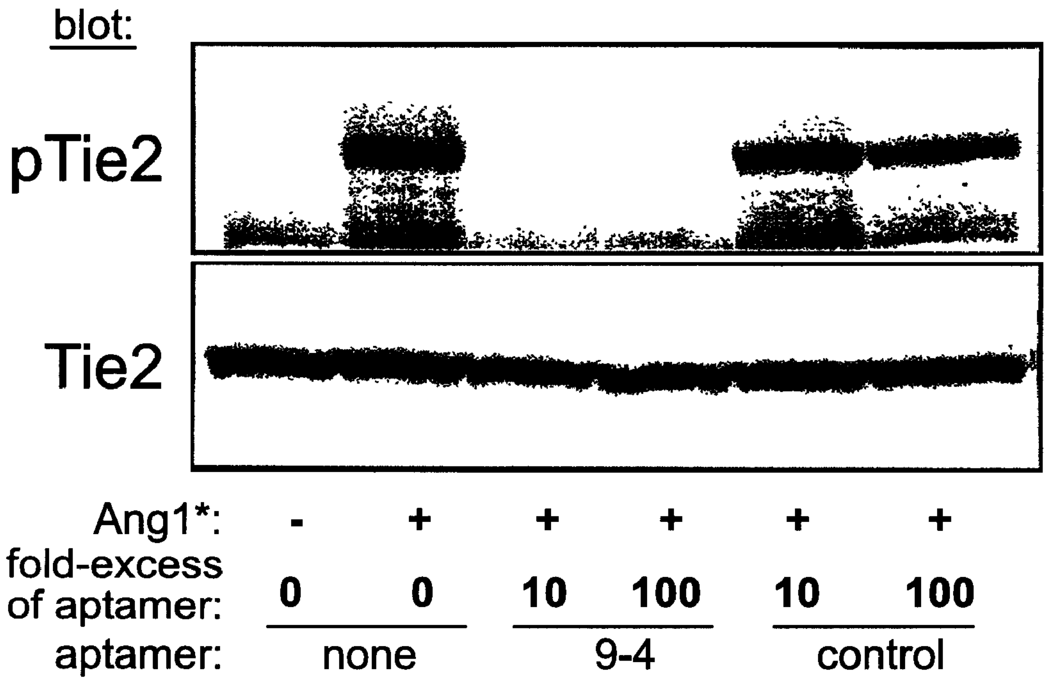
FIG. 25 depicts a Western blot and table that were prepared to determine whether ANG9-4 binding inhibited Ang1 activity. 293 cells expressing human Tie2 were incubated with 13 nM Ang1* with or without a molar excess of 9-4 or control aptamer. ANG9-4 completely abrogated Tie2 autophosphorylation as detected by Western blotting with an antibody specific for phospho-Tie2 (pTie2).

This Example pertains to an analysis of the modulation of Ang1 by Ang1 RNA aptamers. To determine whether ANG9-4 (SEQ ID NO:151) binding inhibited Ang1 activity, 293 cells expressing human Tie2 were incubated with 13 nM Ang1* with or without a molar excess of 9-4 or control aptamer. ANG9-4 completely abrogated Tie2 autophosphorylation as detected by Western blotting with an antibody specific for phospho-Tie2 (pTie2)(see FIG. 25).

Figure 26:
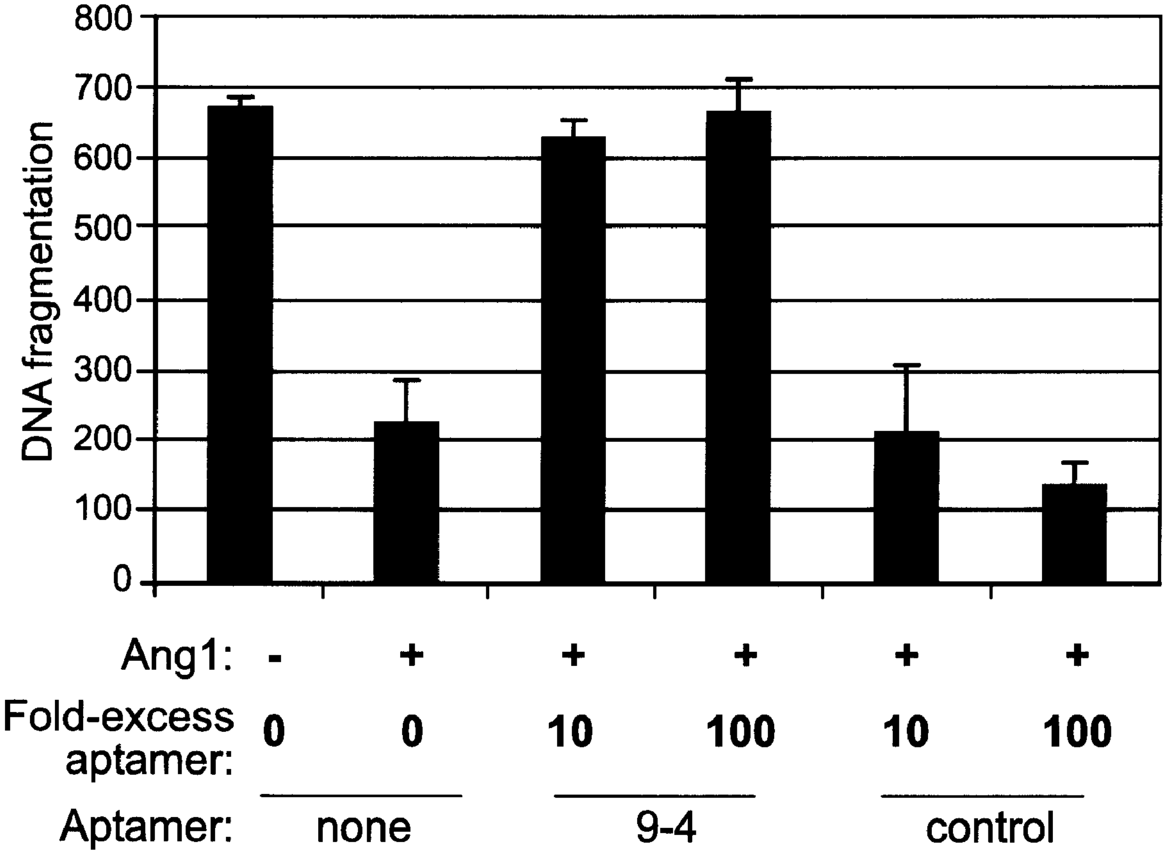
FIG. 26 is a histogram and table showing effect on apoptosis of Ang1 apatmers. Cultured human endothelial cells were serum-starved and treated with TNFα (50 ng/ml) for 3 hours while being incubated with 3.5 nM Ang1* and either ANG9-4 or control aptamer. Apoptosis (DNA fragmentation) was measured by Cell Death Detection ELISA kit (Roche Molecular Biochemicals). ANG9-4, but not control aptamer, increased apoptosis in a dose-dependent manner. Neither 9-4 nor control RNA increased apoptosis in un-starved, untreated cells.

As shown in FIG. 26, cultured human endothelial cells were serum-starved and treated with TNFa (50 ng/ml) for 3 hours while being incubated with 3.5 nM Ang1* and either ANG9-4 or control aptamer. Apoptosis (DNA fragmentation) was measured by Cell Death Detection ELISA kit (Roche Molecular Biochemicals). ANG9-4, but not control aptamer, increased apoptosis in a dose-dependent manner. Neither 9-4 nor control RNA increased apoptosis in un-starved, un-treated cells.

Example 14

Modulation of the Activity of Ang2

Figure 28:
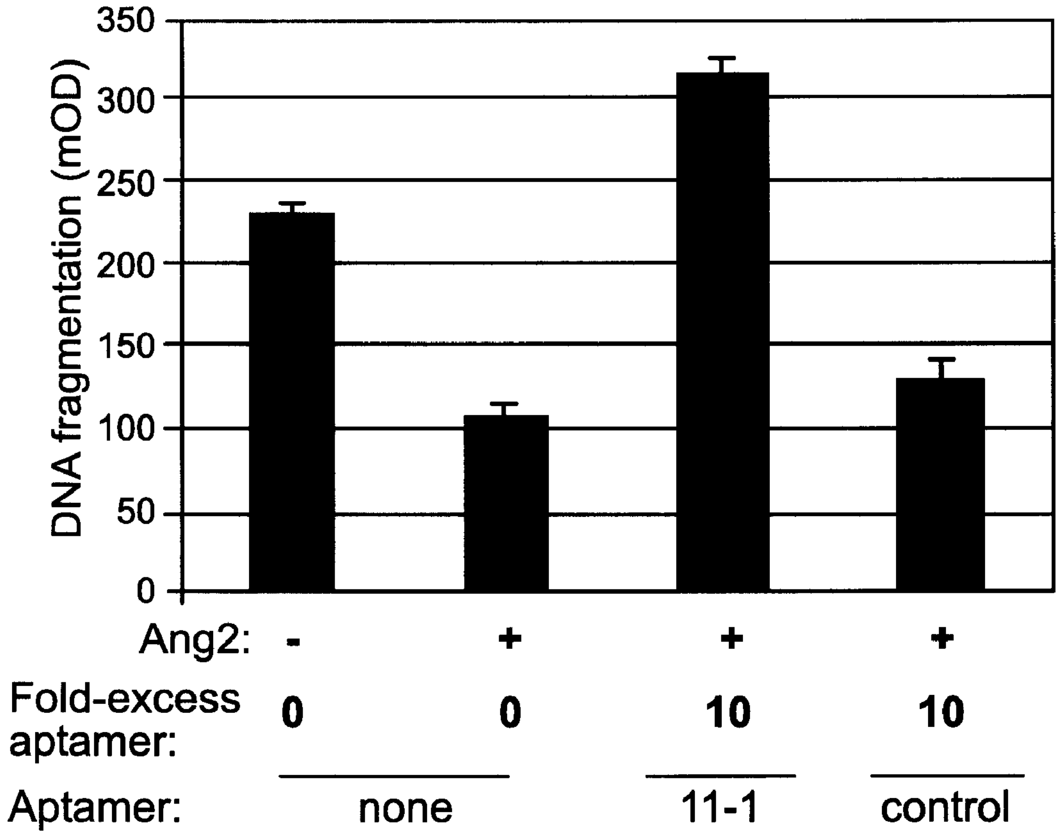
FIG. 28 is a histogram and table showing effect on apoptosis of Ang2 apatmers. Cultured human endothelial cells were serum-starved and treated with TNFα (50 ng/ml) for 3 hours while being incubated with 15 nM Ang2 and either ANG11-1 or control aptamer. Apoptosis (DNA fragmentation) was measured by Cell Death Detection ELISA kit (Roche Molecular Biochemicals). ANG11-1, but not control aptamer, increased apoptosis to a levels above those seen in the absence of exogenous Ang2, suggesting inhibition of both exogenous and endogenous (autocrine) Ang2, which is known to be released by endothelial cells. Neither ANG11-1 nor control RNA increased apoptosis in non-irradiated cells.

As shown in FIG. 28, cultured human endothelial cells were serum-starved and treated with TNFa (50 ng/ml) for 3 hours while being incubated with 15 nM Ang2 and either ANG11-1 or control aptamer. Apoptosis (DNA fragmentation) was measured by Cell Death Detection ELISA kit (Roche Molecular Biochemicals). ANG11-1, but not control aptamer, increased apoptosis to a levels above those seen in the absence of exogenous Ang2, suggesting inhibition of both exogenous and endogenous (autocrine) Ang2, which is known to be released by endothelial cells. Neither ANG11-1 nor control RNA increased apoptosis in non-irradiated cells.

Figure 29:
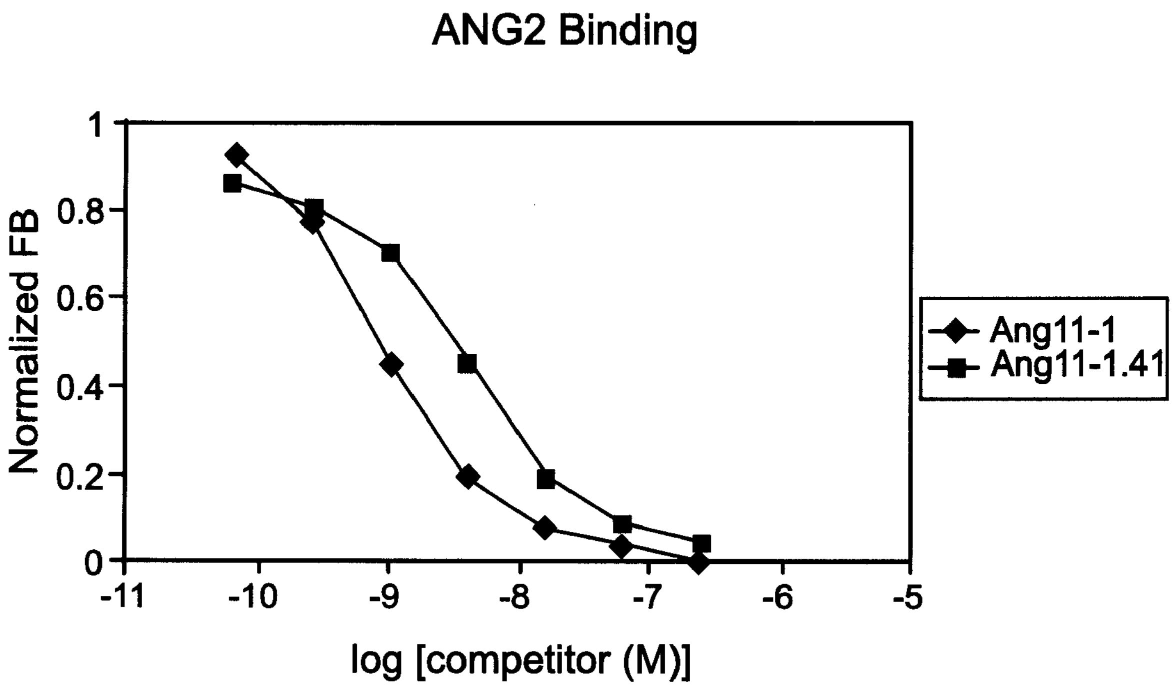
FIG. 29 is a line graph wherein the ability of ANG11-1 and a 41-nucleotide truncate (ANG11-1.41) to compete for binding to ANG2 (normalized to binding in the absence of competitor) is plotted as a function of competitor concentration. ANG11-1.41 (solid squares) competes for ANG2 binding with an affinity ($K_d$~5 nM) only slightly worse that of the full-length RNA aptamer (~1 nM)(solid diamonds).

As in FIG. 29, the ability of ANG11-1 (SEQ ID NO:168) and a 41-nucleotide truncate (ANG11-1.41) (SEQ ID NO:189) to compete for binding to ANG2 (normalized to binding in the absence of competitor) is plotted as a function of competitor concentration. ANG11-1.41 competes for ANG2 binding with an affinity ($K_d$~5 nM) only slightly worse that of the full-length RNA aptamer (~1 nM).

REFERENCES

The references listed below as well as all references cited in the specification are incorporated herein by reference to the extent that they supplement, explain, provide a background for or teach methodology, techniques and/or compositions employed herein.

Chung et al. in *Fibrinogen, Thrombosis, Coagulation and Fibrinolysis* (Liu and Chien, eds.) Lemon Press, New York, pp. 39-48 (1990).
Sherr, C. J., *Cell*, 73:1059-1065 (1993)
Hunter, T., *Cell* 75:839-841 (1993)
Nevins J. R., *Science*, 258:424-429 (1992)
Helin, K. and Harlow, E., *Trends Cell Biol.* 3:43-46 (1993)
La Thangue, N. B., *Trends Biochem. Sci.* 19:180-114 (1994)
Sherr, C. J. and Roberts, J. M., *Genes Dev.* 9:1149-1143 (1995)
Weinberg, R. A. *Cell* 81:323-330 (1995)

*Oligonucleotide Synthesis* (M. J. Gait ed. 1984)
*Nucleic Acid Hybridization* (B. D. Flames & S. J. Higgins eds. 1984)
Sambrook, Fritsch & Maniatis, *Molecular Cloning: A Laboratory Manual*, Second Edition (1989)
*Methods in Enzymology* (S. Colowick and N. Kaplan eds., Academic Press, Inc.).
Chou, P. Y. and Fasman, G. D. (1978) *Biochemistry,* 13:222-245
Gamier et al. (1978) *J. Mol Biol.,* 120:97-120
Beaucage et al. (1981) *Tetrahedr. Letters* 22:1859-1862
Sinha et al., (1984) *Nucleosides and Nucleotides* 3:157-171
R. Iwase et al., (1992), *Nucl. Acids Res.* 20(7):1643-1648
Fukuoda et al., (1993) *Nucleic Acids Symposia* 29:25-26
Remington's Pharmaceutical Sciences
Ozato et al, *Cell Differ.,* 19:237-244 (1986)
Inoue et al, *Cell Differ. Dev.,* 29:123-128 (1990)
Rokkones et al, *J. Comp. Physiol. B,* 158:751-758 (1989)
Guyomard et al, *Biochimie,* 71:857-863 (1989)
Wong and Lohman, 1993, *Proc. Natl. Acad. Sci. USA* 90, 5428-5432
Hobbs et al. *Biochem* 12:5138 (1973)
Guschlbauer et al. *Nucleic Acids Res.* 4:1933 (1977)
Shibahara et al. *Nucl. Acids. Res.* 15:4403 (1987)
Pieken et al. *Science* 253:314 (1991)
Zuker (1989) *Science* 244:48-52
Stormo and Gutell (1992) *Nucleic Acids Research* 29:5785-5795
U.S. Pat. No. 4,244,946
U.S. Pat. No. 5,118,672.
U.S. Pat. No. 5,260,203
U.S. Pat. No. 5,270,162
U.S. Pat. No. 5,475,096
U.S. Pat. No. 5,567,588
U.S. Pat. No. 5,580,722
U.S. Pat. No. 5,580,737
U.S. Pat. No. 5,582,981
U.S. Pat. No. 5,627,158
U.S. Pat. No. 5,639,940
U.S. Pat. No. 5,660,985
U.S. Pat. No. 5,707,796
U.S. Pat. No. 5,734,033
U.S. Pat. No. 5,756,921
U.S. Pat. No. 5,817,785
U.S. Pat. No. 5,846,720
U.S. Pat. No. 5,849,578
U.S. Pat. No. 5,861,254
U.S. Pat. No. 5,861,501
U.S. Pat. No. 6,011,020
PCT Application WO 9203568

It will be understood that various details of the invention can be changed without departing from the scope of the invention. Furthermore, the foregoing description is for the purpose of illustration only, and not for the purpose of limitation—the invention being defined by the claims.

What is claimed is:

1. A method of modulating the biological activity of Ang2 comprising administering to a host an RNA aptamer that binds to Ang2, the aptamer comprising a secondary structure, wherein the secondary structure comprises, in a 5' to 3' direction, a first stem region, a first loop region, a second stem region, a second loop region, a third loop region, a third stem region, a fourth loop region, and a fifth loop region, and wherein the aptamer further comprises a consensus sequence comprising AUCAGC.

2. The method of claim 1, wherein the aptamer comprises at least one 2'-modified nucleotide.

3. The method of claim 2, wherein the aptamer comprises at least one modified nucleotide selected from the group consisting of a 2'-halo-modified nucleotide, and a 2'-O-alkyl-modified nucleotide.

4. The method of claim 2, wherein the aptamer comprises at least one 2'-fluorocytidine or one 2'-fluorouridine.

5. The method of claim 2, wherein the aptamer comprises cytidines that are all 2'-deoxy-2'-fluorocytidine, or uridines that are all 2'-deoxy-2'-fluorouridine.

6. The method of claim 2, wherein the aptamer comprises at least one 2'-O-alkyl-modified nucleotide.

7. The method of claim 1, wherein the aptamer further comprises a covalently linked carrier selected from the group consisting of a soluble polymer, a biodegradable polymer, polyethylene glycol, and cholesterol.

8. The method of claim 1, wherein the aptamer is administered orally, topically to a vascular tissue, intravenously, intraperitoneally, intramuscularly, subcutaneously, intra-cavity, transdermally, or by peristaltic techniques.

9. The method of claim 8, wherein topical administration comprises coating or impregnating a blood vessel tissue with a gel comprising the aptamer and implanting the coated or impregnated vessel in place of a damaged or diseased vessel tissue segment in the host.

10. The method of claim 8, wherein topical administration comprises delivery via a catheter to a vessel or vessels in the host.

11. The method of claim 8, wherein topical administration comprises pumping an aptamer composition of the present invention into a vessel that is to be implanted into the host.

12. The method of claim 1, wherein the aptamer is administered at a dosage from about 1 μg/kg body weight to about 1 mg/kg body weight.

13. The method of claim 1, wherein the aptamer comprises a nucleotide sequence selected from the group consisting of SEQ ID NOs: 168, 170, 171, 175, 177, 179, and 183.

14. The method of claim 13, wherein the aptamer comprises the nucleotide sequence of SEQ ID NO: 168 or a truncate thereof.

15. The method of claim 1, wherein the aptamer comprises the nucleotide sequence SEQ ID NO: 187.

16. A method of modulating the biological activity of Ang2 comprising administering to a host an RNA aptamer that binds to Ang2, the aptamer comprising a nucleotide sequence selected from the group consisting of SEQ ID NOs: 169, 172, 173, 174, 176, 178, 180-182, and 184-186.

17. The method of claim 16, wherein the aptamer comprises at least one 2'-modified nucleotide.

18. The method of claim 17, wherein the aptamer comprises at least one modified nucleotide selected from the group consisting of a 2'-halo-modified nucleotide, and a 2'-O-alkyl-modified nucleotide.

19. The method of claim 17, wherein the aptamer comprises at least one 2'-fluorocytidine or one 2'-fluorouridine.

20. The method of claim 17, wherein the aptamer comprises cytidines that are all 2'-deoxy-2'-fluorocytidine, or uridines that are all 2'-deoxy-2'-fluorouridine.

21. The method of claim 17, wherein the aptamer comprises at least one 2'-O-alkyl-modified nucleotide.

22. The method of claim 16, wherein the aptamer further comprises a covalently linked carrier selected from the group consisting of a soluble polymer, a biodegradable polymer, polyethylene glycol, and cholesterol.

23. The method of claim 16, wherein the aptamer is administered orally, topically to a vascular tissue, intravenously, intraperitoneally, intramuscularly, subcutaneously, intra-cavity, transdermally, or by peristaltic techniques.

24. The method of claim 23, wherein topical administration comprises coating or impregnating a blood vessel tissue with a gel comprising the aptamer and implanting the coated or impregnated vessel in place of a damaged or diseased vessel tissue segment in the host.

25. The method of claim 24, wherein topical administration comprises delivery via a catheter to a vessel or vessels in the host.

26. The method of claim 24, wherein topical administration comprises pumping an aptamer composition of the present invention into a vessel that is to be implanted into the host.

27. The method of claim 16, wherein the aptamer is administered at a dosage from about 1 μg/kg body weight to about 1 mg/kg body weight.

28. The method of claim 16, wherein the aptamer is a truncate of SEQ ID NOs: 169, 172, 173, 174, 176, 178, 180-182, or 184-186.

* * * * *

SEQUENCE LISTING

```
<160> NUMBER OF SEQ ID NOS: 243

<210> SEQ ID NO 1
<211> LENGTH: 96
<212> TYPE: RNA
<213> ORGANISM: Artificial Sequence
<220> FEATURE:
<223> OTHER INFORMATION: RNA aptamer

<400> SEQUENCE: 1

gggagagagg aagagggaug ggccgccagu gggaagcuau acccaacgcc ccagccccag     60

agcauaaccc agaggucgau aguacuggau cccccc                               96


<210> SEQ ID NO 2
<211> LENGTH: 96
<212> TYPE: RNA
<213> ORGANISM: Artificial Sequence
<220> FEATURE:
<223> OTHER INFORMATION: RNA aptamer

<400> SEQUENCE: 2

gggagagagg aagagggaug ggcuauauac acgcugguga ucccaucuca auugaaacaa     60

cacauaaccc agaggucgau aguacuggau cccccc                               96


<210> SEQ ID NO 3
<211> LENGTH: 96
<212> TYPE: RNA
<213> ORGANISM: Artificial Sequence
<220> FEATURE:
<223> OTHER INFORMATION: RNA aptamer

<400> SEQUENCE: 3

gggagagagg aagagggaug gggacuauac cgcguaaugc ugccucccca uuccggaacg     60
```

-continued

```
cucauaaccc agaggucgau aguacuggau cccccc                           96


<210> SEQ ID NO 4
<211> LENGTH: 95
<212> TYPE: RNA
<213> ORGANISM: Artificial Sequence
<220> FEATURE:
<223> OTHER INFORMATION: RNA aptamer

<400> SEQUENCE: 4

gggagagagg aagagggaug ggcacuauac gcaucuugcu gccugcccgc gagucaaauu    60

gcauaaccca gaggucgaua guacuggauc ccccc                            95


<210> SEQ ID NO 5
<211> LENGTH: 96
<212> TYPE: RNA
<213> ORGANISM: Artificial Sequence
<220> FEATURE:
<223> OTHER INFORMATION: RNA aptamer

<400> SEQUENCE: 5

gggagagagg aagagggaug ggccuaccag uucguggcua gcgugacgua ccacccaggg    60

accauaaccc agaggucgau aguacuggau cccccc                           96


<210> SEQ ID NO 6
<211> LENGTH: 96
<212> TYPE: RNA
<213> ORGANISM: Artificial Sequence
<220> FEATURE:
<223> OTHER INFORMATION: RNA aptamer

<400> SEQUENCE: 6

gggagagagg aagagggaug ggcgauaacc aacaugguga ucccauucau cauacccuac    60

aacauaaccc agaggucgau aguacuggau cccccc                           96


<210> SEQ ID NO 7
<211> LENGTH: 96
<212> TYPE: RNA
<213> ORGANISM: Artificial Sequence
<220> FEATURE:
<223> OTHER INFORMATION: RNA aptamer

<400> SEQUENCE: 7

gggagagagg aagagggaug gggccaccua cuauaccggu caucgugcau aggucgcugc    60

cacauaaccc agaggucgau aguacuggau cccccc                           96


<210> SEQ ID NO 8
<211> LENGTH: 95
<212> TYPE: RNA
<213> ORGANISM: Artificial Sequence
<220> FEATURE:
<223> OTHER INFORMATION: RNA aptamer

<400> SEQUENCE: 8

gggagagagg aagagggaug ggucucacac ccgaagaugg ccaaagaggg agaugaguuu    60

ccauaaccca gaggucgaua guacuggauc ccccc                            95


<210> SEQ ID NO 9
<211> LENGTH: 96
<212> TYPE: RNA
<213> ORGANISM: Artificial Sequence
<220> FEATURE:
```

-continued

<223> OTHER INFORMATION: RNA aptamer

<400> SEQUENCE: 9
gggagagagg aagagggaug ggacuauauu cggaaucugg acucccaccu gccugcccca 60
gacauaaccc agaggucgau aguacuggau cccccc 96

<210> SEQ ID NO 10
<211> LENGTH: 96
<212> TYPE: RNA
<213> ORGANISM: Artificial Sequence
<220> FEATURE:
<223> OTHER INFORMATION: RNA aptamer

<400> SEQUENCE: 10
gggagagagg aagagggaug ggcgauauac acauugguga ucccacccac augaaaccac 60
agcauaaccc agaggucgau aguacuggau cccccc 96

<210> SEQ ID NO 11
<211> LENGTH: 96
<212> TYPE: RNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (1)..(96)
<223> OTHER INFORMATION: "n" = g, c, u or a

<400> SEQUENCE: 11
gggagagagg aagagggaug ggcucaucac aggcgaagug aacaacacua ccgncnaguu 60
accauaaccc agaggucgau aguacuggau cccccc 96

<210> SEQ ID NO 12
<211> LENGTH: 95
<212> TYPE: RNA
<213> ORGANISM: Artificial Sequence
<220> FEATURE:
<223> OTHER INFORMATION: RNA aptamer

<400> SEQUENCE: 12
gggagagagg aagagggaug gggacuauac gugaacgacu gcauccacuu ccccgccaug 60
gcauaaccca gaggucgaua guacuggauc ccccc 95

<210> SEQ ID NO 13
<211> LENGTH: 96
<212> TYPE: RNA
<213> ORGANISM: Artificial Sequence
<220> FEATURE:
<223> OTHER INFORMATION: RNA aptamer

<400> SEQUENCE: 13
gggagagagg aagagggaug ggccauacgu ggacgacugc acccgacccu ucagcccagg 60
uccauaaccc agaggucgau aguacuggau cccccc 96

<210> SEQ ID NO 14
<211> LENGTH: 96
<212> TYPE: RNA
<213> ORGANISM: Artificial Sequence
<220> FEATURE:
<223> OTHER INFORMATION: RNA aptamer

<400> SEQUENCE: 14
gggagagagg aagagggaug ggaccauacg cacauugcug aaucccccuc aauagcaccu 60

-continued accauaaccc agaggucgau aguacuggau cccccc 96

<210> SEQ ID NO 15
<211> LENGTH: 96
<212> TYPE: RNA
<213> ORGANISM: Artificial Sequence
<220> FEATURE:
<223> OTHER INFORMATION: RNA aptamer
<220> FEATURE:
<221> NAME/KEY: misc_feature
<222> LOCATION: (54)..(54)
<223> OTHER INFORMATION: "n" = c or u

<400> SEQUENCE: 15
gggagagagg aagagggaug ggccauaacc acuuugguga acccacccag cucnugugau 60
ugcauaaccc agaggucgau aguacuggau cccccc 96

<210> SEQ ID NO 16
<211> LENGTH: 96
<212> TYPE: RNA
<213> ORGANISM: Artificial Sequence
<220> FEATURE:
<223> OTHER INFORMATION: RNA aptamer

<400> SEQUENCE: 16
gggagagagg aagagggaug ggaccauaac gacuacucgu gaaucccacc aucagcgcac 60
aacauaaccc agaggucgau aguacuggau cccccc 96

<210> SEQ ID NO 17
<211> LENGTH: 96
<212> TYPE: RNA
<213> ORGANISM: Artificial Sequence
<220> FEATURE:
<223> OTHER INFORMATION: RNA aptamer

<400> SEQUENCE: 17
gggagagagg aagagggaug gggacuauac cggcaaucgu gcauccccug gaccuaacaa 60
uacauaaccc agaggucgau aguacuggau cccccc 96

<210> SEQ ID NO 18
<211> LENGTH: 96
<212> TYPE: RNA
<213> ORGANISM: Artificial Sequence
<220> FEATURE:
<223> OTHER INFORMATION: RNA aptamer

<400> SEQUENCE: 18
gggagagagg aagagggaug ggaacaccau uaaugcucgg ccagguaacc ccggcgcaua 60
cucauaaccc agaggucgau aguacuggau cccccc 96

<210> SEQ ID NO 19
<211> LENGTH: 96
<212> TYPE: RNA
<213> ORGANISM: Artificial Sequence
<220> FEATURE:
<223> OTHER INFORMATION: RNA aptamer

<400> SEQUENCE: 19
gggagagagg aagagggaug gggaccauaa cucuaacggg ugaaucccgc aucucgacaa 60
uacauaaccc agaggucgau aguacuggau cccccc 96

<210> SEQ ID NO 20

```
<211> LENGTH: 95
<212> TYPE: RNA
<213> ORGANISM: Artificial Sequence
<220> FEATURE:
<223> OTHER INFORMATION: RNA aptamer

<400> SEQUENCE: 20

gggagagagg aagagggaug ggugauaacc acucugguga accccucccg acuugcucgc    60

acauaaccca gaggucgaua guacuggauc ccccc                              95

<210> SEQ ID NO 21
<211> LENGTH: 96
<212> TYPE: RNA
<213> ORGANISM: Artificial Sequence
<220> FEATURE:
<223> OTHER INFORMATION: RNA aptamer

<400> SEQUENCE: 21

gggagagagg aagagggaug gguaauaacu guauggugaa cccacccaaa cucccauggc    60

uacauaaccc agaggucgau aguacuggau cccccc                             96

<210> SEQ ID NO 22
<211> LENGTH: 95
<212> TYPE: RNA
<213> ORGANISM: Artificial Sequence
<220> FEATURE:
<223> OTHER INFORMATION: RNA aptamer

<400> SEQUENCE: 22

gggagagagg aagagggaug ggcgccauac gcacauugcu gcaucgccuu cccguaagaa    60

ccauaaccca gaggucgaua guacuggauc ccccc                              95

<210> SEQ ID NO 23
<211> LENGTH: 96
<212> TYPE: RNA
<213> ORGANISM: Artificial Sequence
<220> FEATURE:
<223> OTHER INFORMATION: RNA aptamer

<400> SEQUENCE: 23

gggagagagg aagagggaug ggaaaauagc cccagcgaga uaauacuugg cccccguacc    60

accauaaccc agaggucgau aguacuggau cccccc                             96

<210> SEQ ID NO 24
<211> LENGTH: 97
<212> TYPE: RNA
<213> ORGANISM: Artificial Sequence
<220> FEATURE:
<223> OTHER INFORMATION: RNA aptamer

<400> SEQUENCE: 24

gggagagagg aagagggaug ggccagaagg aacuaaacac cugaaccccc caucgcgaga    60

gaccauaacc cagaggucga uaguacugga ucccccc                            97

<210> SEQ ID NO 25
<211> LENGTH: 92
<212> TYPE: RNA
<213> ORGANISM: Artificial Sequence
<220> FEATURE:
<223> OTHER INFORMATION: RNA aptamer
<220> FEATURE:
<221> NAME/KEY: misc_feature
<222> LOCATION: (46)..(46)
<223> OTHER INFORMATION: "n" = c or a
```

-continued

<400> SEQUENCE: 25
gggagagagg aagagggaug ggaugucacu uggccccucg cgcacncgcc agcgagccca 60
uaacccagag gucgauagua cuggaucccc cc 92

<210> SEQ ID NO 26
<211> LENGTH: 97
<212> TYPE: RNA
<213> ORGANISM: Artificial Sequence
<220> FEATURE:
<223> OTHER INFORMATION: RNA aptamer

<400> SEQUENCE: 26
gggagagagg aagagggaug ggacacgccc agcgagcuca aacuuggccc ccgugcauca 60
ccccauaacc cagaggucga uaguacugga uccccc 97

<210> SEQ ID NO 27
<211> LENGTH: 97
<212> TYPE: RNA
<213> ORGANISM: Artificial Sequence
<220> FEATURE:
<223> OTHER INFORMATION: RNA aptamer

<400> SEQUENCE: 27
gggagagagg aagagggaug ggaagugcca cagcgagcac augacuuggc cccgcauugc 60
acccauaacc cagaggucga uaguacugga uccccc 97

<210> SEQ ID NO 28
<211> LENGTH: 95
<212> TYPE: RNA
<213> ORGANISM: Artificial Sequence
<220> FEATURE:
<223> OTHER INFORMATION: RNA aptamer

<400> SEQUENCE: 28
gggagagagg aagagggaug ggaaacuaau gcccuagcga gcauacccgg acuggccccg 60
ccauaaccca gaggucgaua guacuggauc ccccc 95

<210> SEQ ID NO 29
<211> LENGTH: 97
<212> TYPE: RNA
<213> ORGANISM: Artificial Sequence
<220> FEATURE:
<223> OTHER INFORMATION: RNA aptamer

<400> SEQUENCE: 29
gggagagagg aagagggaug ggaaaauagc cccagcgaga uaauacuugg ccccgcuacu 60
acccauaacc cagaggucga uaguacugga uccccc 97

<210> SEQ ID NO 30
<211> LENGTH: 95
<212> TYPE: RNA
<213> ORGANISM: Artificial Sequence
<220> FEATURE:
<223> OTHER INFORMATION: RNA aptamer

<400> SEQUENCE: 30
gggagagagg aagagggaug ggcgacccca cuggcggaaa ccgacaauca cuccccacga 60
ccauaaccca gaggucgaua guacuggauc ccccc 95

<210> SEQ ID NO 31

-continued

<211> LENGTH: 99
<212> TYPE: RNA
<213> ORGANISM: Artificial Sequence
<220> FEATURE:
<223> OTHER INFORMATION: RNA aptamer

<400> SEQUENCE: 31
gggagagagg aagagggaug ggcagcccag cgagggacac uuaacccccu gucccccauc 60
caaaccauaa cccagagguc gauaguacug gaucccccc 99

<210> SEQ ID NO 32
<211> LENGTH: 97
<212> TYPE: RNA
<213> ORGANISM: Artificial Sequence
<220> FEATURE:
<223> OTHER INFORMATION: RNA aptamer

<400> SEQUENCE: 32
gggagagagg aagagggaug ggccagaagu caccgcgacg guacugaacc ccccacccaa 60
acccauaacc cagaggucga uaguacugga uccccc 97

<210> SEQ ID NO 33
<211> LENGTH: 100
<212> TYPE: RNA
<213> ORGANISM: Artificial Sequence
<220> FEATURE:
<223> OTHER INFORMATION: RNA aptamer

<400> SEQUENCE: 33
gggagagagg aagagggaug ggccagaagu gcucacuaca acgcuuugac ccccccaucc 60
acaucccaua acccagaggu cgauaguacu ggauccccc 100

<210> SEQ ID NO 34
<211> LENGTH: 97
<212> TYPE: RNA
<213> ORGANISM: Artificial Sequence
<220> FEATURE:
<223> OTHER INFORMATION: RNA aptamer

<400> SEQUENCE: 34
gggagagagg aagagggaug ggccagcaac cgaagggcgg aauacccccc gucuccacau 60
acccauaacc cagaggucga uaguacugga uccccc 97

<210> SEQ ID NO 35
<211> LENGTH: 97
<212> TYPE: RNA
<213> ORGANISM: Artificial Sequence
<220> FEATURE:
<223> OTHER INFORMATION: RNA aptamer

<400> SEQUENCE: 35
gggagagagg aagagggaug ggacgcgacu caggcagcac uugacuuggc cccuugcgau 60
caccauaacc cagaggucga uaguacugga uccccc 97

<210> SEQ ID NO 36
<211> LENGTH: 97
<212> TYPE: RNA
<213> ORGANISM: Artificial Sequence
<220> FEATURE:
<223> OTHER INFORMATION: RNA aptamer

<400> SEQUENCE: 36
gggagagagg aagagggaug ggccagcaac gcuaacacgg aauacccccc accccaacgu 60

-continued gcccauaacc cagaggucga uaguacugga ucccccc 97

<210> SEQ ID NO 37
<211> LENGTH: 97
<212> TYPE: RNA
<213> ORGANISM: Artificial Sequence
<220> FEATURE:
<223> OTHER INFORMATION: RNA aptamer

<400> SEQUENCE: 37
gggagagagg aagagggaug ggcuucucaa ccgaaauaca acuuuaaauc auuuaucacu 60
uaccauaacc cagaggucga uaguacugga ucccccc 97

<210> SEQ ID NO 38
<211> LENGTH: 97
<212> TYPE: RNA
<213> ORGANISM: Artificial Sequence
<220> FEATURE:
<223> OTHER INFORMATION: RNA aptamer

<400> SEQUENCE: 38
gggagagagg aagagggaug ggauacgccg augcaagcau guccacacac cgcaugccgu 60
acccauaacc cagaggucga uaguacugga ucccccc 97

<210> SEQ ID NO 39
<211> LENGTH: 96
<212> TYPE: RNA
<213> ORGANISM: Artificial Sequence
<220> FEATURE:
<223> OTHER INFORMATION: RNA aptamer

<400> SEQUENCE: 39
gggagagagg aagagggaug gguacagagg aguacaagua gcauggucccc cucguguaaa 60 aacauaaccc agaggucgau aguacuggau cccccc 96

<210> SEQ ID NO 40
<211> LENGTH: 96
<212> TYPE: RNA
<213> ORGANISM: Artificial Sequence
<220> FEATURE:
<223> OTHER INFORMATION: RNA aptamer

<400> SEQUENCE: 40
gggagagagg aagagggaug ggugcaaaag agcuucuugu aguaugaucc cucaaccgca 60
agcauaaccc agaggucgau aguacuggau cccccc 96

<210> SEQ ID NO 41
<211> LENGTH: 96
<212> TYPE: RNA
<213> ORGANISM: Artificial Sequence
<220> FEATURE:
<223> OTHER INFORMATION: RNA aptamer

<400> SEQUENCE: 41
gggagagagg aagagggaug gguacagagg aguacaagua gcaugauccc cucguguaaa 60
aacauaaccc agaggucgau aguacuggau cccccc 96

<210> SEQ ID NO 42
<211> LENGTH: 96
<212> TYPE: RNA
<213> ORGANISM: Artificial Sequence
<220> FEATURE:

-continued

<223> OTHER INFORMATION: RNA aptamer

<400> SEQUENCE: 42
gggagagagg aagagggaug ggagccuaug uaacagaugc agaucccuag ucgucccaac 60
accauaaccc agaggucgau aguacuggau cccccc 96

<210> SEQ ID NO 43
<211> LENGTH: 96
<212> TYPE: RNA
<213> ORGANISM: Artificial Sequence
<220> FEATURE:
<223> OTHER INFORMATION: RNA aptamer

<400> SEQUENCE: 43
gggagagagg aagagggaug ggcacaacga acaccgcauc ccuugacaga aagagcacgc 60
cucauaaccc agaggucgau aguacuggau cccccc 96

<210> SEQ ID NO 44
<211> LENGTH: 96
<212> TYPE: RNA
<213> ORGANISM: Artificial Sequence
<220> FEATURE:
<223> OTHER INFORMATION: RNA aptamer

<400> SEQUENCE: 44
gggagagagg aagagggaug gguacagagg aguacaagua acaugauccc cucguguaaa 60
aacauaaccc agaggucgau aguacuggau cccccc 96

<210> SEQ ID NO 45
<211> LENGTH: 96
<212> TYPE: RNA
<213> ORGANISM: Artificial Sequence
<220> FEATURE:
<223> OTHER INFORMATION: RNA aptamer

<400> SEQUENCE: 45
gggagagagg aagagggaug ggcacaacga acaccgcauc ccuugacaga aagaacacgc 60
cucauaaccc agaggucgau aguacuggau cccccc 96

<210> SEQ ID NO 46
<211> LENGTH: 96
<212> TYPE: RNA
<213> ORGANISM: Artificial Sequence
<220> FEATURE:
<223> OTHER INFORMATION: RNA aptamer

<400> SEQUENCE: 46
gggagagagg aagagggaug ggcacaagga acaccgcauc ccuugacaga aagaacacgc 60
cucauaaccc agaggucgau aguacuggau cccccc 96

<210> SEQ ID NO 47
<211> LENGTH: 96
<212> TYPE: RNA
<213> ORGANISM: Artificial Sequence
<220> FEATURE:
<223> OTHER INFORMATION: RNA aptamer

<400> SEQUENCE: 47
gggagagagg aagagggaug ggagccuaug uaacagaugc agaucccuag acgacccaac 60
accauaaccc agaggucgau aguacuggau cccccc 96

-continued

<210> SEQ ID NO 48
<211> LENGTH: 22
<212> TYPE: RNA
<213> ORGANISM: Artificial Sequence
<220> FEATURE:
<223> OTHER INFORMATION: RNA aptamer

<400> SEQUENCE: 48
gggagagagg aagagggaug gg 22

<210> SEQ ID NO 49
<211> LENGTH: 34
<212> TYPE: RNA
<213> ORGANISM: Artificial Sequence
<220> FEATURE:
<223> OTHER INFORMATION: RNA aptamer

<400> SEQUENCE: 49
cauaacccag aggucgauag uacuggaucc cccc 34

<210> SEQ ID NO 50
<211> LENGTH: 40
<212> TYPE: RNA
<213> ORGANISM: Artificial Sequence
<220> FEATURE:
<223> OTHER INFORMATION: RNA aptamer

<400> SEQUENCE: 50
ugcgaacaaa gcugaaguac uuacgcacaa cccguagaau 40

<210> SEQ ID NO 51
<211> LENGTH: 37
<212> TYPE: RNA
<213> ORGANISM: Artificial Sequence
<220> FEATURE:
<223> OTHER INFORMATION: RNA aptamer

<400> SEQUENCE: 51
aacaacugaa gaacuacccu ucuuacugac gaauuaa 37

<210> SEQ ID NO 52
<211> LENGTH: 39
<212> TYPE: RNA
<213> ORGANISM: Artificial Sequence
<220> FEATURE:
<223> OTHER INFORMATION: RNA aptamer

<400> SEQUENCE: 52
aaacaaagcu gaaguacuua uuccaucacc acgccggaa 39

<210> SEQ ID NO 53
<211> LENGTH: 40
<212> TYPE: RNA
<213> ORGANISM: Artificial Sequence
<220> FEATURE:
<223> OTHER INFORMATION: RNA aptamer

<400> SEQUENCE: 53
uauuuggcuu cucagugccg cagagacagc aacaauuagu 40

<210> SEQ ID NO 54
<211> LENGTH: 40
<212> TYPE: RNA
<213> ORGANISM: Artificial Sequence
<220> FEATURE:
<223> OTHER INFORMATION: RNA aptamer -continued

<400> SEQUENCE: 54
acaaagcugg agaacuuacc guucccucuc cagagaucaa 40

<210> SEQ ID NO 55
<211> LENGTH: 40
<212> TYPE: RNA
<213> ORGANISM: Artificial Sequence
<220> FEATURE:
<223> OTHER INFORMATION: RNA aptamer

<400> SEQUENCE: 55
gaacaaagcu gaaguacuua cccaagauca ucccgaacga 40

<210> SEQ ID NO 56
<211> LENGTH: 40
<212> TYPE: RNA
<213> ORGANISM: Artificial Sequence
<220> FEATURE:
<223> OTHER INFORMATION: RNA aptamer

<400> SEQUENCE: 56
aacaaagcug gagaacuuaa cgucccucuc ccagcgguaa 40

<210> SEQ ID NO 57
<211> LENGTH: 25
<212> TYPE: RNA
<213> ORGANISM: Artificial Sequence
<220> FEATURE:
<223> OTHER INFORMATION: RNA aptamer

<400> SEQUENCE: 57
gggaacaaag cugaaguacu uaccc 25

<210> SEQ ID NO 58
<211> LENGTH: 25
<212> TYPE: RNA
<213> ORGANISM: Artificial Sequence
<220> FEATURE:
<223> OTHER INFORMATION: RNA aptamer

<400> SEQUENCE: 58
gggaacaaag cugaaguacu uaggg 25

<210> SEQ ID NO 59
<211> LENGTH: 25
<212> TYPE: RNA
<213> ORGANISM: Artificial Sequence
<220> FEATURE:
<223> OTHER INFORMATION: RNA aptamer

<400> SEQUENCE: 59
gggaacaaag cugaaguaca aaccc 25

<210> SEQ ID NO 60
<211> LENGTH: 25
<212> TYPE: RNA
<213> ORGANISM: Artificial Sequence
<220> FEATURE:
<223> OTHER INFORMATION: RNA aptamer

<400> SEQUENCE: 60
gggaacaaag cagaaguacu uaccc 25

<210> SEQ ID NO 61
<211> LENGTH: 25

-continued

<212> TYPE: RNA
<213> ORGANISM: Artificial Sequence
<220> FEATURE:
<223> OTHER INFORMATION: RNA aptamer

<400> SEQUENCE: 61
gggaacaaag cugaagaacu uaccc 25

<210> SEQ ID NO 62
<211> LENGTH: 22
<212> TYPE: RNA
<213> ORGANISM: Artificial Sequence
<220> FEATURE:
<223> OTHER INFORMATION: RNA aptamer

<400> SEQUENCE: 62
gggagagagg aagagggaug gg 22

<210> SEQ ID NO 63
<211> LENGTH: 34
<212> TYPE: RNA
<213> ORGANISM: Artificial Sequence
<220> FEATURE:
<223> OTHER INFORMATION: RNA aptamer

<400> SEQUENCE: 63
cauaacccag aggucgauag uacuggaucc cccc 34

<210> SEQ ID NO 64
<211> LENGTH: 40
<212> TYPE: RNA
<213> ORGANISM: Artificial Sequence
<220> FEATURE:
<223> OTHER INFORMATION: RNA aptamer

<400> SEQUENCE: 64
aauggaauca cugaaggccc uccguagcac cuaacacagu 40

<210> SEQ ID NO 65
<211> LENGTH: 40
<212> TYPE: RNA
<213> ORGANISM: Artificial Sequence
<220> FEATURE:
<223> OTHER INFORMATION: RNA aptamer

<400> SEQUENCE: 65
gcauccugcc agcggcgacg gaccuucgcc cacaggccuc 40

<210> SEQ ID NO 66
<211> LENGTH: 39
<212> TYPE: RNA
<213> ORGANISM: Artificial Sequence
<220> FEATURE:
<223> OTHER INFORMATION: RNA aptamer

<400> SEQUENCE: 66
uuauaagcac acugaagccc ucagcaaaac cuccacagg 39

<210> SEQ ID NO 67
<211> LENGTH: 40
<212> TYPE: RNA
<213> ORGANISM: Artificial Sequence
<220> FEATURE:
<223> OTHER INFORMATION: RNA aptamer

<400> SEQUENCE: 67

-continued

```
uaugaaauca cagaagcccg cguucgacac cuccacuguu                              40


<210> SEQ ID NO 68
<211> LENGTH: 48
<212> TYPE: RNA
<213> ORGANISM: Artificial Sequence
<220> FEATURE:
<223> OTHER INFORMATION: RNA aptamer

<400> SEQUENCE: 68

caaacucaca gacuccaacu gcaggagcac ccacccacac ugggacag                     48


<210> SEQ ID NO 69
<211> LENGTH: 40
<212> TYPE: RNA
<213> ORGANISM: Artificial Sequence
<220> FEATURE:
<223> OTHER INFORMATION: RNA aptamer

<400> SEQUENCE: 69

auccccgccg uaagccgucc ugauggacac cacacuccgc                              40


<210> SEQ ID NO 70
<211> LENGTH: 34
<212> TYPE: RNA
<213> ORGANISM: Artificial Sequence
<220> FEATURE:
<223> OTHER INFORMATION: RNA aptamer

<400> SEQUENCE: 70

auggggacua uaccgcguaa ugcugccucc ccau                                    34


<210> SEQ ID NO 71
<211> LENGTH: 29
<212> TYPE: RNA
<213> ORGANISM: Artificial Sequence
<220> FEATURE:
<223> OTHER INFORMATION: RNA aptamer

<400> SEQUENCE: 71

ggggacuaua ccggcaaucg ugcaucccc                                          29


<210> SEQ ID NO 72
<211> LENGTH: 6
<212> TYPE: PRT
<213> ORGANISM: Artificial Sequence
<220> FEATURE:
<223> OTHER INFORMATION: peptide ligand

<400> SEQUENCE: 72

Ser Phe Leu Leu Arg Asn
1               5


<210> SEQ ID NO 73
<211> LENGTH: 93
<212> TYPE: RNA
<213> ORGANISM: Artificial Sequence
<220> FEATURE:
<223> OTHER INFORMATION: RNA aptamer

<400> SEQUENCE: 73

gggagagagg aagagggaug ggaaaauagc cccagcgaga uaauacuugg ccccgcuacu        60

accauaaccc agaggucgau agyuacugga ucc                                     93


<210> SEQ ID NO 74
```

```
<211> LENGTH: 40
<212> TYPE: RNA
<213> ORGANISM: Artificial Sequence
<220> FEATURE:
<223> OTHER INFORMATION: RNA aptamer

<400> SEQUENCE: 74

aaaguaccga cuagguccca cuguuuaagc auccccgaac                              40

<210> SEQ ID NO 75
<211> LENGTH: 41
<212> TYPE: RNA
<213> ORGANISM: Artificial Sequence
<220> FEATURE:
<223> OTHER INFORMATION: RNA aptamer

<400> SEQUENCE: 75

aagcuccauc caagcgacga cacgcucguc ccgaaaagaa u                            41

<210> SEQ ID NO 76
<211> LENGTH: 41
<212> TYPE: RNA
<213> ORGANISM: Artificial Sequence
<220> FEATURE:
<223> OTHER INFORMATION: RNA aptamer

<400> SEQUENCE: 76

aagcuccguc caagcgacga cacguucguc ccgaaaagaa u                            41

<210> SEQ ID NO 77
<211> LENGTH: 40
<212> TYPE: RNA
<213> ORGANISM: Artificial Sequence
<220> FEATURE:
<223> OTHER INFORMATION: RNA aptamer

<400> SEQUENCE: 77

acaacgccac cuuccgcgcg acgccgcgcc gacgauaacu                              40

<210> SEQ ID NO 78
<211> LENGTH: 41
<212> TYPE: RNA
<213> ORGANISM: Artificial Sequence
<220> FEATURE:
<223> OTHER INFORMATION: RNA aptamer

<400> SEQUENCE: 78

acaacgccac cuuccgcgcg acgccgcgcc gacguauaac u                            41

<210> SEQ ID NO 79
<211> LENGTH: 40
<212> TYPE: RNA
<213> ORGANISM: Artificial Sequence
<220> FEATURE:
<223> OTHER INFORMATION: RNA aptamer

<400> SEQUENCE: 79

acgaaaauau cuccgucaag gaccuccugc cccaaacacu                              40

<210> SEQ ID NO 80
<211> LENGTH: 40
<212> TYPE: RNA
<213> ORGANISM: Artificial Sequence
<220> FEATURE:
<223> OTHER INFORMATION: RNA aptamer

<400> SEQUENCE: 80
```

-continued agacgacaca uccaagcgug agagaucacc cgacaagaau 40

<210> SEQ ID NO 81
<211> LENGTH: 42
<212> TYPE: RNA
<213> ORGANISM: Artificial Sequence
<220> FEATURE:
<223> OTHER INFORMATION: RNA aptamer

<400> SEQUENCE: 81
auuuuuucac acauucuuaa uuuucacuua cccgucccga uc 42

<210> SEQ ID NO 82
<211> LENGTH: 40
<212> TYPE: RNA
<213> ORGANISM: Artificial Sequence
<220> FEATURE:
<223> OTHER INFORMATION: RNA aptamer

<400> SEQUENCE: 82
caaagcaccc guccaagcga cagacauguc ccgcagcccu 40

<210> SEQ ID NO 83
<211> LENGTH: 40
<212> TYPE: RNA
<213> ORGANISM: Artificial Sequence
<220> FEATURE:
<223> OTHER INFORMATION: RNA aptamer

<400> SEQUENCE: 83
caccauuuau ucuucauuuu ucuucgccca guuccuccaa 40

<210> SEQ ID NO 84
<211> LENGTH: 39
<212> TYPE: RNA
<213> ORGANISM: Artificial Sequence
<220> FEATURE:
<223> OTHER INFORMATION: RNA aptamer

<400> SEQUENCE: 84
cauaagccgc cucagcugac aaagcccucc gcuuaggcc 39

<210> SEQ ID NO 85
<211> LENGTH: 40
<212> TYPE: RNA
<213> ORGANISM: Artificial Sequence
<220> FEATURE:
<223> OTHER INFORMATION: RNA aptamer

<400> SEQUENCE: 85
ccaaagugcu uccgcgaagu ucgaccauuc gccgccugca 40

<210> SEQ ID NO 86
<211> LENGTH: 40
<212> TYPE: RNA
<213> ORGANISM: Artificial Sequence
<220> FEATURE:
<223> OTHER INFORMATION: RNA aptamer

<400> SEQUENCE: 86
ccccuccgcc aacuuggccg ccucaggcac caucaccaac 40

<210> SEQ ID NO 87
<211> LENGTH: 41
<212> TYPE: RNA

<213> ORGANISM: Artificial Sequence
<220> FEATURE:
<223> OTHER INFORMATION: RNA aptamer

<400> SEQUENCE: 87
cccgaucucc ccgaggaccu ccacggcccg uccgccaguu u 41

<210> SEQ ID NO 88
<211> LENGTH: 40
<212> TYPE: RNA
<213> ORGANISM: Artificial Sequence
<220> FEATURE:
<223> OTHER INFORMATION: RNA aptamer

<400> SEQUENCE: 88
ccgccucagc aaucuagccc uccgcccgac ccuucccgcug 40

<210> SEQ ID NO 89
<211> LENGTH: 40
<212> TYPE: RNA
<213> ORGANISM: Artificial Sequence
<220> FEATURE:
<223> OTHER INFORMATION: RNA aptamer

<400> SEQUENCE: 89
ccgccucagc gagaucuucg cccuccgccc aagccucaac 40

<210> SEQ ID NO 90
<211> LENGTH: 40
<212> TYPE: RNA
<213> ORGANISM: Artificial Sequence
<220> FEATURE:
<223> OTHER INFORMATION: RNA aptamer

<400> SEQUENCE: 90
ccgccucagg acgacaccgg uccccuccgc ccguccgcgc 40

<210> SEQ ID NO 91
<211> LENGTH: 40
<212> TYPE: RNA
<213> ORGANISM: Artificial Sequence
<220> FEATURE:
<223> OTHER INFORMATION: RNA aptamer

<400> SEQUENCE: 91
ccgccucagg caucagcccc uccgcccgcc cacuucauca 40

<210> SEQ ID NO 92
<211> LENGTH: 40
<212> TYPE: RNA
<213> ORGANISM: Artificial Sequence
<220> FEATURE:
<223> OTHER INFORMATION: RNA aptamer

<400> SEQUENCE: 92
ccgccucagu uacuugauaa cccuccgccc gcccgcagcu 40

<210> SEQ ID NO 93
<211> LENGTH: 40
<212> TYPE: RNA
<213> ORGANISM: Artificial Sequence
<220> FEATURE:
<223> OTHER INFORMATION: RNA aptamer

<400> SEQUENCE: 93
cuuuacauau uacuuacuac auuuucauaa caccacacgc 40

-continued

<210> SEQ ID NO 94
<211> LENGTH: 40
<212> TYPE: RNA
<213> ORGANISM: Artificial Sequence
<220> FEATURE:
<223> OTHER INFORMATION: RNA aptamer

<400> SEQUENCE: 94
gacaccaucc aagcgaccaa ccaagguccc gcacauaacu 40

<210> SEQ ID NO 95
<211> LENGTH: 39
<212> TYPE: RNA
<213> ORGANISM: Artificial Sequence
<220> FEATURE:
<223> OTHER INFORMATION: RNA aptamer

<400> SEQUENCE: 95
gaugcaacuc gaaauggccg ccucgcguca gcguuccgc 39

<210> SEQ ID NO 96
<211> LENGTH: 39
<212> TYPE: RNA
<213> ORGANISM: Artificial Sequence
<220> FEATURE:
<223> OTHER INFORMATION: RNA aptamer

<400> SEQUENCE: 96
gcuuaucuua uaucacuuuu ucuucccaau ccuucaagu 39

<210> SEQ ID NO 97

<400> SEQUENCE: 97

000

<210> SEQ ID NO 98
<211> LENGTH: 40
<212> TYPE: RNA
<213> ORGANISM: Artificial Sequence
<220> FEATURE:
<223> OTHER INFORMATION: RNA aptamer

<400> SEQUENCE: 98
uaaccaacca agcguccaaa aaccuggacc cgccaagaau 40

<210> SEQ ID NO 99
<211> LENGTH: 40
<212> TYPE: RNA
<213> ORGANISM: Artificial Sequence
<220> FEATURE:
<223> OTHER INFORMATION: RNA aptamer

<400> SEQUENCE: 99
uaaccaacca agcguccaaa aaucuggacc cgccaagaau 40

<210> SEQ ID NO 100
<211> LENGTH: 40
<212> TYPE: RNA
<213> ORGANISM: Artificial Sequence
<220> FEATURE:
<223> OTHER INFORMATION: RNA aptamer

<400> SEQUENCE: 100
ucugacguuc caccguccuc gaaggcgacc agagcguuac 40

-continued

<210> SEQ ID NO 101
<211> LENGTH: 40
<212> TYPE: RNA
<213> ORGANISM: Artificial Sequence
<220> FEATURE:
<223> OTHER INFORMATION: RNA aptamer

<400> SEQUENCE: 101
ugccgccuca gccacacggc ccuccgcgcc cgccacaagc 40

<210> SEQ ID NO 102
<211> LENGTH: 22
<212> TYPE: RNA
<213> ORGANISM: Artificial Sequence
<220> FEATURE:
<223> OTHER INFORMATION: RNA aptamer

<400> SEQUENCE: 102
gggagagagg aagagggaug gg 22

<210> SEQ ID NO 103
<211> LENGTH: 18
<212> TYPE: RNA
<213> ORGANISM: Artificial Sequence
<220> FEATURE:
<223> OTHER INFORMATION: RNA aptamer

<400> SEQUENCE: 103
cauaacccag aggucgau 18

<210> SEQ ID NO 104
<211> LENGTH: 40
<212> TYPE: RNA
<213> ORGANISM: Artificial Sequence
<220> FEATURE:
<223> OTHER INFORMATION: RNA aptamer

<400> SEQUENCE: 104
agauuagccc cagcgagaua auacuuggcc ccgcuacuac 40

<210> SEQ ID NO 105
<211> LENGTH: 40
<212> TYPE: RNA
<213> ORGANISM: Artificial Sequence
<220> FEATURE:
<223> OTHER INFORMATION: RNA aptamer

<400> SEQUENCE: 105
uaaauagccc cagcgagauu cuacuuggcc ccgcuacuac 40

<210> SEQ ID NO 106
<211> LENGTH: 40
<212> TYPE: RNA
<213> ORGANISM: Artificial Sequence
<220> FEATURE:
<223> OTHER INFORMATION: RNA aptamer
<220> FEATURE:
<221> NAME/KEY: misc_feature
<222> LOCATION: (12)..(13)
<223> OTHER INFORMATION: "n" = g, c, u or a

<400> SEQUENCE: 106
aaaauacgcc anncgagauu auacuuggcc ccgcuaauac 40

<210> SEQ ID NO 107

-continued

<211> LENGTH: 40
<212> TYPE: RNA
<213> ORGANISM: Artificial Sequence
<220> FEATURE:
<223> OTHER INFORMATION: RNA aptamer

<400> SEQUENCE: 107
aaaauagccc cagcgagaua auacuuggcc ccgcuauuac 40

<210> SEQ ID NO 108
<211> LENGTH: 40
<212> TYPE: RNA
<213> ORGANISM: Artificial Sequence
<220> FEATURE:
<223> OTHER INFORMATION: RNA aptamer

<400> SEQUENCE: 108
aaaauagccc cagcgagaua auacuuggcc ccgcuagcac 40

<210> SEQ ID NO 109
<211> LENGTH: 40
<212> TYPE: RNA
<213> ORGANISM: Artificial Sequence
<220> FEATURE:
<223> OTHER INFORMATION: RNA aptamer

<400> SEQUENCE: 109
aaaauagccc cagcgagaua auacuuggcc ccgcuacaac 40

<210> SEQ ID NO 110
<211> LENGTH: 40
<212> TYPE: RNA
<213> ORGANISM: Artificial Sequence
<220> FEATURE:
<223> OTHER INFORMATION: RNA aptamer

<400> SEQUENCE: 110
agaauggccc cagcgagauu auacuuggcc ccgccaauac 40

<210> SEQ ID NO 111
<211> LENGTH: 40
<212> TYPE: RNA
<213> ORGANISM: Artificial Sequence
<220> FEATURE:
<223> OTHER INFORMATION: RNA aptamer

<400> SEQUENCE: 111
aaaauagccc cagcgagaug auacuuggcc ccgcuaauac 40

<210> SEQ ID NO 112
<211> LENGTH: 40
<212> TYPE: RNA
<213> ORGANISM: Artificial Sequence
<220> FEATURE:
<223> OTHER INFORMATION: RNA aptamer

<400> SEQUENCE: 112
agaauacgcc uagcgagaag auacuuggcc cccgugcaac 40

<210> SEQ ID NO 113
<211> LENGTH: 40
<212> TYPE: RNA
<213> ORGANISM: Artificial Sequence
<220> FEATURE:
<223> OTHER INFORMATION: RNA aptamer

<400> SEQUENCE: 113

-continued aaaauagccc cagcgagaua auacuuggcc ccgcuguuac 40

<210> SEQ ID NO 114
<211> LENGTH: 40
<212> TYPE: RNA
<213> ORGANISM: Artificial Sequence
<220> FEATURE:
<223> OTHER INFORMATION: RNA aptamer

<400> SEQUENCE: 114
aaauuugccc cagcgagaua auacuuggcc ccgcaacuac 40

<210> SEQ ID NO 115
<211> LENGTH: 40
<212> TYPE: RNA
<213> ORGANISM: Artificial Sequence
<220> FEATURE:
<223> OTHER INFORMATION: RNA aptamer

<400> SEQUENCE: 115
auaauagccc cagcgagaua auacuuggcc ccgcuacuaa 40

<210> SEQ ID NO 116
<211> LENGTH: 40
<212> TYPE: RNA
<213> ORGANISM: Artificial Sequence
<220> FEATURE:
<223> OTHER INFORMATION: RNA aptamer

<400> SEQUENCE: 116
agaauagccc cagcgagaua auacuuggcc ccgcuaauac 40

<210> SEQ ID NO 117
<211> LENGTH: 41
<212> TYPE: RNA
<213> ORGANISM: Artificial Sequence
<220> FEATURE:
<223> OTHER INFORMATION: RNA aptamer

<400> SEQUENCE: 117
aaauuugccc uagcgagauu auacuuggcc ccgcgaaaaa c 41

<210> SEQ ID NO 118
<211> LENGTH: 40
<212> TYPE: RNA
<213> ORGANISM: Artificial Sequence
<220> FEATURE:
<223> OTHER INFORMATION: RNA aptamer

<400> SEQUENCE: 118
aaaauagccc cagcgagaua auacuuggcc ccgcgaacac 40

<210> SEQ ID NO 119
<211> LENGTH: 40
<212> TYPE: RNA
<213> ORGANISM: Artificial Sequence
<220> FEATURE:
<223> OTHER INFORMATION: RNA aptamer

<400> SEQUENCE: 119
ugcauagccc cagcgagaua auacuuggcc ccgcuacaac 40

<210> SEQ ID NO 120
<211> LENGTH: 40
<212> TYPE: RNA

-continued

<213> ORGANISM: Artificial Sequence
<220> FEATURE:
<223> OTHER INFORMATION: RNA aptamer
<220> FEATURE:
<221> NAME/KEY: misc_feature
<222> LOCATION: (1)..(40)
<223> OTHER INFORMATION: "n" = g, c, u or a

<400> SEQUENCE: 120
ngauuagccc nagcgagaua nuacuuggcc ccgcuacnuc 40

<210> SEQ ID NO 121
<211> LENGTH: 40
<212> TYPE: RNA
<213> ORGANISM: Artificial Sequence
<220> FEATURE:
<223> OTHER INFORMATION: RNA aptamer

<400> SEQUENCE: 121
aaaauaacca cagcgagauc auacuuggcc ccguuacuac 40

<210> SEQ ID NO 122
<211> LENGTH: 40
<212> TYPE: RNA
<213> ORGANISM: Artificial Sequence
<220> FEATURE:
<223> OTHER INFORMATION: RNA aptamer

<400> SEQUENCE: 122
aaaauagccc uagcgagaua auacuuggcc ccgccacaua 40

<210> SEQ ID NO 123
<211> LENGTH: 40
<212> TYPE: RNA
<213> ORGANISM: Artificial Sequence
<220> FEATURE:
<223> OTHER INFORMATION: RNA aptamer

<400> SEQUENCE: 123
cagauagcca cagcgagauc auacuuggcc ccgcuacuac 40

<210> SEQ ID NO 124
<211> LENGTH: 40
<212> TYPE: RNA
<213> ORGANISM: Artificial Sequence
<220> FEATURE:
<223> OTHER INFORMATION: RNA aptamer

<400> SEQUENCE: 124
agaauagccc cagcgagaua auccuuggcc ccgcuacugc 40

<210> SEQ ID NO 125
<211> LENGTH: 40
<212> TYPE: RNA
<213> ORGANISM: Artificial Sequence
<220> FEATURE:
<223> OTHER INFORMATION: RNA aptamer
<220> FEATURE:
<221> NAME/KEY: misc_feature
<222> LOCATION: (1)..(40)
<223> OTHER INFORMATION: "n" = g, c, u or a

<400> SEQUENCE: 125
aancuagccc nagcgagaua uuacuuggcc ccgcnacuac 40

<210> SEQ ID NO 126
<211> LENGTH: 40

-continued

<212> TYPE: RNA
<213> ORGANISM: Artificial Sequence
<220> FEATURE:
<223> OTHER INFORMATION: RNA aptamer

<400> SEQUENCE: 126
aaacuagccu cagcgagaua auacuuggcc ccgcuacuac 40

<210> SEQ ID NO 127
<211> LENGTH: 40
<212> TYPE: RNA
<213> ORGANISM: Artificial Sequence
<220> FEATURE:
<223> OTHER INFORMATION: RNA aptamer

<400> SEQUENCE: 127
ccagaagcgc ucacuacaac guugaacccc ccguccacac 40

<210> SEQ ID NO 128
<211> LENGTH: 40
<212> TYPE: RNA
<213> ORGANISM: Artificial Sequence
<220> FEATURE:
<223> OTHER INFORMATION: RNA aptamer

<400> SEQUENCE: 128
ccaaaagcgg acugaagacg uguuuccccc aucuccguga 40

<210> SEQ ID NO 129
<211> LENGTH: 40
<212> TYPE: RNA
<213> ORGANISM: Artificial Sequence
<220> FEATURE:
<223> OTHER INFORMATION: RNA aptamer

<400> SEQUENCE: 129
ccagaaggaa cuaaacaccu gaacccccca ucgcgagaga 40

<210> SEQ ID NO 130
<211> LENGTH: 40
<212> TYPE: RNA
<213> ORGANISM: Artificial Sequence
<220> FEATURE:
<223> OTHER INFORMATION: RNA aptamer

<400> SEQUENCE: 130
ccagcaacgu cacacgaacg gaauaccccc cauugaaaac 40

<210> SEQ ID NO 131
<211> LENGTH: 40
<212> TYPE: RNA
<213> ORGANISM: Artificial Sequence
<220> FEATURE:
<223> OTHER INFORMATION: RNA aptamer

<400> SEQUENCE: 131
ucuuagauau agaacuccga gaggacugac cguacagaac 40

<210> SEQ ID NO 132
<211> LENGTH: 40
<212> TYPE: RNA
<213> ORGANISM: Artificial Sequence
<220> FEATURE:
<223> OTHER INFORMATION: RNA aptamer

<400> SEQUENCE: 132

-continued

```
agaauagccc cagcgagauc guacuuggcc ccgcuaguac                        40


<210> SEQ ID NO 133
<211> LENGTH: 40
<212> TYPE: RNA
<213> ORGANISM: Artificial Sequence
<220> FEATURE:
<223> OTHER INFORMATION: RNA aptamer

<400> SEQUENCE: 133

ccaaaagcgc auacaccugc guguuucccc cgccaacagu                        40


<210> SEQ ID NO 134
<211> LENGTH: 42
<212> TYPE: RNA
<213> ORGANISM: Artificial Sequence
<220> FEATURE:
<223> OTHER INFORMATION: RNA aptamer
<220> FEATURE:
<221> NAME/KEY: misc_feature
<222> LOCATION: (1)..(42)
<223> OTHER INFORMATION: "n" = g, c, u or a

<400> SEQUENCE: 134

ccauugcunc ccugaacang ggcnccacnc cgccuncaca gu                     42


<210> SEQ ID NO 135
<211> LENGTH: 40
<212> TYPE: RNA
<213> ORGANISM: Artificial Sequence
<220> FEATURE:
<223> OTHER INFORMATION: RNA aptamer

<400> SEQUENCE: 135

ccagaacacc agugaacccc ccagccccuu cucaccagau                        40


<210> SEQ ID NO 136
<211> LENGTH: 43
<212> TYPE: RNA
<213> ORGANISM: Artificial Sequence
<220> FEATURE:
<223> OTHER INFORMATION: RNA aptamer

<400> SEQUENCE: 136

ccagaagcga cacuaacgcu gaacccccca gucccuucac gug                    43


<210> SEQ ID NO 137
<211> LENGTH: 39
<212> TYPE: RNA
<213> ORGANISM: Artificial Sequence
<220> FEATURE:
<223> OTHER INFORMATION: RNA aptamer

<400> SEQUENCE: 137

auaccgagca cgcaaaacac acaaugccca agcaggacu                         39


<210> SEQ ID NO 138
<211> LENGTH: 38
<212> TYPE: RNA
<213> ORGANISM: Artificial Sequence
<220> FEATURE:
<223> OTHER INFORMATION: RNA aptamer

<400> SEQUENCE: 138

agcccgagaa aauaacgcgu uccaccauac uacuaagc                          38
```

-continued

<210> SEQ ID NO 139
<211> LENGTH: 40
<212> TYPE: RNA
<213> ORGANISM: Artificial Sequence
<220> FEATURE:
<223> OTHER INFORMATION: RNA aptamer

<400> SEQUENCE: 139
uaaauagccc cagcgagaua auacuuggcc ccgcaacuac 40

<210> SEQ ID NO 140
<211> LENGTH: 43
<212> TYPE: RNA
<213> ORGANISM: Artificial Sequence
<220> FEATURE:
<223> OTHER INFORMATION: RNA aptamer
<220> FEATURE:
<221> NAME/KEY: misc_feature
<222> LOCATION: (1)..(43)
<223> OTHER INFORMATION: "n" = g, c, u or a

<400> SEQUENCE: 140
aguccgacug gagaacangu acucuauaag cacuuncaun can 43

<210> SEQ ID NO 141
<211> LENGTH: 40
<212> TYPE: RNA
<213> ORGANISM: Artificial Sequence
<220> FEATURE:
<223> OTHER INFORMATION: RNA aptamer

<400> SEQUENCE: 141
cucggcagaa gacacgcauu caccuggugc caccucguaa 40

<210> SEQ ID NO 142
<211> LENGTH: 39
<212> TYPE: RNA
<213> ORGANISM: Artificial Sequence
<220> FEATURE:
<223> OTHER INFORMATION: RNA aptamer

<400> SEQUENCE: 142
gccgucgcca ggaaucaaac ugcuacucca ucccgggca 39

<210> SEQ ID NO 143
<211> LENGTH: 40
<212> TYPE: RNA
<213> ORGANISM: Artificial Sequence
<220> FEATURE:
<223> OTHER INFORMATION: RNA aptamer

<400> SEQUENCE: 143
ccagaagcua aacacucaua accacgcuga accccccaac 40

<210> SEQ ID NO 144
<211> LENGTH: 40
<212> TYPE: RNA
<213> ORGANISM: Artificial Sequence
<220> FEATURE:
<223> OTHER INFORMATION: RNA aptamer

<400> SEQUENCE: 144
ccagaaccaa cugcggugaa ccccccauac cgcgacacau 40

<210> SEQ ID NO 145
<211> LENGTH: 40
<212> TYPE: RNA

-continued

<213> ORGANISM: Artificial Sequence
<220> FEATURE:
<223> OTHER INFORMATION: RNA aptamer

<400> SEQUENCE: 145
aacuuagccu cagcgagaua acgcuuggcc ccgcuaagac 40

<210> SEQ ID NO 146
<211> LENGTH: 40
<212> TYPE: RNA
<213> ORGANISM: Artificial Sequence
<220> FEATURE:
<223> OTHER INFORMATION: RNA aptamer

<400> SEQUENCE: 146
uaaguugccc cagcgagaua guacuuggcc ccgcuacuaa 40

<210> SEQ ID NO 147
<211> LENGTH: 40
<212> TYPE: RNA
<213> ORGANISM: Artificial Sequence
<220> FEATURE:
<223> OTHER INFORMATION: RNA aptamer

<400> SEQUENCE: 147
aaaauagccc cagcgagaua auacuuggcc ccgcuacuaa 40

<210> SEQ ID NO 148
<211> LENGTH: 36
<212> TYPE: RNA
<213> ORGANISM: Artificial Sequence
<220> FEATURE:
<223> OTHER INFORMATION: RNA aptamer

<400> SEQUENCE: 148
gagagcccca gcgagauaau acuuggcccc gcucuu 36

<210> SEQ ID NO 149
<211> LENGTH: 22
<212> TYPE: RNA
<213> ORGANISM: Artificial Sequence
<220> FEATURE:
<223> OTHER INFORMATION: RNA aptamer

<400> SEQUENCE: 149
gggagagagg aagagggaug gg 22

<210> SEQ ID NO 150
<211> LENGTH: 34
<212> TYPE: RNA
<213> ORGANISM: Artificial Sequence
<220> FEATURE:
<223> OTHER INFORMATION: RNA aptamer

<400> SEQUENCE: 150
cauaacccag aggucgauag uacuggaucc cccc 34

<210> SEQ ID NO 151
<211> LENGTH: 40
<212> TYPE: RNA
<213> ORGANISM: Artificial Sequence
<220> FEATURE:
<223> OTHER INFORMATION: RNA aptamer

<400> SEQUENCE: 151
acucgaacau uuccacuaac caaccauacu aaagcaccgc 40

-continued

<210> SEQ ID NO 152
<211> LENGTH: 40
<212> TYPE: RNA
<213> ORGANISM: Artificial Sequence
<220> FEATURE:
<223> OTHER INFORMATION: RNA aptamer

<400> SEQUENCE: 152
acucgaacau uuccacuaac caaccauacu aaagcaccgc 40

<210> SEQ ID NO 153
<211> LENGTH: 39
<212> TYPE: RNA
<213> ORGANISM: Artificial Sequence
<220> FEATURE:
<223> OTHER INFORMATION: RNA aptamer

<400> SEQUENCE: 153
gaccaccaac acaccacaua cugcuuugua ccaacauuc 39

<210> SEQ ID NO 154
<211> LENGTH: 40
<212> TYPE: RNA
<213> ORGANISM: Artificial Sequence
<220> FEATURE:
<223> OTHER INFORMATION: RNA aptamer

<400> SEQUENCE: 154
cccagcgaac acacaacaga acacgaacgg auccgagcaa 40

<210> SEQ ID NO 155
<211> LENGTH: 39
<212> TYPE: RNA
<213> ORGANISM: Artificial Sequence
<220> FEATURE:
<223> OTHER INFORMATION: RNA aptamer

<400> SEQUENCE: 155
gucacaaacu accuucaucc uucgcuugau acaacauuc 39

<210> SEQ ID NO 156
<211> LENGTH: 40
<212> TYPE: RNA
<213> ORGANISM: Artificial Sequence
<220> FEATURE:
<223> OTHER INFORMATION: RNA aptamer

<400> SEQUENCE: 156
acaccaagga cccaacgacc cucgcuugac acagucauuc 40

<210> SEQ ID NO 157
<211> LENGTH: 37
<212> TYPE: RNA
<213> ORGANISM: Artificial Sequence
<220> FEATURE:
<223> OTHER INFORMATION: RNA aptamer

<400> SEQUENCE: 157
augaacaaca cccaaacuug cuucaaccgc auccaca 37

<210> SEQ ID NO 158
<211> LENGTH: 40
<212> TYPE: RNA
<213> ORGANISM: Artificial Sequence
<220> FEATURE:

-continued

<223> OTHER INFORMATION: RNA aptamer

<400> SEQUENCE: 158
gaccucacgc acugcuaagc ggcucugaug gagcucuaug 40

<210> SEQ ID NO 159
<211> LENGTH: 41
<212> TYPE: RNA
<213> ORGANISM: Artificial Sequence
<220> FEATURE:
<223> OTHER INFORMATION: RNA aptamer

<400> SEQUENCE: 159
ccaccuccga aaaaucacaa ucugcccuug acaccagcua g 41

<210> SEQ ID NO 160
<211> LENGTH: 40
<212> TYPE: RNA
<213> ORGANISM: Artificial Sequence
<220> FEATURE:
<223> OTHER INFORMATION: RNA aptamer

<400> SEQUENCE: 160
ccucauuggc ccugccacgc ucggacaacc guuccgcuca 40

<210> SEQ ID NO 161
<211> LENGTH: 40
<212> TYPE: RNA
<213> ORGANISM: Artificial Sequence
<220> FEATURE:
<223> OTHER INFORMATION: RNA aptamer

<400> SEQUENCE: 161
uccagugcag uuccauaacc gcuacucagc gcgugauuag 40

<210> SEQ ID NO 162
<211> LENGTH: 40
<212> TYPE: RNA
<213> ORGANISM: Artificial Sequence
<220> FEATURE:
<223> OTHER INFORMATION: RNA aptamer

<400> SEQUENCE: 162
uuucgagcaa ccucccaaca aucuaaccgu aacccuccag 40

<210> SEQ ID NO 163
<211> LENGTH: 40
<212> TYPE: RNA
<213> ORGANISM: Artificial Sequence
<220> FEATURE:
<223> OTHER INFORMATION: RNA aptamer

<400> SEQUENCE: 163
caacaucagc acgccugaac cuucgcuugc aacagcauuc 40

<210> SEQ ID NO 164
<211> LENGTH: 41
<212> TYPE: RNA
<213> ORGANISM: Artificial Sequence
<220> FEATURE:
<223> OTHER INFORMATION: RNA aptamer

<400> SEQUENCE: 164
ccaccuccga aaaaucacaa ucugcccuug acaccagcua g 41

-continued

<210> SEQ ID NO 165
<211> LENGTH: 40
<212> TYPE: RNA
<213> ORGANISM: Artificial Sequence
<220> FEATURE:
<223> OTHER INFORMATION: RNA aptamer

<400> SEQUENCE: 165
uuacaccauc gaccaaacua ugcgccguac cacuauacga 40

<210> SEQ ID NO 166
<211> LENGTH: 15
<212> TYPE: RNA
<213> ORGANISM: Artificial Sequence
<220> FEATURE:
<223> OTHER INFORMATION: RNA aptamer

<400> SEQUENCE: 166
gggaggacga ugcgg 15

<210> SEQ ID NO 167
<211> LENGTH: 25
<212> TYPE: RNA
<213> ORGANISM: Artificial Sequence
<220> FEATURE:
<223> OTHER INFORMATION: RNA aptamer

<400> SEQUENCE: 167
cagacgacuc gcugaggauc cgaga 25

<210> SEQ ID NO 168
<211> LENGTH: 40
<212> TYPE: RNA
<213> ORGANISM: Artificial Sequence
<220> FEATURE:
<223> OTHER INFORMATION: RNA aptamer

<400> SEQUENCE: 168
acuagccuca ucagcucaug ugccccuccg ccuggaucac 40

<210> SEQ ID NO 169
<211> LENGTH: 41
<212> TYPE: RNA
<213> ORGANISM: Artificial Sequence
<220> FEATURE:
<223> OTHER INFORMATION: RNA aptamer

<400> SEQUENCE: 169
ugaccaagcc ucacguugaa ccugccagua gaccccgccc a 41

<210> SEQ ID NO 170
<211> LENGTH: 40
<212> TYPE: RNA
<213> ORGANISM: Artificial Sequence
<220> FEATURE:
<223> OTHER INFORMATION: RNA aptamer

<400> SEQUENCE: 170
uuaaccauca gcucauggcc ccugcccucu caaggaccac 40

<210> SEQ ID NO 171
<211> LENGTH: 40
<212> TYPE: RNA
<213> ORGANISM: Artificial Sequence
<220> FEATURE:
<223> OTHER INFORMATION: RNA aptamer -continued

<400> SEQUENCE: 171
caccagaccg acaucagcuu auggccccuc acccacaccg 40

<210> SEQ ID NO 172
<211> LENGTH: 39
<212> TYPE: RNA
<213> ORGANISM: Artificial Sequence
<220> FEATURE:
<223> OTHER INFORMATION: RNA aptamer

<400> SEQUENCE: 172
ggagcgcaau ucgccucgca aguugaacuc cgcuggcgg 39

<210> SEQ ID NO 173
<211> LENGTH: 40
<212> TYPE: RNA
<213> ORGANISM: Artificial Sequence
<220> FEATURE:
<223> OTHER INFORMATION: RNA aptamer

<400> SEQUENCE: 173
uaagcucuuu ggcuuagccc gacacguuga acuccagagu 40

<210> SEQ ID NO 174
<211> LENGTH: 40
<212> TYPE: RNA
<213> ORGANISM: Artificial Sequence
<220> FEATURE:
<223> OTHER INFORMATION: RNA aptamer

<400> SEQUENCE: 174
cacgguacca ccaagucaca cguugaacuc caugcagcug 40

<210> SEQ ID NO 175
<211> LENGTH: 40
<212> TYPE: RNA
<213> ORGANISM: Artificial Sequence
<220> FEATURE:
<223> OTHER INFORMATION: RNA aptamer

<400> SEQUENCE: 175
ccaccgaucg caucagcuca uggccccucc cgacccgcca 40

<210> SEQ ID NO 176
<211> LENGTH: 41
<212> TYPE: RNA
<213> ORGANISM: Artificial Sequence
<220> FEATURE:
<223> OTHER INFORMATION: RNA aptamer

<400> SEQUENCE: 176
ccagacguuc ucgccccgcc gaucaucagc gcuggcccua u 41

<210> SEQ ID NO 177
<211> LENGTH: 40
<212> TYPE: RNA
<213> ORGANISM: Artificial Sequence
<220> FEATURE:
<223> OTHER INFORMATION: RNA aptamer

<400> SEQUENCE: 177
cacuaccacg ccauaucagc uaauggcccc ucccuacgca 40

<210> SEQ ID NO 178
<211> LENGTH: 40

-continued

<212> TYPE: RNA
<213> ORGANISM: Artificial Sequence
<220> FEATURE:
<223> OTHER INFORMATION: RNA aptamer

<400> SEQUENCE: 178
cacucagcgc ccugcgaaac guugccgccu cccaacgucu 40

<210> SEQ ID NO 179
<211> LENGTH: 40
<212> TYPE: RNA
<213> ORGANISM: Artificial Sequence
<220> FEATURE:
<223> OTHER INFORMATION: RNA aptamer

<400> SEQUENCE: 179
acucaccagu caccaucagc ucaugcgccc cuccccccgac 40

<210> SEQ ID NO 180
<211> LENGTH: 40
<212> TYPE: RNA
<213> ORGANISM: Artificial Sequence
<220> FEATURE:
<223> OTHER INFORMATION: RNA aptamer

<400> SEQUENCE: 180
cucuuuuugu ccccgcacgu ugaacuccug ucccucuacu 40

<210> SEQ ID NO 181
<211> LENGTH: 39
<212> TYPE: RNA
<213> ORGANISM: Artificial Sequence
<220> FEATURE:
<223> OTHER INFORMATION: RNA aptamer

<400> SEQUENCE: 181
ugacgguucu ucucucgccu cuggagcucu cgucucgau 39

<210> SEQ ID NO 182
<211> LENGTH: 40
<212> TYPE: RNA
<213> ORGANISM: Artificial Sequence
<220> FEATURE:
<223> OTHER INFORMATION: RNA aptamer

<400> SEQUENCE: 182
cacuuuagcu cacgccaccg cacguugaac gcccaucccg 40

<210> SEQ ID NO 183
<211> LENGTH: 40
<212> TYPE: RNA
<213> ORGANISM: Artificial Sequence
<220> FEATURE:
<223> OTHER INFORMATION: RNA aptamer

<400> SEQUENCE: 183
caaugcagca ucagcucaug gccccuccac aagcgcgaau 40

<210> SEQ ID NO 184
<211> LENGTH: 40
<212> TYPE: RNA
<213> ORGANISM: Artificial Sequence
<220> FEATURE:
<223> OTHER INFORMATION: RNA aptamer

<400> SEQUENCE: 184

-continued caugucuaca acaaucucgc ccguugaguc ucgucgaauu 40

<210> SEQ ID NO 185
<211> LENGTH: 40
<212> TYPE: RNA
<213> ORGANISM: Artificial Sequence
<220> FEATURE:
<223> OTHER INFORMATION: RNA aptamer

<400> SEQUENCE: 185
cgaucuuuuc gucaaccgca cguugaacuc ggcucggcac 40

<210> SEQ ID NO 186
<211> LENGTH: 39
<212> TYPE: RNA
<213> ORGANISM: Artificial Sequence
<220> FEATURE:
<223> OTHER INFORMATION: RNA aptamer

<400> SEQUENCE: 186
cacccguccg uccaaauccg cuucguugga ccccaucuu 39

<210> SEQ ID NO 187
<211> LENGTH: 41
<212> TYPE: RNA
<213> ORGANISM: Artificial Sequence
<220> FEATURE:
<223> OTHER INFORMATION: RNA aptamer

<400> SEQUENCE: 187
gaggacgaug cggacuagcc ucaucagcuc augugccccu c 41

<210> SEQ ID NO 188
<211> LENGTH: 49
<212> TYPE: RNA
<213> ORGANISM: Artificial Sequence
<220> FEATURE:
<223> OTHER INFORMATION: RNA aptamer

<400> SEQUENCE: 188
gggggaauuc uaauacgacu cacuauaggg agagaggaag agggaugggg 49

<210> SEQ ID NO 189
<211> LENGTH: 40
<212> TYPE: RNA
<213> ORGANISM: Artificial Sequence
<220> FEATURE:
<223> OTHER INFORMATION: RNA aptamer

<400> SEQUENCE: 189
gcugccgcgc cuggacccca cccacauaug ggccacacac 40

<210> SEQ ID NO 190
<211> LENGTH: 40
<212> TYPE: RNA
<213> ORGANISM: Artificial Sequence
<220> FEATURE:
<223> OTHER INFORMATION: RNA aptamer

<400> SEQUENCE: 190
aaugacaauu gacucggaaa cccucauguu ccaacaccgg 40

<210> SEQ ID NO 191
<211> LENGTH: 40
<212> TYPE: RNA
<213> ORGANISM: Artificial Sequence -continued
<220> FEATURE:
<223> OTHER INFORMATION: RNA aptamer

<400> SEQUENCE: 191
ccuacucucc acaccugguu uuaugcucua cacaccucac 40

<210> SEQ ID NO 192
<211> LENGTH: 40
<212> TYPE: RNA
<213> ORGANISM: Artificial Sequence
<220> FEATURE:
<223> OTHER INFORMATION: RNA aptamer

<400> SEQUENCE: 192
cugccccgac cacaaaggac ggaacccuac ccacaguggg 40

<210> SEQ ID NO 193
<211> LENGTH: 40
<212> TYPE: RNA
<213> ORGANISM: Artificial Sequence
<220> FEATURE:
<223> OTHER INFORMATION: RNA aptamer

<400> SEQUENCE: 193
cauaaaagca auuugccacc ggcguacggc accccaauau 40

<210> SEQ ID NO 194
<211> LENGTH: 40
<212> TYPE: RNA
<213> ORGANISM: Artificial Sequence
<220> FEATURE:
<223> OTHER INFORMATION: RNA aptamer

<400> SEQUENCE: 194
caccuaugcc aucaggccuc aaucuccggc agcgacucua 40

<210> SEQ ID NO 195
<211> LENGTH: 39
<212> TYPE: RNA
<213> ORGANISM: Artificial Sequence
<220> FEATURE:
<223> OTHER INFORMATION: RNA aptamer

<400> SEQUENCE: 195
aucaaccaca ggaagagugc agccauagca cacagacca 39

<210> SEQ ID NO 196
<211> LENGTH: 40
<212> TYPE: RNA
<213> ORGANISM: Artificial Sequence
<220> FEATURE:
<223> OTHER INFORMATION: RNA aptamer

<400> SEQUENCE: 196
gcgacauacc ccacccacac uggcacaacg cgcaaugccg 40

<210> SEQ ID NO 197
<211> LENGTH: 38
<212> TYPE: RNA
<213> ORGANISM: Artificial Sequence
<220> FEATURE:
<223> OTHER INFORMATION: RNA aptamer

<400> SEQUENCE: 197
cuucaaaggu ccuguaucca gccaccccac ugacagga 38

-continued

<210> SEQ ID NO 198
<211> LENGTH: 32
<212> TYPE: RNA
<213> ORGANISM: Artificial Sequence
<220> FEATURE:
<223> OTHER INFORMATION: Oligonucleotide

<400> SEQUENCE: 198
cuacccagca aggucaaccc uacccacacu gg 32

<210> SEQ ID NO 199
<211> LENGTH: 40
<212> TYPE: RNA
<213> ORGANISM: Artificial Sequence
<220> FEATURE:
<223> OTHER INFORMATION: Oligonucleotide

<400> SEQUENCE: 199
aucuuaaaga ucaccggcgu ucggcaacac ccgacccaaa 40

<210> SEQ ID NO 200
<211> LENGTH: 40
<212> TYPE: RNA
<213> ORGANISM: Artificial Sequence
<220> FEATURE:
<223> OTHER INFORMATION: Oligonucleotide

<400> SEQUENCE: 200
gcacuaaacu ucgauuaccc cccacccaca cuggcugcac 40

<210> SEQ ID NO 201
<211> LENGTH: 40
<212> TYPE: RNA
<213> ORGANISM: Artificial Sequence
<220> FEATURE:
<223> OTHER INFORMATION: Oligonucleotide

<400> SEQUENCE: 201
cagauuaccc uacccacacu gcgugcggac aaccauuggc 40

<210> SEQ ID NO 202
<211> LENGTH: 39
<212> TYPE: RNA
<213> ORGANISM: Artificial Sequence
<220> FEATURE:
<223> OTHER INFORMATION: Oligonucleotide

<400> SEQUENCE: 202
gcacaaauga gaacacgagu ucaccccgcc cacacugga 39

<210> SEQ ID NO 203
<211> LENGTH: 40
<212> TYPE: RNA
<213> ORGANISM: Artificial Sequence
<220> FEATURE:
<223> OTHER INFORMATION: Oligonucleotide

<400> SEQUENCE: 203
gcgcagauca acccuaccca uacugggcuc cuugugaagg 40

<210> SEQ ID NO 204
<211> LENGTH: 41
<212> TYPE: RNA
<213> ORGANISM: Artificial Sequence
<220> FEATURE:
<223> OTHER INFORMATION: Oligonucleotide

<400> SEQUENCE: 204
caagcgcuga aaccaaugca ccccacccca cacuggugua c    41

<210> SEQ ID NO 205
<211> LENGTH: 40
<212> TYPE: RNA
<213> ORGANISM: Artificial Sequence
<220> FEATURE:
<223> OTHER INFORMATION: Oligonucleotide

<400> SEQUENCE: 205
augugaaaca cagaagcccu guacagaccg ccgacuguca    40

<210> SEQ ID NO 206
<211> LENGTH: 40
<212> TYPE: RNA
<213> ORGANISM: Artificial Sequence
<220> FEATURE:
<223> OTHER INFORMATION: Oligonucleotide

<400> SEQUENCE: 206
caaacucaca gacaccaacu gcaggagcac ccaccacgac    40

<210> SEQ ID NO 207
<211> LENGTH: 40
<212> TYPE: RNA
<213> ORGANISM: Artificial Sequence
<220> FEATURE:
<223> OTHER INFORMATION: Oligonucleotide

<400> SEQUENCE: 207
cgaacgaacu guggacccua cccacacugg gccaagcgau    40

<210> SEQ ID NO 208
<211> LENGTH: 40
<212> TYPE: RNA
<213> ORGANISM: Artificial Sequence
<220> FEATURE:
<223> OTHER INFORMATION: Oligonucleotide

<400> SEQUENCE: 208
cgcccuggaa cgagauuccu guaaaccccc aucuaguaga    40

<210> SEQ ID NO 209
<211> LENGTH: 40
<212> TYPE: RNA
<213> ORGANISM: Artificial Sequence
<220> FEATURE:
<223> OTHER INFORMATION: Oligonucleotide

<400> SEQUENCE: 209
caaggugacc gcgaacccua cccgccgcac gguaacagcg    40

<210> SEQ ID NO 210
<211> LENGTH: 40
<212> TYPE: RNA
<213> ORGANISM: Artificial Sequence
<220> FEATURE:
<223> OTHER INFORMATION: Oligonucleotide

<400> SEQUENCE: 210
cauccagacu acuggcccaa cccgccgcuc caaccccgug    40

<210> SEQ ID NO 211

-continued

<211> LENGTH: 40
<212> TYPE: RNA
<213> ORGANISM: Artificial Sequence
<220> FEATURE:
<223> OTHER INFORMATION: Oligonucleotide

<400> SEQUENCE: 211
cucucuccgu aaccaacaag ucccaaugaa caaccaccau 40

<210> SEQ ID NO 212
<211> LENGTH: 40
<212> TYPE: RNA
<213> ORGANISM: Artificial Sequence
<220> FEATURE:
<223> OTHER INFORMATION: Oligonucleotide

<400> SEQUENCE: 212
cacugaacga auggcaaccg ccaaacccua cccacacugg 40

<210> SEQ ID NO 213
<211> LENGTH: 40
<212> TYPE: RNA
<213> ORGANISM: Artificial Sequence
<220> FEATURE:
<223> OTHER INFORMATION: Oligonucleotide

<400> SEQUENCE: 213
caagcguaua cccuacccac acugagcuac auugcgcuga 40

<210> SEQ ID NO 214
<211> LENGTH: 40
<212> TYPE: RNA
<213> ORGANISM: Artificial Sequence
<220> FEATURE:
<223> OTHER INFORMATION: Oligonucleotide

<400> SEQUENCE: 214
gccgagagug agugaccaca accccgccca cacuggaaua 40

<210> SEQ ID NO 215
<211> LENGTH: 40
<212> TYPE: RNA
<213> ORGANISM: Artificial Sequence
<220> FEATURE:
<223> OTHER INFORMATION: Oligonucleotide

<400> SEQUENCE: 215
uuuccuaugg cgauaacuuc agccacgccg gcgccccgug 40

<210> SEQ ID NO 216
<211> LENGTH: 40
<212> TYPE: RNA
<213> ORGANISM: Artificial Sequence
<220> FEATURE:
<223> OTHER INFORMATION: Oligonucleotide

<400> SEQUENCE: 216
cgucacuccg ucccagccga cgaaguccgu aauuccucca 40

<210> SEQ ID NO 217
<211> LENGTH: 40
<212> TYPE: RNA
<213> ORGANISM: Artificial Sequence
<220> FEATURE:
<223> OTHER INFORMATION: Oligonucleotide

<400> SEQUENCE: 217

-continued ccacccgaag caaaucaagc ccgacggcgc ucggaccaac 40

<210> SEQ ID NO 218
<211> LENGTH: 39
<212> TYPE: RNA
<213> ORGANISM: Artificial Sequence
<220> FEATURE:
<223> OTHER INFORMATION: Oligonucleotide

<400> SEQUENCE: 218
cgaacugaag cuagcguaac ccuacccaca cugcacgug 39

<210> SEQ ID NO 219
<211> LENGTH: 40
<212> TYPE: RNA
<213> ORGANISM: Artificial Sequence
<220> FEATURE:
<223> OTHER INFORMATION: Oligonucleotide

<400> SEQUENCE: 219
accucgaccc uucaccugac ucucccagaa guucuguuuc 40

<210> SEQ ID NO 220
<211> LENGTH: 39
<212> TYPE: RNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (37)..(39)
<223> OTHER INFORMATION: “n” = c, u, a or g

<400> SEQUENCE: 220
caauccauac gcacccgguc cacacugggu uggagcnnn 39

<210> SEQ ID NO 221
<211> LENGTH: 40
<212> TYPE: RNA
<213> ORGANISM: Artificial Sequence
<220> FEATURE:
<223> OTHER INFORMATION: Oligonucleotide

<400> SEQUENCE: 221
aauggaauca cugaaggccc uccguagcac cuaacacagu 40

<210> SEQ ID NO 222
<211> LENGTH: 40
<212> TYPE: RNA
<213> ORGANISM: Artificial Sequence
<220> FEATURE:
<223> OTHER INFORMATION: Oligonucleotide

<400> SEQUENCE: 222
gcauccugcc agcggcgacg gaccuucgcc cacaggccuc 40

<210> SEQ ID NO 223
<211> LENGTH: 40
<212> TYPE: RNA
<213> ORGANISM: Artificial Sequence
<220> FEATURE:
<223> OTHER INFORMATION: Oligonucleotide

<400> SEQUENCE: 223
uuauauagca cacugaagcc cucagcaaaa ccuccacagg 40

-continued

<210> SEQ ID NO 224
<211> LENGTH: 40
<212> TYPE: RNA
<213> ORGANISM: Artificial Sequence
<220> FEATURE:
<223> OTHER INFORMATION: Oligonucleotide

<400> SEQUENCE: 224
uaugaaauca cagaagcccg cguucgacac cuccacuguu 40

<210> SEQ ID NO 225
<211> LENGTH: 48
<212> TYPE: RNA
<213> ORGANISM: Artificial Sequence
<220> FEATURE:
<223> OTHER INFORMATION: Oligonucleotide

<400> SEQUENCE: 225
caaacucaca gacuccaacu gcaggagcac ccacccacac ugggacag 48

<210> SEQ ID NO 226
<211> LENGTH: 40
<212> TYPE: RNA
<213> ORGANISM: Artificial Sequence
<220> FEATURE:
<223> OTHER INFORMATION: Oligonucleotide

<400> SEQUENCE: 226
auccccgccg uaagccgucc ugauggacac cacacgccgc 40

<210> SEQ ID NO 227
<211> LENGTH: 18
<212> TYPE: RNA
<213> ORGANISM: Artificial Sequence
<220> FEATURE:
<223> OTHER INFORMATION: RNA aptamer

<400> SEQUENCE: 227
acaaagcugr agwacuua 18

<210> SEQ ID NO 228
<211> LENGTH: 40
<212> TYPE: RNA
<213> ORGANISM: Artificial Sequence
<220> FEATURE:
<223> OTHER INFORMATION: RNA aptamer

<400> SEQUENCE: 228
gggaugggga cuauaccgcg uaaugcugcc uccccauucc 40

<210> SEQ ID NO 229
<211> LENGTH: 32
<212> TYPE: RNA
<213> ORGANISM: Artificial Sequence
<220> FEATURE:
<223> OTHER INFORMATION: RNA aptamer

<400> SEQUENCE: 229
auggggacua uaccggcaau cgugcauccc cu 32

<210> SEQ ID NO 230
<211> LENGTH: 40
<212> TYPE: RNA
<213> ORGANISM: Artificial Sequence
<220> FEATURE:
<223> OTHER INFORMATION: RNA aptamer
<400> SEQUENCE: 230

-continued

```
gggaugggga ccauaacucu aacgggugaa ucccgcaucu                              40


<210> SEQ ID NO 231
<211> LENGTH: 35
<212> TYPE: RNA
<213> ORGANISM: Artificial Sequence
<220> FEATURE:
<223> OTHER INFORMATION: RNA aptamer

<400> SEQUENCE: 231

gggaugggug auaaccacuc uggugaaccc cuccc                                   35


<210> SEQ ID NO 232
<211> LENGTH: 39
<212> TYPE: RNA
<213> ORGANISM: Artificial Sequence
<220> FEATURE:
<223> OTHER INFORMATION: RNA aptamer

<400> SEQUENCE: 232

gggaugggcg ccauacgcac auugcugcau cgccuuccc                               39


<210> SEQ ID NO 233
<211> LENGTH: 41
<212> TYPE: RNA
<213> ORGANISM: Artificial Sequence
<220> FEATURE:
<223> OTHER INFORMATION: RNA aptamer

<400> SEQUENCE: 233

gagggauggg accauaacga cuacucguga aucccaccau c                            41


<210> SEQ ID NO 234
<211> LENGTH: 38
<212> TYPE: RNA
<213> ORGANISM: Artificial Sequence
<220> FEATURE:
<223> OTHER INFORMATION: RNA aptamer

<400> SEQUENCE: 234

gagggauggg accauacgca cauugcugaa uccccuc                                 38


<210> SEQ ID NO 235
<211> LENGTH: 36
<212> TYPE: RNA
<213> ORGANISM: Artificial Sequence
<220> FEATURE:
<223> OTHER INFORMATION: RNA aptamer

<400> SEQUENCE: 235

gggaugggac uauauucgga aucuggacuc ccaccu                                  36


<210> SEQ ID NO 236
<211> LENGTH: 34
<212> TYPE: RNA
<213> ORGANISM: Artificial Sequence
<220> FEATURE:
<223> OTHER INFORMATION: RNA aptamer

<400> SEQUENCE: 236

gggaugggca cuauacgcau cuugcugccu gccc                                    34


<210> SEQ ID NO 237
<211> LENGTH: 37
<212> TYPE: RNA
<213> ORGANISM: Artificial Sequence
```

-continued

<220> FEATURE:
<223> OTHER INFORMATION: RNA aptamer

<400> SEQUENCE: 237
agggaugggc cauacgugga cgacugcacc cgacccu 37

<210> SEQ ID NO 238
<211> LENGTH: 35
<212> TYPE: RNA
<213> ORGANISM: Artificial Sequence
<220> FEATURE:
<223> OTHER INFORMATION: RNA aptamer

<400> SEQUENCE: 238
gggaugggcc auaaccacuu uggugaaccc accca 35

<210> SEQ ID NO 239
<211> LENGTH: 33
<212> TYPE: RNA
<213> ORGANISM: Artificial Sequence
<220> FEATURE:
<223> OTHER INFORMATION: RNA aptamer

<400> SEQUENCE: 239
ggaugggcga uaaccaacau ggugauccca uuc 33

<210> SEQ ID NO 240
<211> LENGTH: 34
<212> TYPE: RNA
<213> ORGANISM: Artificial Sequence
<220> FEATURE:
<223> OTHER INFORMATION: RNA aptamer

<400> SEQUENCE: 240
gggaugggcg auauacacau uggugauccc accc 34

<210> SEQ ID NO 241
<211> LENGTH: 35
<212> TYPE: RNA
<213> ORGANISM: Artificial Sequence
<220> FEATURE:
<223> OTHER INFORMATION: RNA aptamer

<400> SEQUENCE: 241
gggaugggcu auauacacgc uggugauccc aucuc 35

<210> SEQ ID NO 242
<211> LENGTH: 39
<212> TYPE: RNA
<213> ORGANISM: Artificial Sequence
<220> FEATURE:
<223> OTHER INFORMATION: RNA aptamer

<400> SEQUENCE: 242
gggaugggga cuauacguga acgacugcau ccacuuccc 39

<210> SEQ ID NO 243
<211> LENGTH: 33
<212> TYPE: RNA
<213> ORGANISM: Artificial Sequence
<220> FEATURE:
<223> OTHER INFORMATION: RNA aptamer

<400> SEQUENCE: 243
gggaugggua auaacuguau ggugaaccca ccc 33